US011660359B2

(12) United States Patent
Shedlock et al.

(10) Patent No.: US 11,660,359 B2
(45) Date of Patent: May 30, 2023

(54) SYSTEMS AND METHODS FOR IRRADIATION

(71) Applicant: Varex Imaging Corporation, Salt Lake City, UT (US)

(72) Inventors: Daniel Shedlock, Knoxville, TN (US); David Nisius, Des Plaines, IL (US); Gregory Andrews, West Jordan, UT (US); Jeff Adams, Herriman, UT (US)

(73) Assignee: Varex Imaging Corporation, Salt Lake City, UT (US)

( * ) Notice: Subject to any disclaimer, the term of this patent is extended or adjusted under 35 U.S.C. 154(b) by 32 days.

(21) Appl. No.: 17/234,714

(22) Filed: Apr. 19, 2021

(65) Prior Publication Data

US 2022/0331462 A1 Oct. 20, 2022

(51) Int. Cl.
*A61L 2/08* (2006.01)
*G21K 1/10* (2006.01)
*G21K 5/08* (2006.01)
*G21K 5/10* (2006.01)

(52) U.S. Cl.
CPC .............. *A61L 2/082* (2013.01); *G21K 1/10* (2013.01); *G21K 5/08* (2013.01); *G21K 5/10* (2013.01); *A61L 2202/21* (2013.01)

(58) Field of Classification Search
None
See application file for complete search history.

(56) References Cited

U.S. PATENT DOCUMENTS

| 2,785,313 | A | * | 3/1957 | Trump | B29C 71/04 |
| | | | | | 250/455.11 |
| 3,780,308 | A | * | 12/1973 | Nablo | B67C 7/0073 |
| | | | | | 250/493.1 |
| 7,145,155 | B2 | * | 12/2006 | Nablo | B65B 55/08 |
| | | | | | 250/492.1 |
| 7,580,506 | B2 | * | 8/2009 | DeSalvo | A61L 2/08 |
| | | | | | 378/138 |
| 7,634,051 | B2 | * | 12/2009 | Robinson | G01V 5/0058 |
| | | | | | 378/57 |
| 7,767,987 | B2 | * | 8/2010 | Eguchi | G21K 5/00 |
| | | | | | 436/1 |

(Continued)

OTHER PUBLICATIONS

PCT/US2022/025361, International Search Report dated Aug. 9, 2022.
PCT/US2022/025361, Written Opinion dated Aug. 9, 2022.

*Primary Examiner* — Thomas R Artman
(74) *Attorney, Agent, or Firm* — Laurence & Phillips IP Law

(57) ABSTRACT

Technology is described to uniformly apply doses of radiation to a target material. An irradiation device may comprise an enclosure configured to receive a target material and a source configured to emit primary radiation within the enclosure. The primary radiation may be configured to irradiate at least a first portion of the target material. The irradiation device may further comprise a scattering medium disposed within the enclosure. The scattering medium may be configured to produce secondary radiation through scatter interactions in response to the primary radiation, the secondary radiation configured to irradiate at least a second portion of the target material. A thickness of the scattering medium relative to the primary radiation may have a thickness of at least 3 millimeters).

26 Claims, 21 Drawing Sheets

(56) References Cited

U.S. PATENT DOCUMENTS

| | | | | |
|---|---|---|---|---|
| 7,998,404 | B2* | 8/2011 | Huang | A61L 2/08 422/291 |
| 8,034,287 | B2* | 10/2011 | Freeman | A61L 2/08 430/510 |
| 8,280,004 | B2* | 10/2012 | DeSalvo | A61L 2/082 378/68 |
| 8,298,483 | B2* | 10/2012 | Freeman | A61L 2/08 430/510 |
| 8,376,013 | B2* | 2/2013 | Bourke, Jr. | A61K 41/0057 522/66 |
| 8,461,561 | B2* | 6/2013 | Freeman | A61L 2/08 422/22 |
| 8,471,229 | B2* | 6/2013 | Freeman | A61L 2/081 250/515.1 |
| 8,524,151 | B2* | 9/2013 | Freeman | A61L 2/08 430/4 |
| 8,709,340 | B2* | 4/2014 | Freeman | A61L 2/087 430/4 |
| 8,790,589 | B2* | 7/2014 | Cirri | A61L 2/087 422/292 |
| 8,956,575 | B2* | 2/2015 | Freeman | A61L 2/087 422/291 |
| 9,339,568 | B2* | 5/2016 | Huang | A61L 2/10 |
| 9,671,089 | B2* | 6/2017 | Strauß | F21S 41/16 |
| 10,105,112 | B2* | 10/2018 | Utsumi | A61B 6/025 |
| 11,156,551 | B2* | 10/2021 | Schultz | G02B 21/086 |
| 11,278,861 | B2* | 3/2022 | Bourke, Jr. | G02B 5/008 |
| 2006/0192140 | A1* | 8/2006 | Nablo | A61L 2/08 250/492.1 |
| 2007/0280851 | A1* | 12/2007 | Freeman | A61L 2/08 422/1 |
| 2008/0010947 | A1* | 1/2008 | Huang | A61L 2/10 53/425 |
| 2008/0181364 | A1* | 7/2008 | DeSalvo | A61L 2/08 378/138 |
| 2008/0240356 | A1 | 10/2008 | Robinson | |
| 2009/0134338 | A1* | 5/2009 | Eguchi | G21K 5/00 250/492.3 |
| 2009/0294692 | A1* | 12/2009 | Bourke, Jr. | B01J 19/12 250/492.1 |
| 2010/0209290 | A1* | 8/2010 | Cirri | A61L 2/087 422/186 |
| 2012/0006999 | A1* | 1/2012 | Freeman | A61L 2/08 250/455.11 |
| 2012/0007003 | A1* | 1/2012 | Freeman | A61L 2/087 250/505.1 |
| 2012/0009083 | A1* | 1/2012 | Freeman | A61L 2/08 422/22 |
| 2012/0009084 | A1* | 1/2012 | Freeman | A61L 2/081 422/22 |
| 2012/0148025 | A1* | 6/2012 | DeSalvo | A61L 2/08 378/68 |
| 2013/0270453 | A1* | 10/2013 | Freeman | A61L 2/081 250/398 |
| 2014/0065012 | A1* | 3/2014 | Freeman | A61L 2/087 422/1 |
| 2014/0230373 | A1* | 8/2014 | Huang | A61L 2/081 264/488 |
| 2015/0003042 | A1 | 1/2015 | Strauss | |
| 2015/0124921 | A1 | 5/2015 | Groves et al. | |
| 2016/0228076 | A1 | 8/2016 | Utsumi et al. | |
| 2019/0339199 | A1 | 11/2019 | Schultz et al. | |
| 2020/0306717 | A1* | 10/2020 | Bourke, Jr. | C09D 201/00 |
| 2022/0331462 | A1* | 10/2022 | Shedlock | G21K 1/10 |

* cited by examiner

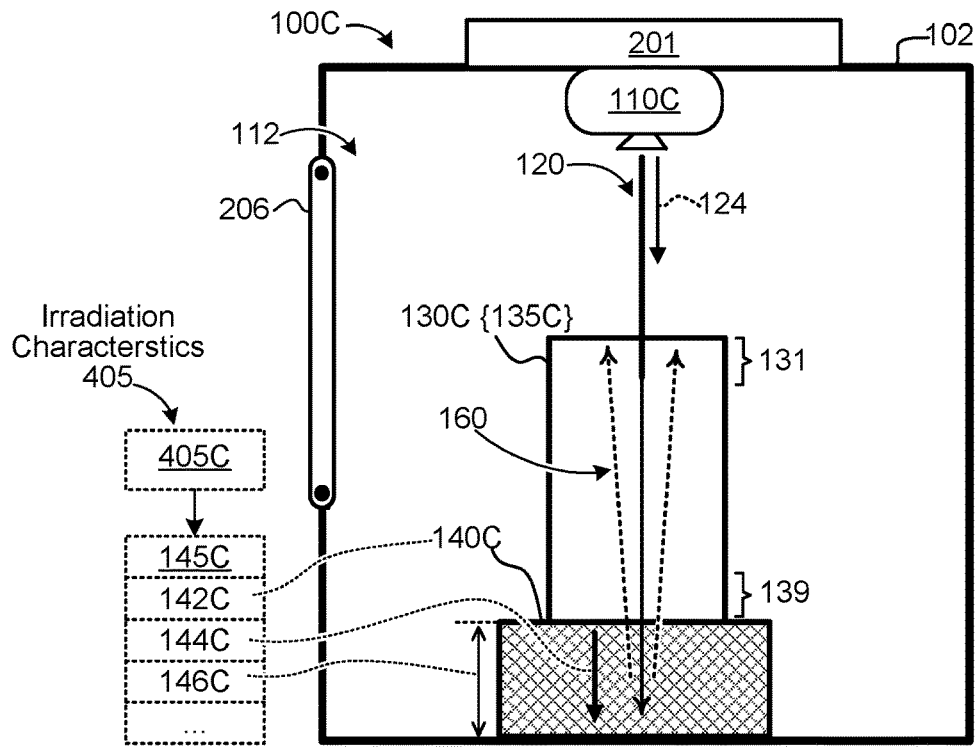
FIG. 4A
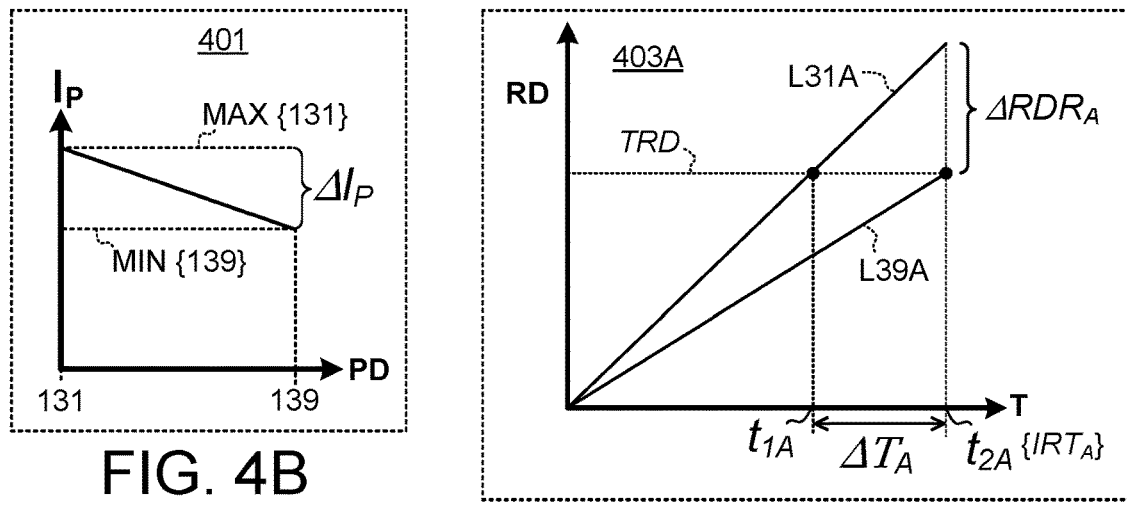
FIG. 4B
FIG. 4C
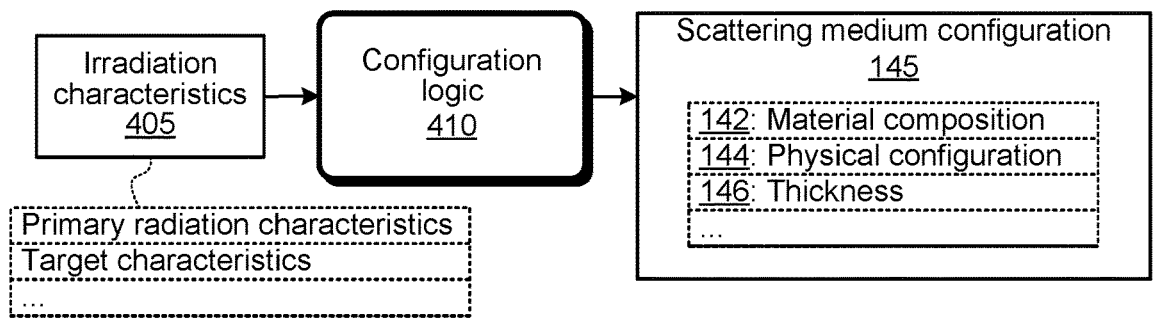
FIG. 4D

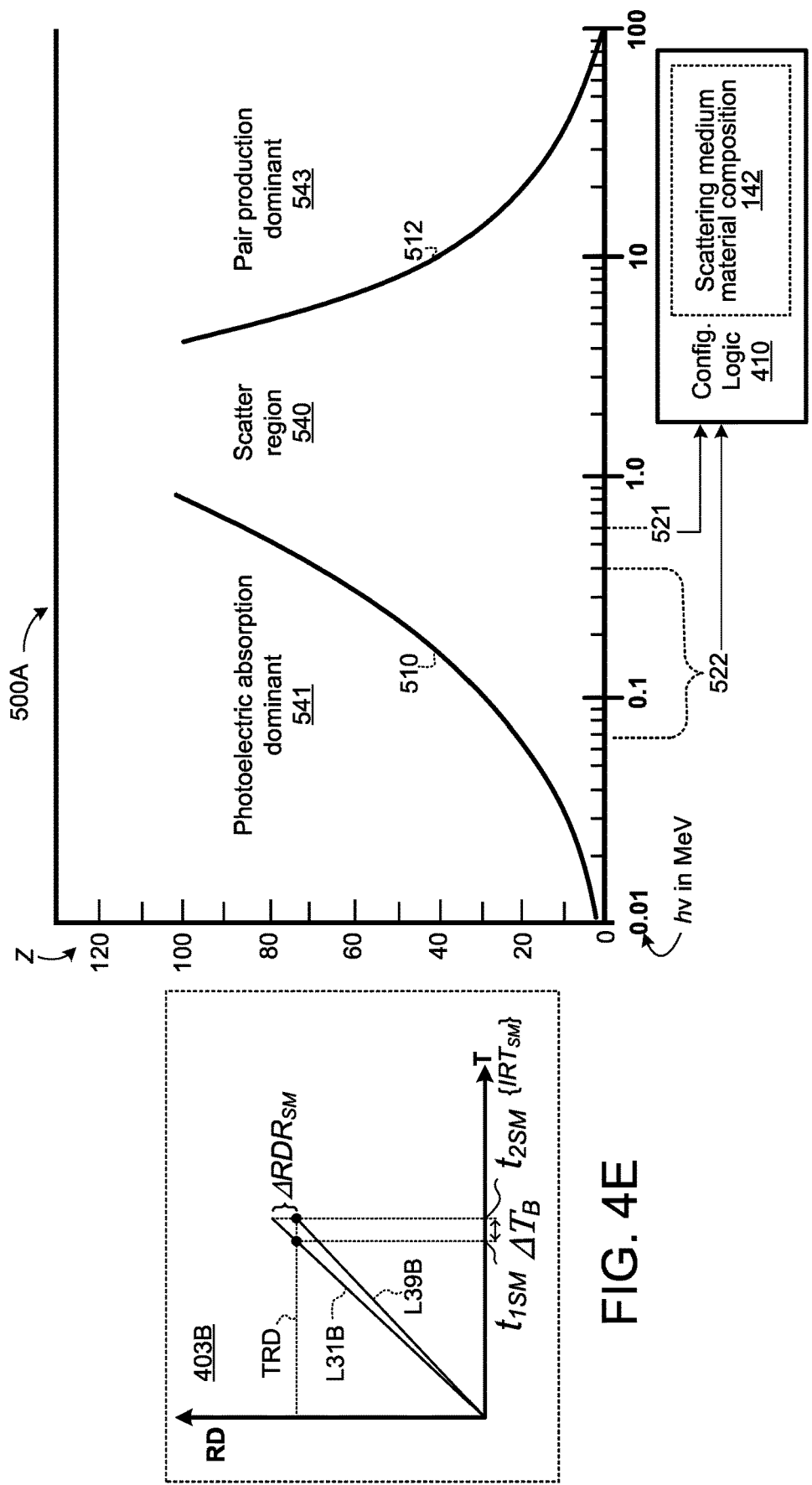

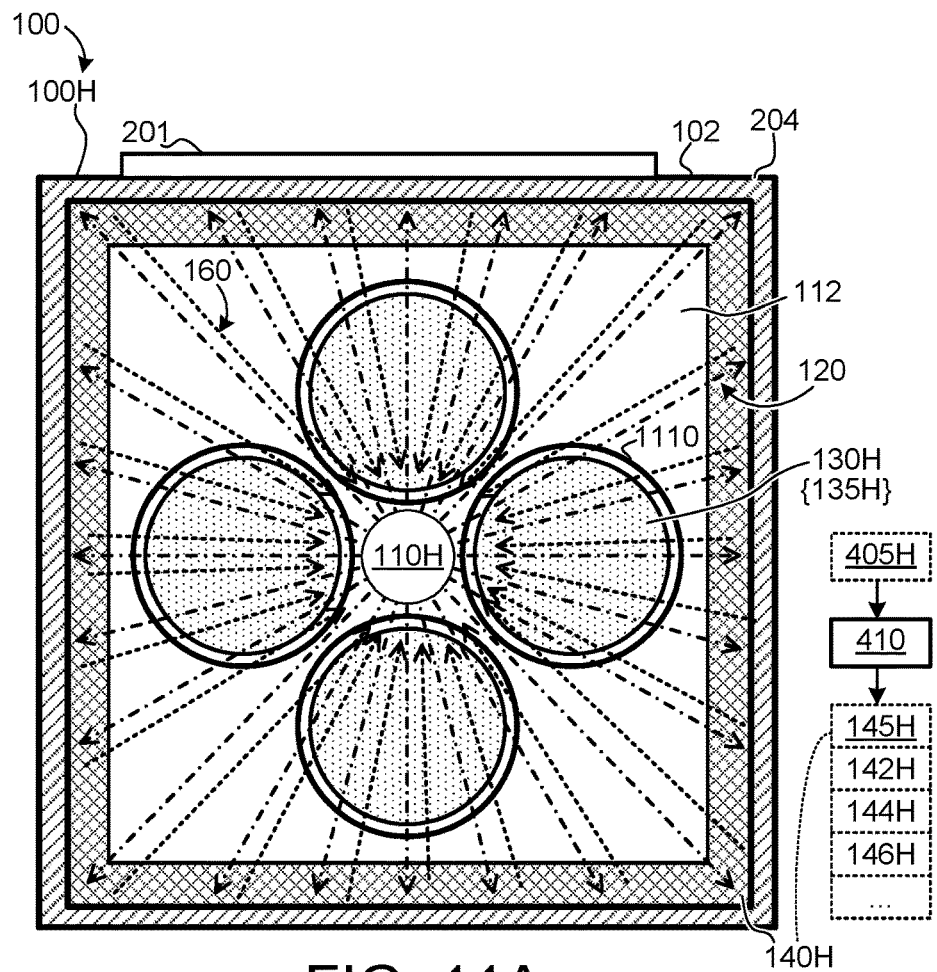
FIG. 11A
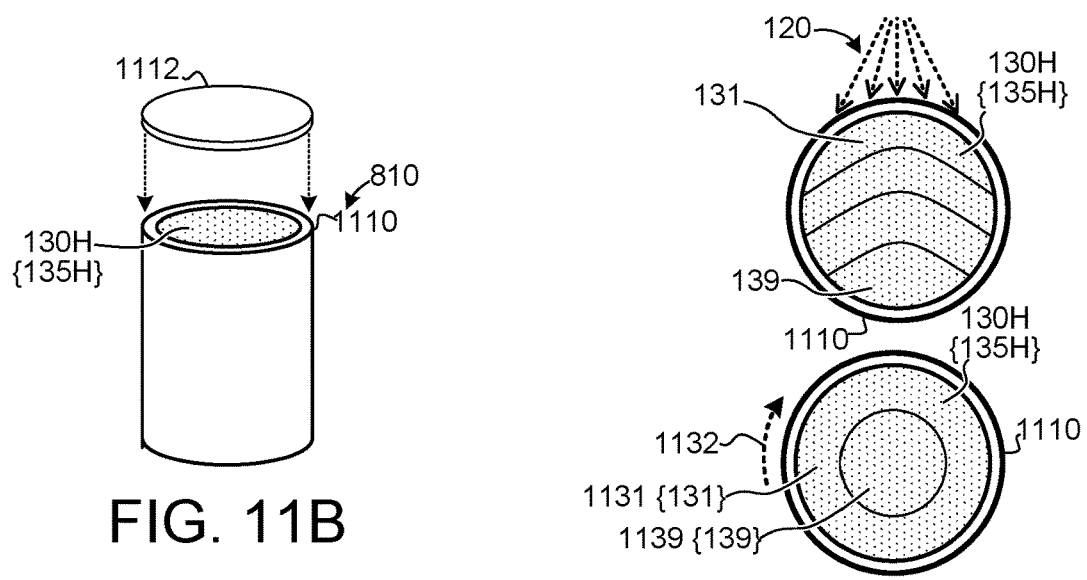
FIG. 11B
FIG. 11C

1600A

Enclose a target to be irradiated within an irradiation device comprising a scattering medium
1610

Emit first radiation into the interior volume of the irradiation device
1620

Cause second radiation to be emitted into the interior volume in response to the first radiation, the second radiation produced through scatter interactions between the first radiation and the scatter medium disposed within the enclosure of the irradiation apparatus
1630

Provide enclosure for target material
1640

Produce scattering medium for irradiation device
1620

Configure thickness of scattering medium to be 3 millimeters or greater
1660

FIG. 16B

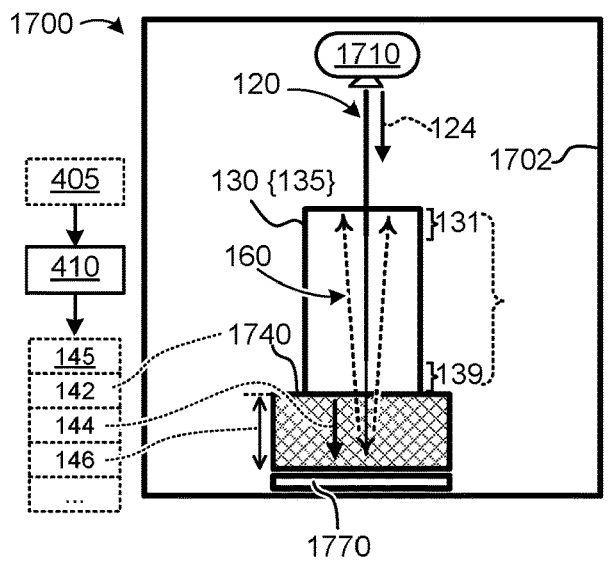

FIG. 17

SYSTEMS AND METHODS FOR IRRADIATION

BACKGROUND

Unless otherwise indicated herein, the approaches described in this section are not prior art to the claims in this disclosure and are not admitted to be prior art by inclusion in this section.

Penetrating electromagnetic radiation can be applied in a wide array of applications, including imaging, radiography, photography, scanning, sensing, testing, diagnostics, medical diagnostics, medical treatment and therapeutics, materials analysis, sterilization, and so on. Many of these applications involve irradiation of a target. In some situations, the physical configuration and/or position of the target relative to the radiation source(s) may result in non-uniform irradiation. For example, portions of the target that are closer to the radiation source may receive higher doses than portions that are further away (e.g., due to attenuation and/or absorption as the radiation penetrates the target).

Target non-uniformity can adversely impact many applications. For example, a sterilization operation may involve delivering a threshold radiation dose to a target. However, due to target non-uniformity, some portions of the target may reach the threshold well before other portions. To address these issues, the target material may be over-irradiated, which may result in increased irradiation time, decreased throughput, increased power consumption, damage to the over-irradiated portions of the target material, degradation in product quality, and so on. Alternatively, the target material may be shifted relative to the source during irradiation. These approaches can also have significant disadvantages, such as increased complexity and power consumption, reduced irradiation assurance (due to potential randomness or faults during physical manipulation), damage during physical manipulation, and so on.

BRIEF DESCRIPTION OF THE DRAWINGS

FIG. 4A illustrates another example of an irradiation device comprising a scattering medium.

FIG. 4B is a graph illustrating attenuation and/or absorption of primary radiation during penetration through a target.

FIG. 4C is a graph illustrating an example of non-uniform irradiation.

FIG. 4D illustrates an example of scattering medium configuration logic.

FIG. 4E is a graph illustrating irradiation performance improvements yielded by incorporation of a suitably configured scattering medium.

FIGS. 5A-D illustrate examples of radiation scatter interaction distributions as a function of material atomic number and radiation energy.

FIG. 11A illustrates another example of an irradiation device comprising a scattering medium.

FIGS. 11B-C illustrate examples of containers of an irradiation device.

FIGS. 16A-B are flow diagrams illustrating examples of techniques for irradiating a target.

FIG. 17 illustrates an example of an irradiation system.

DETAILED DESCRIPTION

Figure 1A:
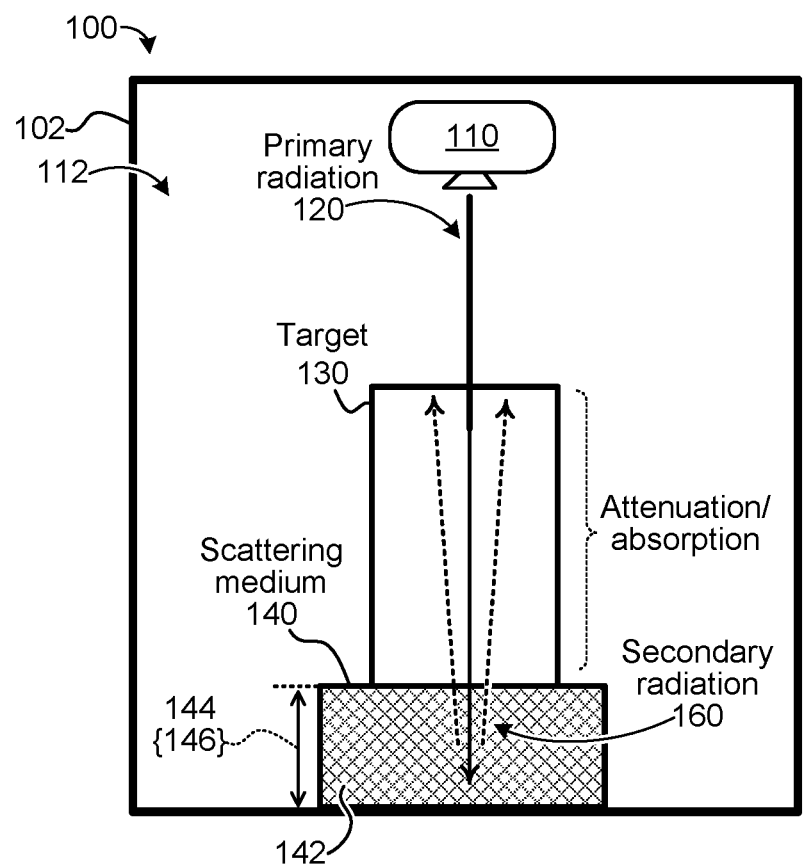
FIG. 1A illustrates an example of an irradiation device comprising a scattering medium.

Before any example implementations of the invention are described, it is to be understood that the invention is not limited in its application to the details of construction and the arrangement of components set forth in the following description or illustrated in the drawings. The invention is capable of being realized in any suitable implementation and of being practiced or of being carried out in various ways. Numbers provided in flow charts and processes are provided for clarity in illustrating steps and operations and do not necessarily indicate a particular order or sequence. Unless otherwise defined, the term "or" can refer to a choice of alternatives (e.g., a disjunction operator, or an exclusive or) or a combination of the alternatives (e.g., a conjunction operator, and/or, a logical or, or a Boolean OR).

The technology (systems, devices, methods, and non-transitory computer-readable storage media) described herein provides solutions to uniformly irradiate targets while avoiding over-irradiation and obviating the need for physical manipulation. The disclosed technology may, therefore, yield technological improvements to systems and methods for irradiation, including, but not limited to, increased efficiency, reduced irradiation time, increased throughput, reduced complexity, lower cost, higher irradiation assurance, lower target perturbation, and so on.

FIG. 1A illustrates an example of an irradiation apparatus or device 100. The irradiation device 100 may comprise a source 110 configured to produce primary radiation 120. The primary radiation 120 may be configured to deliver a specified radiation dose to a target 130.

As illustrated in FIG. 1A, the primary radiation 120 may be attenuated and/or absorbed during penetration through the target 130. As a result, the target 130 may receive a non-uniform dose of the primary radiation 120. In other words, different portions of the target 130 may receive different doses of the primary radiation 120. In the FIG. 1A example, the primary radiation 120 penetrates the target 130 from top to bottom and so the top portion of the target 130 (the portion nearest to the source 110) receives a more intense dose of the primary radiation 120 than the bottom portion (the portion furthest from the source 110) and the top portion of the target 130 may reach the specified radiation dose before the bottom portion. Moreover, delivering the specified radiation dose to the bottom portion of the target 130 may result in over-irradiation of the top portion.

The irradiation device 100 may be configured to balance the radiation dose received by the target 130 without the need for over-irradiation or physical manipulation. The radiation dose may be balanced by a scattering medium 140 disposed within the interior volume 112 of the enclosure 102. In the FIG. 1A example, the scattering medium 140 is positioned underneath the target 130 (e.g., opposite the primary radiation 120). The scattering medium 140 may be configured to emit secondary radiation 160 in response to the primary radiation 120. The secondary radiation 160 may penetrate the target 130 from bottom to top (as opposed to top to bottom as the primary radiation 120). The secondary radiation 160 produced by the scattering medium 140 may irradiate at least a portion of the target 130 (from bottom to top), thereby balancing the radiation dose received by the target 130. In other words, the secondary radiation 160 may reduce the difference in radiation dose delivered to the top and bottom portions of the target 130.

As disclosed in further detail herein, the secondary radiation 160 may be produced through scatter interactions within the scattering medium 140. The scattering medium 140 may be formed from materials configured to produce secondary radiation 160 in response to charged particles produced by the primary radiation 120. The materials comprising the scattering medium 140 may be selected based on an energy of the primary radiation 120. More specifically, the material composition 142 of the scattering medium 140 may be configured to include material(s) having atomic number(s) (Z) determined to produce scatter interactions at energy level(s) (and/or within an energy range) of the primary radiation 120. In some embodiments, the material composition 142 of the scattering medium 140 may include materials having atomic numbers (2) within a specified range, such as 20 or lower, 10 or lower, 8 or lower, or the like. The scattering medium 140 may comprise a thermoplastic, a thermoplastic polymer, high-density polyethylene (HDPE), aluminum, an aluminum alloy, or the like.

As disclosed herein, the secondary radiation 160 may be produced during penetration of charged particles through the scattering medium 140. As such, the amount of secondary radiation 160 produced by the scattering medium 140 may depend on a physical configuration 144 (e.g., shape) of the scattering medium 140, such as a thickness 146 of the scattering medium 140 relative to the primary radiation 120 (e.g., from top to bottom, as illustrated in the FIG. 1A example). The thickness 146 of the scattering medium 140 may be set at a point at which scatter interactions exceed photoelectric absorption of the scattering medium 140 by at least a threshold. In some embodiments, the thickness 146 of the scattering medium 140 may be at least 3 millimeters (mm) or 0.3 centimeters (cm); about 0.25 inches (in). Alternatively, the thickness 146 of the scattering medium 140 may be at least 6 mm or 0.6 cm (about 0.25 in). The thickness 146 of the scattering medium 140 may be 1 cm, 5 cm, 10 cm, or more. As disclosed in further detail herein, the thickness 146 of the scattering medium 140 may be configured to increase the amount and/or intensity of the secondary radiation 160 produced by the scattering medium 140. At thicknesses 146 of 3 millimeters and below, the scattering medium 140 may be unable to produce secondary radiation 160 capable of improving irradiation performance.

As disclosed in further detail herein, the scattering medium 140 may be configured to improve aspects of irradiation performance. The scattering medium 140 may be configured to a) reduce the radiation dose differential of the target 130 to 10% or less (e.g., reduce the difference between the radiation dose delivered to the top portion and the bottom portion of the target 130 to 10% or less), b) increase the radiation dose rate of the target 130 by 10% or more, c) decrease the irradiation time required to deliver a specified radiation dose to the target 130 by 10% or more, and/or the like.

Figure 1B:
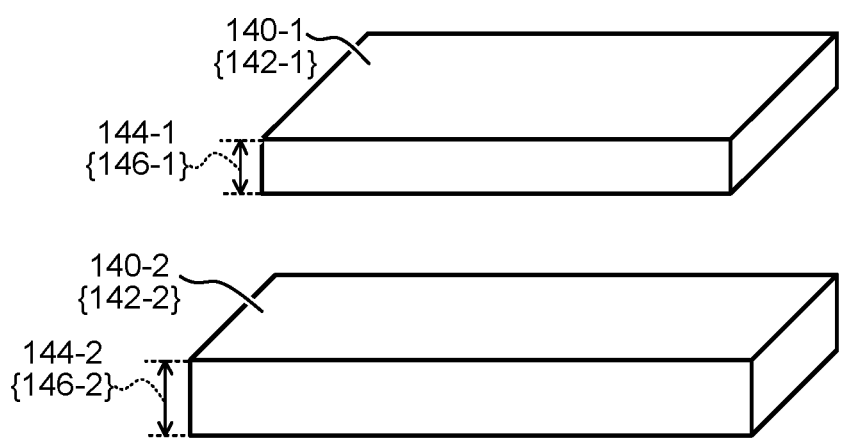
FIG. 1B illustrates examples of removable and/or replaceable scattering media.

In some embodiments, the scattering medium 140 of the irradiation device 100 may be secured and/or fixed within the interior of the enclosure 102. Alternatively, the scattering medium 140 may be removable and/or replaceable. FIG. 1B illustrates examples of replaceable scattering media 140. The scattering media 140-1 and 140-2 may be selectively deployed and removed from the interior volume 112 of the irradiation device 100. The first scattering medium 140-1 may be adapted to improve irradiation performance in response to primary radiation 120 at a first energy (and/or a first type of target 130) and the second scattering medium 140-2 may be adapted to improve irradiation performance in response to primary radiation 120 at a second energy, different from the first energy (and/or a second type of target 130, different from the first type). As such, and as disclosed in further detail herein, the material compositions 142-1 and 142-2 and/or physical configurations 144-1 and 144-2 (thicknesses 146-1 and 146-2) of the scattering media 140-1 and 140-2 may differ from one another.

Figure 2A:
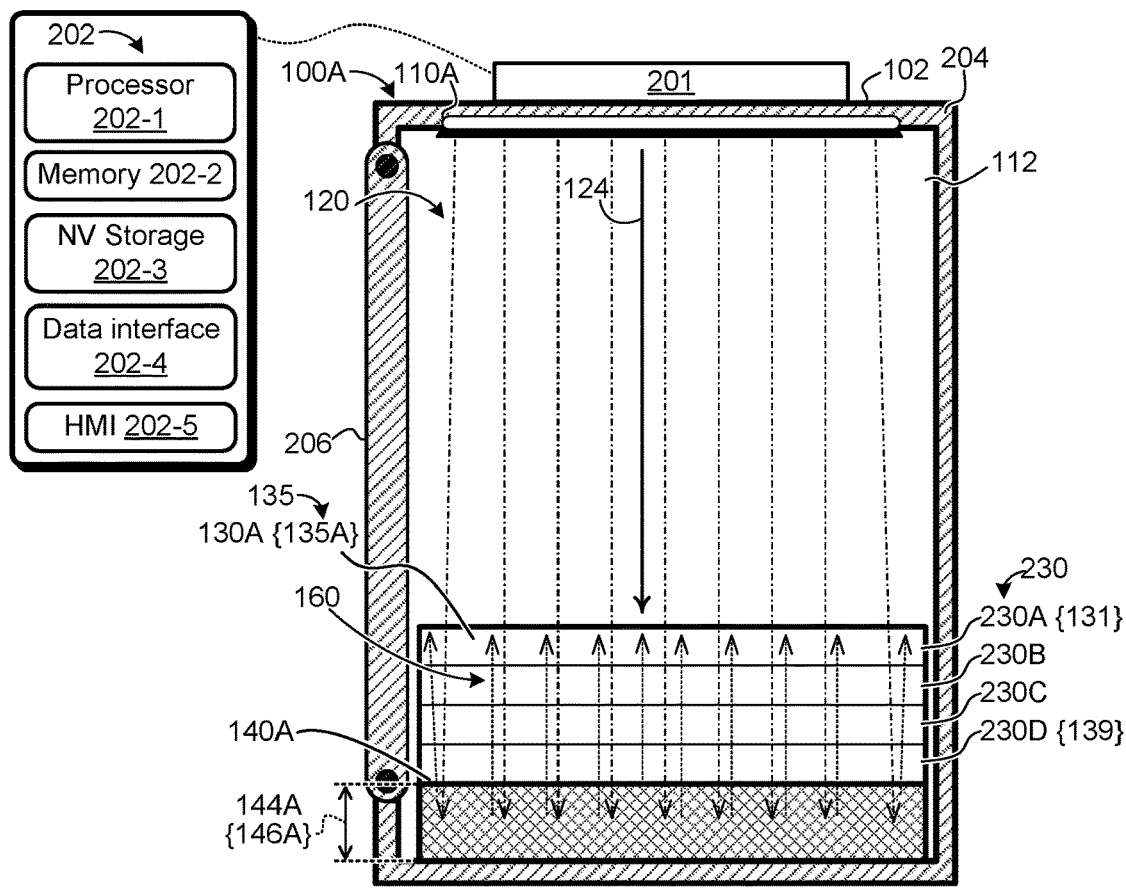
FIG. 2A illustrates another example of an irradiation device comprising a scattering medium.

FIG. 2A illustrates another example of an irradiation device 100A. The source 110A may be configured to emit primary radiation 120 and/or radiation beams in substantially parallel propagation direction(s) 124. As used herein, the propagation direction 124 of the primary radiation 120 may refer to a direction, angle, and/or vector at which the primary radiation 120, and/or beams of the primary radiation 120, are emitted from the source 110. For example, the propagation direction 124 may correspond to propagation of a central beam of the primary radiation 120. FIG. 2A illustrates a cross section of the irradiation device 100A, the cross section substantially parallel to the propagation direction(s) 124 of the primary radiation 120.

In the FIG. 2A example, the irradiation device 100A comprises an enclosure 102 configured to at least partially enclose an interior volume 112. The enclosure 102 may incorporate and/or comprise shielding 204 configured to prevent (or reduce) radiation leakage from the interior volume 112. The irradiation device 100A may further include and/or be coupled to control logic 201. In some implementations, the control logic 201 may comprise and/or be embodied by computing resources 202, which may include, but are not limited to: a processor 202-1, memory 202-2, non-volatile (NV) storage 202-3, a data interface 202-4, a human-machine interface (HMI) 202-5, and/or the like.

The processor 202-1 may include any suitable processing resources, such as a controller, control logic, a programmable controller, a programmable logic controller (PLC), logic circuitry, processing circuitry, computation circuitry, a processing unit, a central processing unit (CPU), a processor core, an Arithmetic Logic Unit (ALU), a general-purpose processor, an application-specific integrated circuit (ASIC), programmable processing elements, programmable logic, a Field Programmable Gate Array (FPGA), a system-on-chip (SoC), and/or the like. The memory 202-2 may include any suitable memory resource, such as volatile memory, non-volatile memory, random access memory (RAM), dynamic RAM (DRAM), synchronous DRAM (SDRAM), static RAM (SRAM), cache memory, and/or the like. The NV storage 202-3 may include any suitable non-transitory, persistent, and/or NV storage resource, including, but not limited to a non-transitory storage device, a persistent storage device, an internal storage device, an external storage device, a remote storage device, Network Attached Storage (NAS) resources, a magnetic disk drive, a hard disk drive (HDD), a solid-state storage device (SSD), a Flash memory device, and/or the like. The NV storage may store computer-readable instructions configured to cause the processor to implement methods for irradiation, as disclosed herein. The data interface 202-4 may include any suitable data and/or communication resource such as, an input/output (I/O) interface, an I/O port, a communication interface, a network interface, a Universal Serial Bus (USB) interface, and/or the like. The HMI 202-5 may comprise any suitable HMI components, including, but not limited to input devices, keyboards, pointing devices, audio input devices, touch input devices, output devices, audio output devices, display devices, touch screen devices, feedback devices, haptic feedback devices, and/or the like.

The control logic 201 may include external interfaces, such as address and data bus interfaces, interrupt interfaces, or the like. The control logic 201 may include other interface devices, such as logic chipsets, hubs, memory controllers, communication interfaces, or the like to connect the control logic 201 to internal and external components. The control logic 201 may be configured to control the variety of operations described herein. The control logic 201 may include connections to the enclosure 102, source 110A, and/or other components of the irradiation device 100A, including connections to apply voltages and/or supply current to the source 110A. The control logic 201 may be configured to implement irradiation operations, such as sterilization operations or the like. Implementing an irradiation operation may comprise configuring the source 110A to emit primary radiation 120 at a determined intensity and/or for a determined irradiation time, as disclosed herein.

The enclosure 102 may have an open configuration and a closed configuration. In some implementations, the enclosure 102 may comprise an access mechanism 206 configured to transition between the open and closed configurations. The control logic 201 may comprise and/or be coupled to a sensor configured to determine whether the enclosure 102 is in the closed configuration. The control logic 201 may prevent the source 110B from emitting primary radiation 120 in response to determining that the enclosure 102 is not in the closed configuration. The access mechanism 206 may comprise any suitable means for selectively accessing and/or enclosing the interior volume 112 including, but not limited to: a door, a mechanical door, an iris door, a diaphragm, a mechanical diaphragm, a latch, a seal, a hatch, a lock, a cap, a panel, shielding 204, and/or the like. Although examples of access mechanisms 206 are described herein, the disclosure is not limited in this regard and could be adapted to incorporate any suitable type of access mechanism 206 having any suitable configuration (e.g., access mechanism(s) 206 disposed at and/or on any suitable location of the enclosure 102).

The irradiation device 100A is configured to irradiate a target 130A. The target 130 (e.g., target 130A) may comprise one or more objects, substances, and/or materials, including, but not limited to: consumable products, medical devices, biological substances, such as blood or tissue, food products, agricultural products, agricultural materials, crops, devices under test, assays, analysis subject, analysis sample, and/or the like. In the FIG. 2A example, the target 130A comprises an agricultural product (a target material 130A). The target material 130A may comprise cannabis having a density of about 0.1 grams per cubic centimeter (g/cc) arranged in a pile or stack having a depth of about 4 inches (or 10.2 cm) relative to the propagation direction 124 of the primary radiation 120 (per first target characteristics 135A).

In some implementations, the physical characteristics of a target 130 (target characteristics 135) may determine a degree of irradiation non-uniformity exhibited by the target 130. As used herein, target characteristics 135 may refer to any information pertaining to a target 130 including, but not limited to: a composition of the target 130 (e.g., material(s) comprising the target 130), a density of the target 130, photoelectric absorption and/or attenuation characteristics of the target 130, a position of the target 130 relative to the source 110 of the irradiation device 100 and/or propagation direction 124 of the primary radiation 120, an orientation of the target 130 relative to the source 110 and/or propagation direction 124 of the primary radiation 120, a depth or thickness of the target 130 relative to the propagation direction 124 of the primary radiation 120, and/or the like. In the FIG. 2A example, the target characteristics 135A may determine a degree of non-uniformity exhibited by the target material 130A.

Figure 2B:
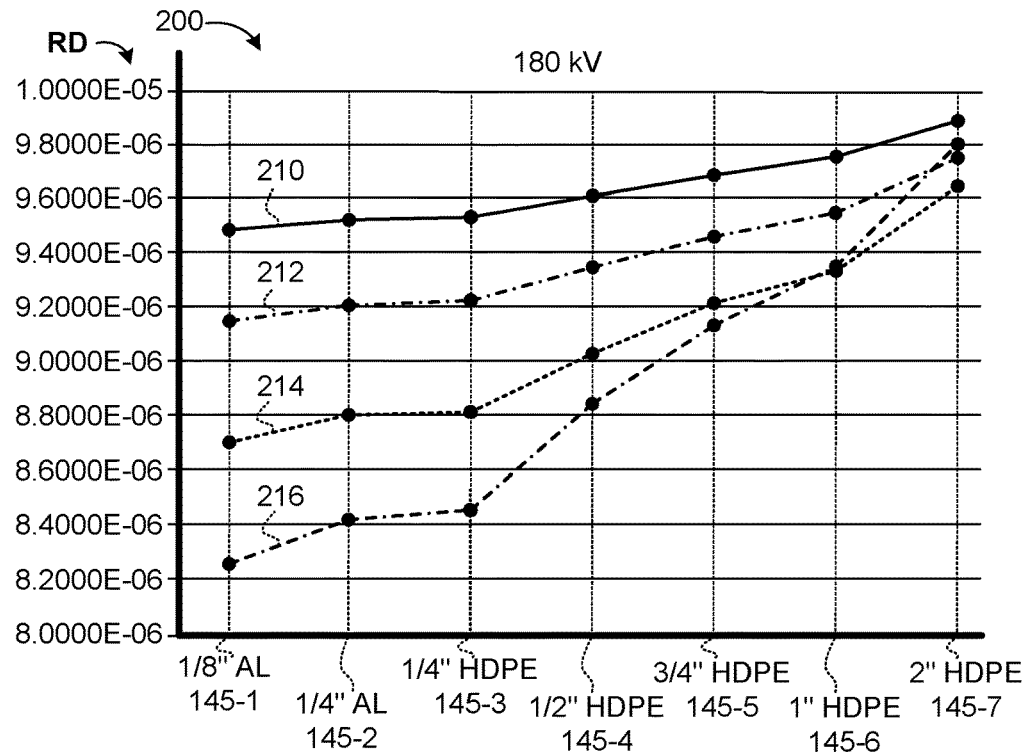
FIG. 2B is a graph illustrating radiation doses delivered to respective exposure regions of target material having a first physical arrangement relative to the primary radiation.

In FIG. 2A, the non-uniformity of the target material 130A may be represented by layers 230A-D, each layer 230 comprising target material 130B at a respective depth relative to the propagation direction 124 of the primary radiation 120. In FIGS. 2A-2B, each of the layers 230A-D is a specified thickness to illustrate the non-uniformity of the irradiation on the target material 130A, but the target material 130A may be continuous with no barrier or different material separating the layers 230A-D. The layer 230A closest to the source 110A may receive a highest dose of the primary radiation 120 (may comprise and/or correspond to a maximum-exposure (MAX) region 131 of the target material 130A) and the layer 230D furthest from the source 110A may receive a lowest dose of the primary radiation (may comprise and/or correspond to a minimum-exposure (MIN) region 139).

The irradiation device 100A may comprise a scattering medium 140A. As illustrated in FIG. 2A, the scattering medium 140A may be disposed below the target material 130A relative to the propagation direction 124 of the primary radiation 120 (e.g., beneath layer 230D) per a physical configuration 144A of the scattering medium 140A. The scattering medium 140A may have a determined thickness 146A relative to the propagation direction 124 of the primary radiation 120. The scattering medium 140A may be configured to improve aspects of irradiation performance, as illustrated in FIG. 2B below.

FIG. 2B includes a graph 200 illustrating radiation dosage differentials (ΔRD) between portions of target material 130A disposed within respective layers 230A-D. In the FIG. 2B example, the irradiation device 100A may be configured to irradiate the target material 130A with x-ray radiation at an energy of about 180 keV. The vertical axis shows RD and the horizontal axis corresponds to scattering media 140A having respective scattering medium configurations 145-1 through 145-7. A scattering medium configuration 145 may pertain to any property or characteristic of a scattering medium 140 (e.g., the scattering medium 140A), including, but not limited to: the material composition 142 of the scattering medium 140, a physical configuration 144 of the scattering medium 140 (e.g., a shape of the scattering medium 140), a thickness 146 of the scattering medium 140, and/or the like. Performance improvements, such as reduced non-uniformity (ΔRDR), increased radiation dose rate (ΔRD), and decreased irradiation time (ΔIRT), yielded by scattering medium configurations 145-1 through 145-7 (Mtrl & Thck 145) specifying respective material compositions 142 (Mtrl 142) and thicknesses 146 are listed below in Table 1.

TABLE 1

| Radiation Energy: 180 keV | | Target Characteristics 135B: 4 inches deep | | | |
|---|---|---|---|---|---|
| Mtrl & Thck 145 | Mtrl 142 | Thickness 146 (inches/cm) | ΔRDR | ΔRD | ΔIRT |
| None | None | None | 15% | 0% | 0% |
| 145-1 | AL | 0.125 in/0.32 cm | 13% | 5% | 7% |
| 145-2 | AL | 0.25 in/0.61 cm | 10% | 6% | 11% |
| 145-3 | HDPE | 0.25 in/0.62 cm | 9% | 6% | 12% |
| 145-4 | HDPE | 0.50 in/1.27 cm | 8% | 7% | 14% |
| 145-5 | HDPE | 0.75 in/1.9 cm | 6% | 8% | 17% |
| 145-6 | HDPE | 1.0 in/2.54 cm | 5% | 9% | 19% |
| 145-7 | HDPE | 2.0 in/5.08 cm | 2.5% | 10% | 22.5% |

Without the benefit of a suitably configured scattering medium 140A, the ΔRDR between the MAX region 131 (layer 230A) and the MIN region 139 (layer 230D) of the target material 130A may be about 15% (or more). In FIG. 2B, plot line 510 shows the RD delivered to the MAX region 131 (layer 230A) for scattering media 140A corresponding to each scattering medium configuration 145-1 through 145-7, plot line 512 shows the RD delivered to layer 230B, plot line 214 shows the RD delivered to layer 230C, and plot line 216 shows the RD delivered to the MIN region 139 (layer 230D).

As illustrated in FIG. 2B, the scattering medium configuration 145-7 (HDPE having a thickness 146 of 2 in/5.08 cm) reduces ΔRDR to about 2.5% (from an ΔRDR of about 15% for implementations that do not include a suitably configured scattering medium 140). The scattering medium configuration 145-7 may also increase the total RD delivered to layers 230A-D (expressed as ΔRD in Table 1). The scattering medium configuration 145-7 produces a ΔRD of about 10%, resulting in a reduction to irradiation time (ΔIRT) of about 22.5% as compared to over-irradiation (12.5% due to reduced ΔRDR and 10% due to ΔRD). Performance improvements yielded by scattering medium configurations 145-1 through 145-6 for the scattering medium 140A of the irradiation device 100A are illustrated in FIG. 2B and Table 1.

Figure 3A:
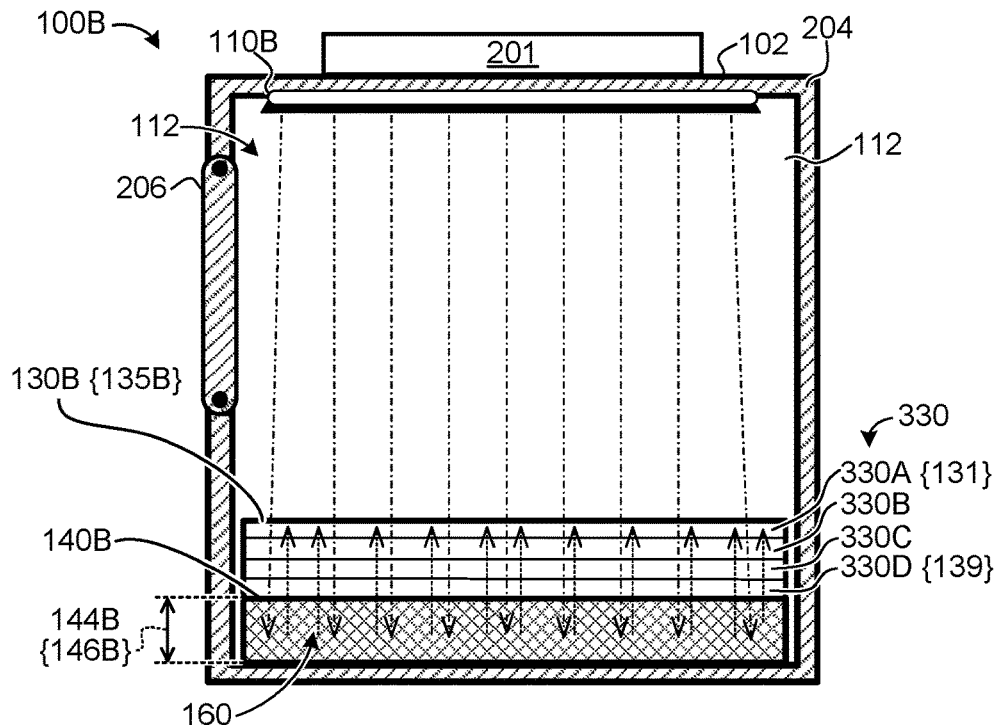
FIG. 3A illustrates another example of an irradiation device comprising a scattering medium.

FIG. 3A illustrates another example of an irradiation device 100B. In the FIG. 3A example, the target material 130B may have second target characteristics 135B, different from the first target characteristics 135A; the target material 130B may be arranged in a pile that is about half as deep as in the FIG. 2A example (e.g., about 2 inches deep as opposed to 4 inches deep). The non-uniformity of the target 130B may be represented by layers 330A-D, each layer 330 corresponding to a respective depth in the propagation direction 124 of the primary radiation 120. The irradiation device 100B may comprise a scattering medium 140B having a physical configuration 144B and/or thickness 146B.

Figure 3B:
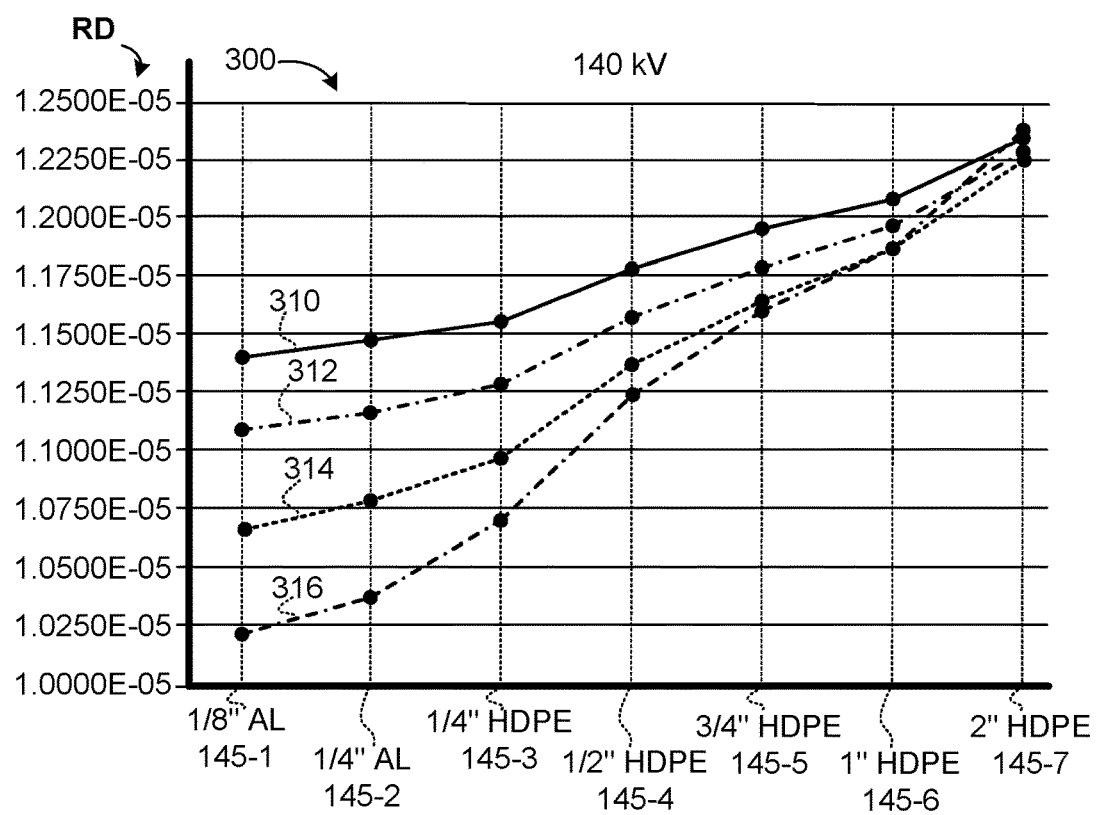
FIG. 3B is a graph illustrating radiation doses delivered to respective exposure regions of a target material having a second physical arrangement relative to the primary radiation.

Graph 300 of FIG. 3B illustrates improvements yielded by scattering medium 140B having respective scattering medium configurations 145-1 through 145-7. Plot line 310 shows RD delivered to layer 330A (the MAX region 131), plot line 312 shows RD delivered to layer 330B, plot line 314 shows RD delivered to layer 330C, and plot line 316 shows RD delivered to layer 330D (the MIN region 139). Performance improvements yielded by respective scattering medium configurations 145-1 through 145-7 for the scattering medium 140B of the irradiation device 100B are listed in Table 2 below.

TABLE 2

| Radiation Energy: 140 keV | | Target Characteristics 135C: 2 inches deep | | | |
|---|---|---|---|---|---|
| Mtrl & Thck 145 | Mtrl 142 | Thickness 146 (inches/cm) | ΔRDR | ΔRD | ΔIRT |
| None | None | None | 16% | 0% | 0% |
| 145-1 | AL | 0.125 in/0.32 cm | 12% | 5% | 9% |
| 145-2 | AL | 0.25 in/0.61 cm | 10% | 6% | 12% |
| 145-3 | HDPE | 0.25 in/0.62 cm | 9% | 7% | 14% |
| 145-4 | HDPE | 0.50 in/1.27 cm | 6% | 9% | 19% |
| 145-5 | HDPE | 0.75 in/1.9 cm | 5% | 10% | 22% |
| 145-6 | HDPE | 1.0 in/2.54 cm | 3% | 11% | 24% |
| 145-7 | HDPE | 2.0 in/5.08 cm | 1% | 14% | 29% |

As illustrated, a scattering medium 140B having scattering medium configuration 145-7 (HDPE having thickness 146 of 2 in/5.08 cm) reduces ΔRDR from about 15% to only about 1% and improves the total RD delivered to the target material 130 by about 14% as compared to an irradiation device 100 without suitably configured scattering media 140. Therefore, a scattering medium 140B configured per scattering medium configuration 145-7 may reduce the irradiation time for target material 130B having target characteristics 135B by about 28% as compared to over-radiation (15% due to reduced ΔRDR and 14% due to ΔRD). Although the shallower configuration of the target material 130B results in decreased irradiation time, the second target characteristics 135B may also result in decreased throughput, since the irradiation device 100B only processes about half the amount of target material 130B in each irradiation operation or batch as compared to the FIG. 2A example.

As used herein, a suitable scattering medium configuration 145, may refer to physical characteristics that enable a scattering medium 140 to improve aspects of irradiation performance, such as: a) reducing the ΔRDR of a target 130 to 10% or less, b) increasing the RDR of the target 130 by 10% or more, c) reducing irradiation time by 10% or more (an ΔIRT of 10% or more), or the like. As illustrated in Tables 1 and 2 above, scattering medium configurations 145-2 through 145-7 may be suitable for irradiation devices 100A and 100B. More specifically, the scattering medium configurations 145-2 through 145-7 may produce scattering media 140A capable of improving irradiation of target 130A by irradiation device 100A and/or scattering media 140B capable of improving irradiation of target 130B by irradiation device 100B.

In implementations involving primary radiation 120 at about 40 keV and above, the material composition 142 of the scattering medium 140A and/or 140B may comprise one or more of Aluminum (AL) and high-density polyethylene (HDPE) in a thickness 146 of at least 3 mm (0.3 cm) or 0.25 in (about 0.62 cm). In implementations involving primary radiation 120 having a high energy range of about 225 keV, the thickness 146 of the scattering media 140A and/or 140B may be between about 2 inches and about 4 inches (between about 5 to 10 cm), In implementations involving primary radiation 120 at higher energies, the thickness 146 of the scattering media 140A and/or 140B may be increased (due to increased penetration). For example, in implementations involving radiation energies up to 600 keV and higher, the point of diminishing returns for increased thickness 146 may be greater than about 2 to 4 inches (e.g., may be about 2.5 to 4.5 inches, 3 to 5 inches, 4 to 6 inches, or the like).

FIG. 4A illustrates another example of an irradiation device 100C. The target 130C may be receive a non-uniform dose of the primary radiation 120 (per target characteristics 135C). As illustrated in graph 401 of FIG. 4B, the intensity of the primary radiation 120 may decrease during penetration through the target 130C (e.g., due to attenuation, absorption, and/or the like). In graph 401 the vertical axis corresponds an intensity of the primary radiation 120 ($I_P$) (e.g., in terms of counts per second (CPS), electromagnetic radiation per unit area, or the like) and the horizontal axis corresponds to penetration through the target 130C. As illustrated, the intensity of the primary radiation 120 ($I_P$) may decay from a maximum value (MAX) to a minimum value (MIN), e.g., may decay by $\Delta I_P$. The non-uniform irradiation of the target 130C may be represented and/or modeled by a MAX region 131 and a MIN region 139, as disclosed herein.

Target non-uniformity may adversely impact irradiation operations. Graph 403A of FIG. 4C illustrates adverse impacts of non-uniform irradiation of the target 130C by an irradiation device 100 that does not include scattering medium 140 having a suitable scattering medium configuration 145. The vertical axis corresponds to radiation dose (RD) in terms of Gray (Gy), or another suitable measure (e.g., absorption of one joule of radiation energy per kilogram of target material 130C) and the horizontal axis corresponds to time (T) (e.g., irradiation time). Plot line L31A shows RD delivered to the MAX region 131 of the target 130A and plot line L39A shows RD delivered to the MIN region 139 as a function of irradiation time.

As illustrated in graph 403A, the rate at which RD is delivered by the primary radiation 120 differs between the MAX region 131 and the MIN region 139. More specifically, the radiation dose rate (RDR, where RDR=$\Delta$RD/$\Delta$T) of the MAX region 131 is greater than the RDR of the MIN region 139 by $\Delta RDR_A$. The $\Delta$RDR of a target 130 may quantify the degree of non-uniformity exhibited by the target 130A (per the target characteristics 135A thereof); higher values of $\Delta$RDR are characteristic of higher degrees of non-uniformity and lower values are characteristic of lower degrees of non-uniformity. In the FIG. 4C example, $\Delta RDR_A$ of the target 130A may be 20% or more, where $$RDR_{MAX} = \Delta RD_{MAX/\Delta T} \text{ or } \Delta RD_{L31A/\Delta T},$$

$$RDR_{MIN} = \Delta RD_{MIN/\Delta T} \text{ or } \Delta RD_{L39A/\Delta T}, \text{ and}$$

$$\Delta RDR_A = \frac{RDR_{MAX} - RDR_{MIN}}{RDR_{MAX}} 100.$$

The disclosure is not limited in regard, however, and may be utilized with targets 130 having any suitable target characteristics 135 and exhibit any degree of non-uniformity.

Although examples of intensity decay, RD, and RDR are described as being substantially linear (e.g., $RDR_{MAX}$ and $RDR_{MIN}$ are modeled as slopes of L31A and L39A, respectively), the disclosure is not limited in this regard and could be adapted to represent and/or model target non-uniformity (e.g., $I_P$ decay, RD, RDR, and so on) using any suitable mechanism or technique, such as exponential modeling, polynomial modeling, spline modeling, cubic spline modeling, numerical analysis, interpolation, and/or the like. In some implementations, $I_P$ decay, RD, and/or RDR may be determined through testing, experience, simulation, modeling, and/or the like.

As disclosed herein, target non-uniformity may adversely impact irradiation operations. For example, an irradiation operation may involve delivering a threshold radiation dose to the target 130C. As illustrated in graph 403A, the MAX region 131 of the target 130C may reach the threshold radiation dose at time $t_{1A}$. By contrast, the MIN region 139 may not reach the threshold radiation dose until $t_{2A}$, e.g., increasing the irradiation time ($IRT_A$) by $\Delta T_A$, where $\Delta T_A = t_{1A} - t_{2A}$. Increasing the irradiation time, however, may result in over-irradiation of some portions of the target 130, such as the MAX region 131, which may a) damage portions of the target 130C, b) degrade portions of the target 130C (e.g., destroy portions of the target 130C, breakdown portions of the target 130C, or the like), c) increase overall irradiation time, d) decrease throughput, e) increase wear on the source 110C, f) increase power consumption, and so on. Alternatively, an irradiation device 100 may attempt to normalize the RD delivered to the target 130 through physical manipulation. For example, an irradiation device 100 may comprise means for rotating, cycling, agitating, or otherwise changing the orientation of the target 130 relative to the primary radiation 120 (physical manipulation means not shown in FIG. 4A to avoid obscuring details of the illustrated examples). Physical manipulation can also have substantial disadvantages, such as a) increased mechanical complexity, b) higher manufacturing and maintenance costs, c) increased power consumption, d) lower assurance (due to randomness in the physical manipulation), e) damage to the target 130C, and so on.

The scattering medium 140C of the irradiation device 100C may be configured to improve aspects of irradiation performance, as disclosed herein. The scattering medium 140C may be configured to produce secondary radiation 160 in response to the primary radiation 120. The secondary radiation 160 may be produced through interactions involving the scattering medium 140C, the primary radiation 120, secondary fluorescence, charged particles of the target 130C, and/or the like. In some embodiments, the secondary radiation 160 may be produced through the Compton effect and/or through Compton scattering, which is the scattering of photons by the primary radiation 120 and/or charged particles of the target 130C within the scattering medium 140C. At least a portion of the energy involved in such scatter interactions may be transferred to recoiling particles, resulting in the emission of secondary radiation 160. The secondary radiation 160 may be emitted at same (or similar) energies as the primary radiation 120. In some embodiments, the secondary radiation 160 may have a lower intensity, as disclosed in further detail herein. The primary radiation 120 may, therefore, comprise and/or be referred to as first, source, active, or generated radiation and the secondary radiation 160 may comprise and/or be referred to as second, responsive, passive, or scatter radiation.

As illustrated in FIG. 4A, in some implementations, a suitable (or optimal) configuration for the scattering medium 140C may be determined based on irradiation characteristics 405C of the irradiation device 100C. As used herein, irradiation characteristics 405 may refer to any information pertaining to an irradiation device 100 and/or irradiation operation implemented by the irradiation device 100 including, but not limited to: characteristics of the source 110 of the irradiation device 100 (e.g., an emission spectrum and/or emission range of the source 110), propagation direction(s) 124 of the primary radiation 120 emitted by the source 110, characteristics of the primary radiation 120 generated by the source 110 (e.g., an energy, energy range, radiation spectrum, or the like), characteristics of the primary radiation 120 utilized in respective irradiation operations implemented by the irradiation device 100, and/or the like. In some embodiments, irradiation characteristics 405 may further comprise information pertaining to target(s) 130 (and/or target material 130) to be irradiated by the irradiation device 100. For example, the irradiation characteristics 405 may comprise one or more target characteristics 135, as disclosed herein.

Suitable (or optimal) scattering medium configurations 145 for scattering media 140 may be determined based, at least in part, on irradiation characteristics 405 specifying conditions under which the scattering media 140 are to be used. In some embodiments, suitable (or optimal) scattering medium configurations 145 may be determined by configuration logic 410, as illustrated in FIG. 4D. The configuration logic 410 may comprise any suitable means for deriving scattering medium configurations 145 from irradiation characteristics 405 including, but not limited to: predetermined rules, predetermined criteria, computer-implemented rules, computer-executable instructions stored on a non-transitory storage medium, logic, logic circuitry, programmable logic, programmable logic circuitry, and/or the like. As disclosed in further detail herein, the configuration logic 410 may be adapted to derive a scattering medium configuration 145 from specified irradiation characteristics 405, the scattering medium configuration 145 determining a material composition 142, physical configuration 144, thickness 146, and/or other properties of the scattering medium 140.

In the FIG. 4A example, a suitable (or optimal) scattering medium configuration 145C for the scattering medium 140C may be determined based on irradiation characteristics 405C of the irradiation device 100C. The scattering medium 140C may, therefore, be targeted to the irradiation device 100C or, more specifically, characteristics of the primary radiation 120 emitted by the source 110C of the irradiation device 100C. Alternatively, or in addition, the scattering medium 140C may be targeted to a specified irradiation operation implemented by the irradiation device 100C (e.g., an irradiation operation involving primary radiation 120 having specified characteristics).

As disclosed herein, the material composition 142 of a scattering medium 140 may refer to atomic numbers (Z) of one or more material(s) comprising the scattering medium 140. The atomic numbers (Z) may be selected based, at least in part, on a Compton scatter interaction distribution. The material(s) comprising the scattering medium 140 may be further configured to be resistant to the primary radiation 120 (e.g., be resistant to radiation at energy level(s) and/or within the energy range of the primary radiation 120).

Figure 5B:
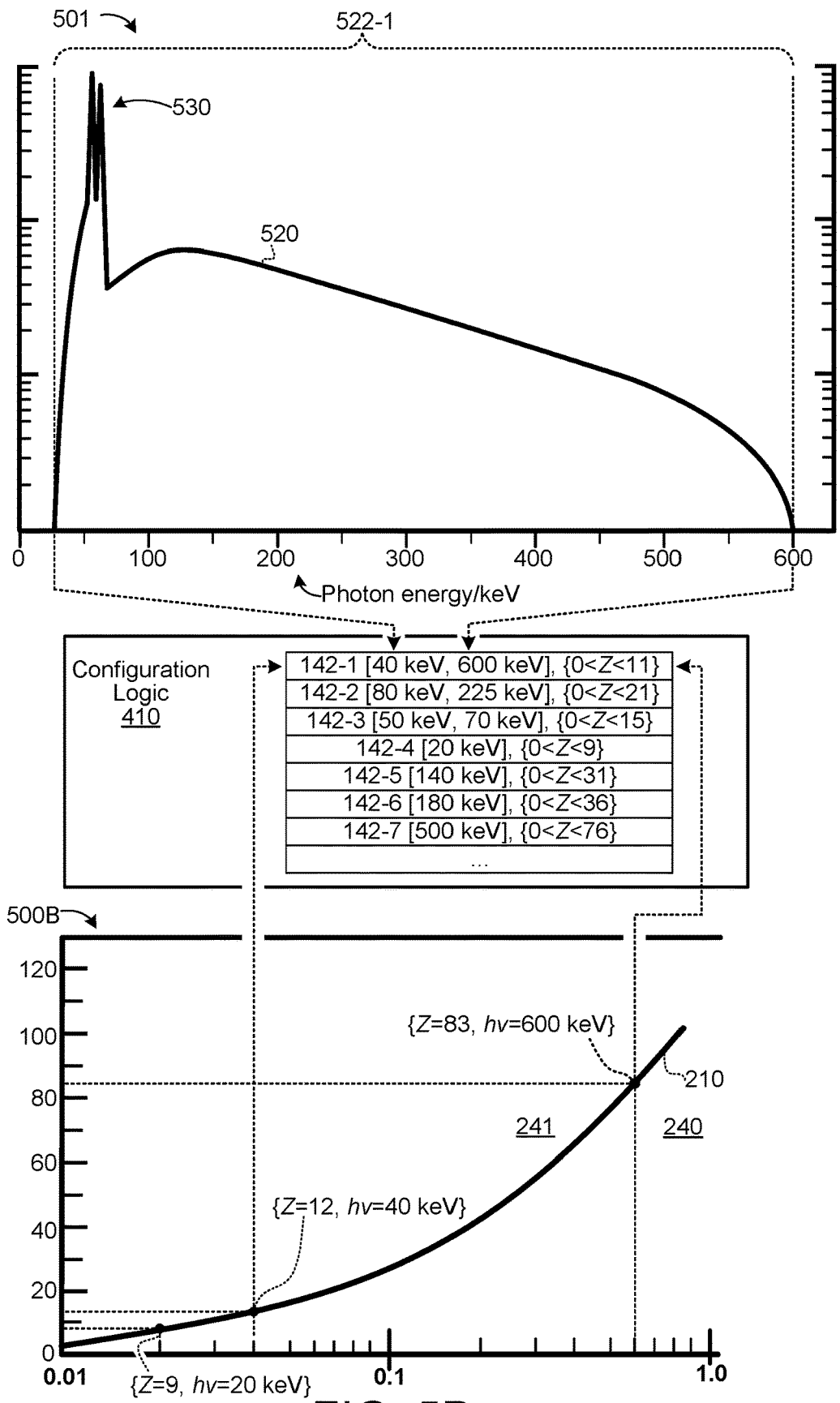

FIGS. 5A-5F illustrate examples of Compton scatter interaction distributions. Graph 500A of FIG. 5A illustrates an example of a Compton scatter interaction distribution, including predetermined computer- and/or logic-implemented rules for determining suitable (or optimal) material compositions 142 for specified radiation energy level(s) 521 and/or specified radiation energy range(s) 522. In graph 500A, the vertical axis corresponds to atomic number (Z) and the horizontal axis corresponds to radiation energy (hv in megaelectron volts (MeV) on a logarithmic scale).

The plot line 510 corresponds to conditions at which Compton scattering ($\sigma$) and photoelectric absorption ($\tau$) are substantially equivalent. In other words, plot line 510 identifies atomic numbers (Z) of materials that exhibit substantially equivalent Compton scattering ($\sigma$) and photoelectric absorption ($\tau$) in response to primary radiation 120 at respective energies; e.g., Z and hv where $\sigma=\tau$ or $|\tau-\tau|<a$ scatter-absorption threshold. The plot line 510 may, therefore, be referred to as the photoelectric absorption plot line 510 (or absorption plot line 510).

The plot line 512 shows conditions where Compton scattering ($\sigma$) and pair production (k) are substantially equivalent (e.g., $\sigma=k$, or $|\sigma-k|<a$ threshold, such as a scatter-pair production threshold). Pair production refers to an interaction in which a photon creates an electron-positron pair rather than secondary radiation 160, e.g., interactions between photons of the primary radiation 120 (and/or secondary fluorescence) and nuclei of the material of atomic number (Z). The plot line 512 may, therefore, be referred to as the pair-production plot line 512.

As illustrated in FIG. 5A, the plot lines 510 and 512 may define a scatter region 540 in which Compton scattering ($\sigma$) is dominant over photoelectric absorption ($\tau$) and pair production (k). The scatter region 540 may be distinguished from region 541 in which photoelectric absorption ($\tau$) is dominant and region 543 in which pair production (k) is dominant. In some embodiments, configuration logic 410 may be configured to determine suitable (or optimal) material compositions 142 for scattering media 140 based on correlational relationships between the atomic number(s) (Z) of respective materials and radiation energy, Compton scattering ($\sigma$), photoelectric absorption ($\tau$), and/or pair production (k). More specifically, suitable (or optimal) atomic numbers (2) for a material composition 142 for a scattering medium 140 to be utilized with primary radiation 120 at a specified energy level 521 and/or energy range 522 may be selected from atomic number(s) (Z) that fall within the scatter region 540 for the specified energy level 521 and/or energy range 522. Determining a suitable (or optimal) material composition 142 for a specified energy level 521 may comprise selecting atomic number(s) (Z) that fall within the scatter region 540 at the specified energy level 521, determining a suitable (or optimal) material composition 142 for a specified energy range 522 may comprise selecting atomic number(s) (Z) that fall within the scatter region 540 for energies within the specified energy range 522, and so on. As shown in FIG. 5A, Compton scattering ($\sigma$) may be limited by photoelectric absorption ($\tau$) at low energies (i.e., less than or equal to 1 MeV) and Compton scattering ($\sigma$) may be limited by pair production (k) at high energies (i.e., greater than 1 MeV) for various scattering media 140.

Referring to FIG. 5B, in some embodiments, the material composition 142 for a scattering medium 140 of an irradiation device 100 may be determined based on an energy composition 520 of the primary radiation 120 produced by the source 110 of the irradiation device 100 (as specified by irradiation characteristics 405 of the irradiation device 100). As used herein, an energy composition 520 may refer to any suitable energy-related characteristic of primary radiation 120 and/or a source 110, including, but not limited to, an energy of the primary radiation 120, an energy level 521, an energy range 522, a radiation spectrum, an emission spectrum, a Bremsstrahlung x-ray spectrum, and/or the like. As illustrated in FIG. 5B, the material composition 142-1 determined per the energy composition 520 may include material(s) having atomic number(s) (Z) that fall within the scatter region 540 for at least a portion of the energy composition 520 of the primary radiation 120.

FIG. 5B illustrates further examples of mechanisms for determining suitable (or optimal) material compositions 142 for scattering media 140. Graph 501 of FIG. 5B illustrates an energy composition 520 of primary radiation 120 emitted by a source 110 of an irradiation device 100, such as a Bremsstrahlung x-ray spectrum or the like. In graph 501, the vertical axis corresponds to relative radiation intensity at respective energies in a logarithmic scale (e.g., in terms of CPS or the like). The horizontal axis corresponds to radiation energy in kiloelectron volts (keV). In the FIG. 2B example, the source 110 may comprise a 600 kV x-ray tube spanning an energy range 522-1 from 40 keV to 600 keV. As illustrated, the source 110 may emit characteristic radiation 530, which may correspond to the target material utilized by the source 110, such as Tungsten or the like.

As illustrated in FIG. 5B, a suitable (or optimal) material composition 142-1 for the energy composition 520 may be determined based on intersections between a specified energy range 522-1 and plot lines 510 and/or 512 of the Compton scatter interaction distribution illustrated in graph 500B. More specifically, the material composition 142-1 may include material(s) having atomic number(s) (Z) that fall within the scatter region 540 of the Compton scatter interaction distribution across the energy range 522-1 (from 40 keV to 600 keV). In graph 500B, 40 keV intersects plot line 510 at about Z=12 and 600 keV intersects plot line 510 at about Z=83 (energies above about 1 MeV are omitted from graph 500B to avoid obscuring details of the illustrated example). Determining a suitable (or optimal) material composition 142-1 may comprise identifying: a) a first atomic number (Z=12) at which Compton scattering (σ) is equivalent to photoelectric absorption (τ) at the low-end of the energy range 522-1 (40 keV) and b) a second atomic number (Z=83) at which Compton scattering (σ) is equivalent to photoelectric absorption (τ) at the high-end of the energy range 522-1 (600 keV). The upper bound for the material composition 142-1 may be the lower of the first and second Z values, or set below the lower of the first and second Z values within the scattering region 540 (e.g., Z=11 rather than Z=82). The material composition 142-1 may, therefore, comprise material(s) having atomic number(s) (Z), where $1 \leq Z \leq 11$ (e.g., Z may be limited by the low-end of the energy range 522-1).

Suitable (or optimal) material compositions 142 may be determined for other energy ranges 522 using similar logic (e.g., configuration logic 410). For example, a material composition 142-2 may be targeted to a subset of the energy range 522-1, such as 80 keV to 225 keV, resulting in a material composition 142-2 having an upper bound for Z at 20 (based on a Z value of about 21 at 80 keV on the photoelectric absorption plot line 510). In another example, a material composition 142-3 may be configured to cover the characteristic radiation 530 of the energy composition 520 (from 50 keV to about 70 keV) resulting in an upper bound for Z at 14 (based on a Z value of about 15 at 50 keV on plot line 510), and so on.

In some implementations, suitable (or optimal) material compositions 142 may be determined for specified energy levels 521 (per the configuration logic 410, or other mechanism). For example, a material composition 142-4 adapted for primary radiation 120 at 20 keV may include $1 \leq Z \leq 8$ (since Z is about 9 on the photoelectric absorption plot line 510 at 20 keV), a material composition 142-5 configured for primary radiation 120 at 140 keV may include $1 \leq Z \leq 30$, a material composition 142-6 adapted for primary radiation 120 at 180 keV may include $1 \leq Z \leq 35$, a material composition 142-7 adapted for primary radiation 120 at 500 keV may include $1 \leq Z \leq 76$, and so on.

Figure 5C:
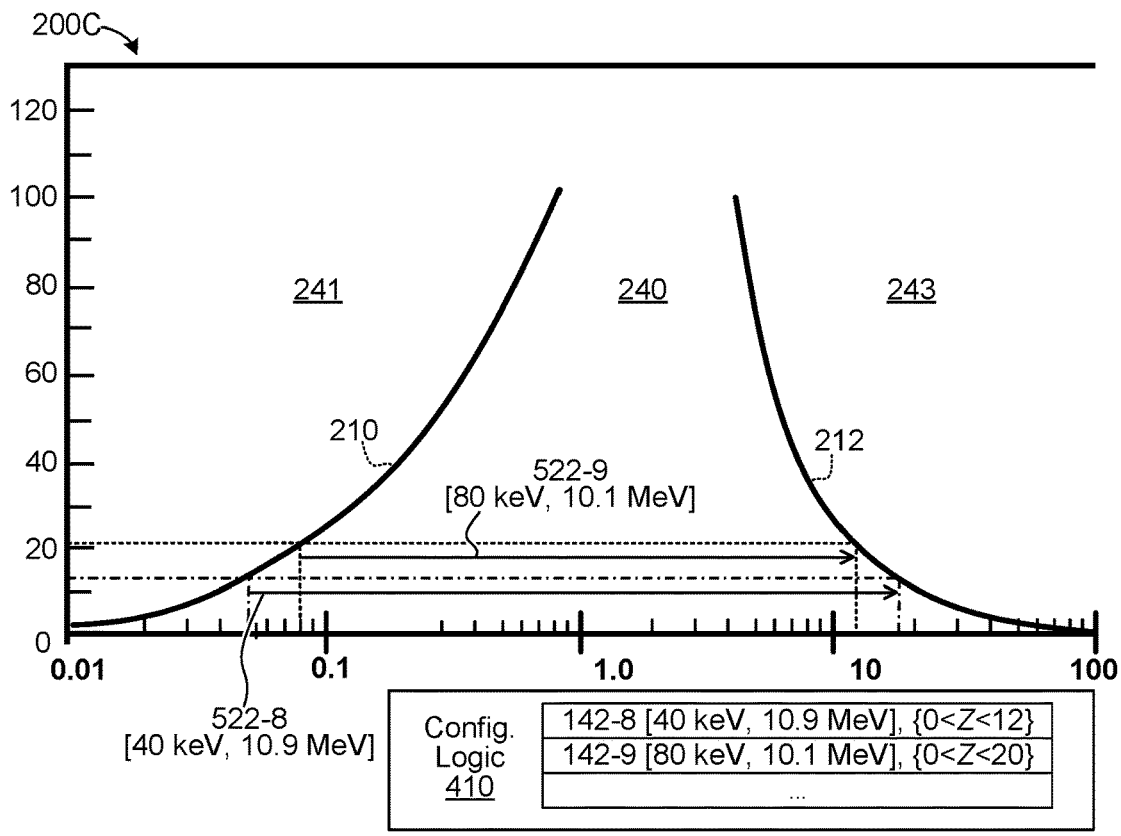

FIG. 5C illustrates further examples of techniques for determining suitable (or optimal) material compositions 142 for scattering media 140 (e.g., for examples of configuration logic 410). In the FIG. 5C example, the material composition 142-8 may be configured for the low-end of the energy range 522-8 (40 keV, corresponding to about Z=11 on plot line 510, as illustrated in graph 500C). The upper-end of the energy range 522-8 may be limited by an intersection between Z=11 and the pair-production plot line 512, e.g., where Compton scattering (σ) is equivalent to pair production (k). The intersection between Z=11 and plot line 512 is at about 10.9 MeV; therefore, the material composition 142-8 may be suitable (or optimal) for primary radiation 120 comprising energies from 40 keV up to 10.9 MeV or [40 keV, 10.9 MeV]. At energies at or above 10.9 MeV, material compositions 142 may be limited by the pair-production plot line 512 and atomic number (Z). In another example, a suitable (or optimal) material composition 142-9 may be configured for the low-end of the energy range 522-9 (80 keV, corresponding to about Z=21 on plot line 510). The upper end of the energy range 522-9 may be limited by an intersection between Z=21 and plot line 512, which, as illustrated in graph 500C is at about 10.9 MeV. Therefore, the material composition 142-9 may be suitable (or optimal) for primary radiation 120 comprising energies from 80 keV up to 10.1 MeV or [40 keV, 10.1 MeV]. At energies above 10.9 MeV, the atomic number (Z) may be limited by intersections with the pair-production plot line 512.

Figure 5D:
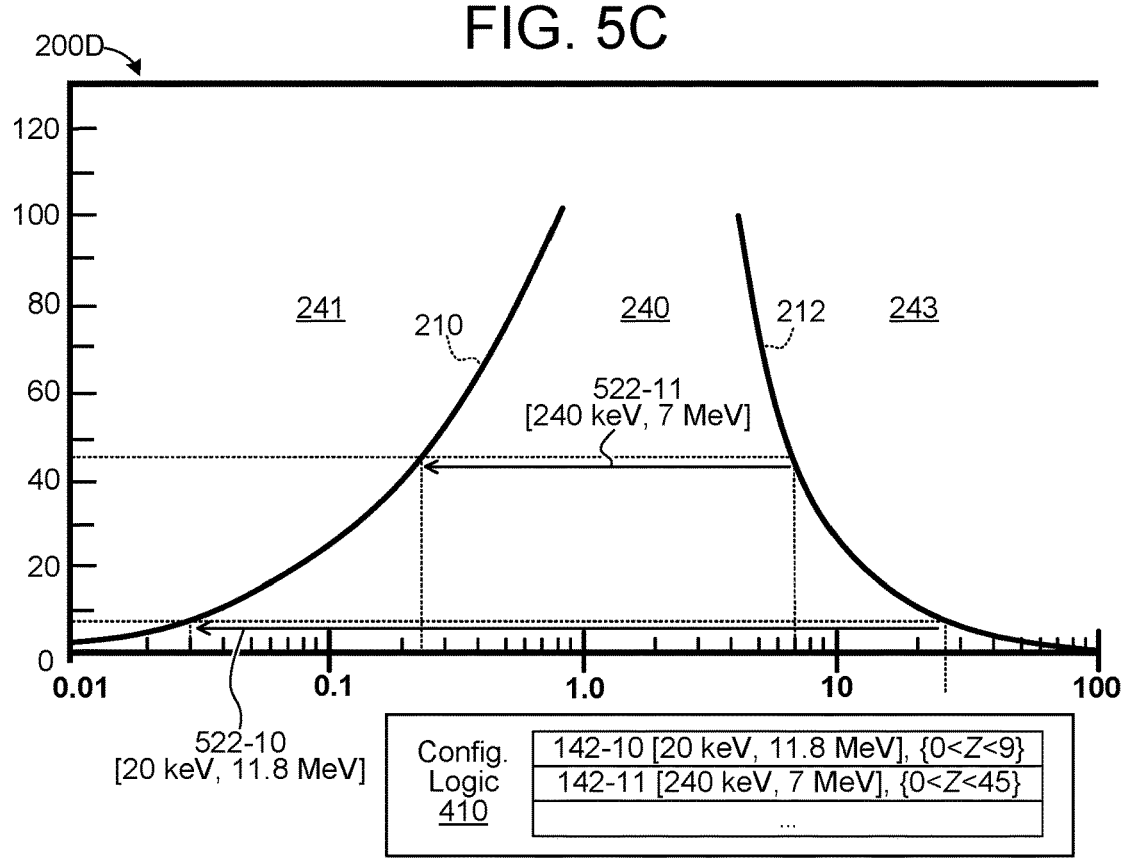

In the FIG. 5D illustrates further examples of techniques for determining suitable (or optimal) material compositions 142 (e.g., further examples, of configuration logic 410). In the FIG. 5D example, the material composition 142-10 may be configured for the high end of the energy range 522-10 (11.8 MeV, corresponding to about Z=9 on the pair-production plot line 512). The low end of the energy range 522-10 may be limited by an intersection between Z=9 and the photoelectric absorption plot line 510, which is at about 20 keV, as illustrated in graph 500D. Therefore, the material composition 142-10 may be suitable (or optimal) for primary radiation 120 comprising energies from 11.8 MeV down to 20 keV or [20 keV, 11.8 MeV]. At energies at or below 20 keV, Z may be limited by the photoelectric absorption plot line 510. In another example, a suitable (or optimal) material composition 142-11 may be targeted to the high end of the energy range 522-11 (7 MeV), which may intersect with the pair-production plot line 512 at about Z=45. As illustrated, the low end of the energy range 522-11 may be limited by the intersection between Z=45 and the photoelectric absorption plot line 510, at about 240 keV. The material composition 142-11 may, therefore, be suitable (or optimal) for primary radiation 120 comprising energies from 7 MeV down to 240 keV.

Table 3 lists examples of suitable (or optimal) material compositions 142 for scattering media 140 to be utilized with primary radiation 120 at specified energy level(s) 521 and/or within specified energy ranges 522, as illustrated in FIGS. 5A-5D.

TABLE 3

| Radiation energy | Atomic Number (Z) Range |
|---|---|
| 20 keV | $1 \leq Z \leq 8$ |
| [20 keV, 11.8 MeV] | $1 \leq Z \leq 8$ |
| 40 keV | $1 \leq Z \leq 11$ |
| [40 keV, 600 keV] | $1 \leq Z \leq 11$ |
| [40 keV, 10.9 MeV] | $1 \leq Z \leq 11$ |
| 50 keV | $1 \leq Z \leq 14$ |
| [50 keV, 70 keV] | $1 \leq Z \leq 14$ |
| 70 keV | $1 \leq Z \leq 19$ |
| 80 keV | $1 \leq Z \leq 20$ |
| [80 keV, 225 keV] | $1 \leq Z \leq 20$ |
| [80 keV, 10.1 MeV] | $1 \leq Z \leq 20$ |
| 140 keV | $1 \leq Z \leq 30$ |
| 180 keV | $1 \leq Z \leq 35$ |
| 225 keV | $1 \leq Z \leq 43$ |
| 240 keV | $1 \leq Z \leq 44$ |
| [240 keV, 7 MeV] | $1 \leq Z \leq 44$ |
| 500 keV | $1 \leq Z \leq 76$ |
| 600 keV | $1 \leq Z \leq 82$ |
| 7 MeV | $1 \leq Z \leq 20$ |
| 10.1 MeV | $1 \leq Z \leq 20$ |
| 10.9 MeV | $1 \leq Z \leq 11$ |
| 11.8 MeV | $1 \leq Z \leq 8$ |

Material compositions 142 including atomic number(s) Z≤8 may include one or more of a carbon-based material, polymer, organic polymer, plastic, plastic polymer, synthetic polymer, thermoplastic, thermoplastic polymer, nylon, polyvinyl chloride (PVC), polystyrene, polyoxymethylene (POM), acetal, acetal resin, an acetal plastic, polyacetal, polyformaldehyde, HDPE, and/or the like. Material compositions 142 that include atomic number(s) Z≤13 may further include one or more of aluminum, an aluminum alloy, and/or the like. In some implementations, the material composition 142 determined for a scattering medium 140 may specify a selected material (e.g., the scattering medium 140 may be substantially comprised of a selected material type, such as HDPE). Alternatively, the material composition 142 may comprise a plurality of materials. The material(s) selected for scattering medium 140 adapted for use with respective types of primary radiation 120 may be further configured to be resistant to the respective types of primary radiation 120.

Although FIGS. 5A-D and Table 3 describe specific examples of suitable (or optimal) material compositions 142 for specified energy compositions 520, energy levels 521 and/or energy ranges 522, the disclosure is not limited in this regard and could be adapted to determine suitable (or optimal) material compositions 142 for scattering media 140 to be utilized with primary radiation 120 having any suitable energy composition 520, energy level 521, and/or energy range 522. Moreover, in some implementations, a material composition 142 may include material(s) having atomic number (Z) on or within a threshold of the photoelectric plot line 510 and/or the pair-production plot line 512. In other words, the material composition 142 determined for an energy range 522 may include material(s) having atomic number(s) (Z) that fall within region 241 or 243 for at least a portion of the energy range 522 (and/or are within a threshold distance from the scattering region 540 across the energy range 522). The threshold (e.g., material threshold) may be set according to testing and experience.

In some embodiments, suitable (or optimal) physical configurations 144 for scattering media 140 to be deployed within respective irradiation devices 100 may be determined based, at least in part, on irradiation characteristics 405 of the respective irradiation devices 100. In the FIG. 4A example, the physical configuration 144C of the scattering medium 140C may be determined based on the irradiation characteristics 405C of the irradiation device 100C. The physical configuration 144 of a scattering medium 140 may refer to one or more of a shape of the scattering medium 140, a volume of the scattering medium, dimensions of the scattering medium, an orientation or position of the scattering medium 140 within an irradiation device 100, an orientation or position of the scattering medium 140 relative to the source 110 of the irradiation device, an orientation or position of the scattering medium 140 relative to primary radiation 120 emitted by the source 110, an orientation or position of the scattering medium 140 relative to emission direction(s) 124 of the primary radiation 120, an orientation or position of the scattering medium 140 relative to a target 130 of the irradiation device 100, a thickness 146 of the scattering medium 140, and/or the like. As used herein, the thickness 146 of a scattering medium 140 may refer to a measure of a thickness or depth of the scattering medium 140 along a designated measure or axis (e.g., a depth axis or measure, a thickness axis or measure, or the like). In some implementations, the physical configuration 144 of the scattering medium 140 may be configured to align the depth axis of the scattering medium 140 with propagation direction(s) 124 of the primary radiation 120 (e.g., the thickness 146 of the scattering medium 140 may correspond to a measure along respective propagation direction(s) 124). For example, the physical configuration 144 may be configured to align the depth axis of the scattering medium 140 with propagation direction 124 of a central beam of the primary radiation 120. Alternatively, or in addition, the physical configuration 144 may be configured to align the depth axis of the scattering medium 140 with direction(s) in which charged particles produced by the primary radiation 120 penetrate the scattering medium 140 (e.g., to produce Compton scatter interactions and corresponding secondary radiation 160), which may correspond to the propagation direction(s) 124 of the primary radiation 120 relative to the target 130.

In some embodiments, the thickness 146 of the scattering medium 140 may be set at a penetration depth or distance (pd) at which the benefits of increased thickness 146 fall below a threshold (e.g., a point of diminishing returns). For example, the thickness 146 may be set at a penetration distance (pd) at which the scatter cross section ($\sigma_{CS}$) of the scattering medium 140 is projected to be equivalent to and/or exceed the absorption cross section ($\tau_{CS}$) of the scattering medium 140 by at least a threshold (e.g., a scatter-absorption threshold or ratio). As disclosed in further detail herein, the scatter or scattering cross section ($\sigma_{CS}$) of a scattering medium 140 may refer to a total or cumulative amount of secondary radiation 160 produced through scatter interactions during penetration of primary radiation 120, secondary fluorescence, and/or corresponding charged particles of the target 130 through the scattering medium 140 (e.g., through the thickness 146 of the scattering medium 140). The absorption cross section ($\tau_{CS}$) may refer to a total or cumulative photoelectric absorption of the primary radiation 120, secondary fluorescence, charged particles, and/or resulting secondary radiation 160 during penetration into (and out of) the scattering medium 140. The thickness 146 of a scattering medium 140 may be set based, at least in part, on the scattering cross section ($\sigma_{CS}$) of the scattering medium 140 and the absorption cross section ($\tau_{CS}$) of the scattering medium 140. The thickness 146 may be set at a point at which the scattering cross section ($\sigma_{CS}$) of the scattering medium 140 exceeds the absorption cross section ($\tau_{CS}$) of the scattering medium 140 by at least a threshold.

The probability of Compton scatter interactions within the scattering medium 140 may increase as a function of penetration distance (pd). As such, the amount of secondary radiation 160 produced by the scattering medium 140 may increase with increasing thickness 146. For example, the intensity or amount of secondary radiation 160 produced at respective penetration distances (pd) within the scattering medium 140 may be represented as $f_\sigma$(pd). The total or cumulative Compton scattering ($\sigma$) at respective penetration distances (pd), scattering cross section ($\sigma_{CS}$), may be represented in terms of $f_\sigma$(pd), where $\sigma_{CS}(pd)=\int_{d=0}^{pd} f_\sigma(d)$, such that the scatter cross section ($\sigma_{CS}$) increases with increasing propagation distance (pd), e.g., increasing thickness 146.

The intensity of the secondary radiation 160 produced within the scattering medium 140 may also be a function of the photoelectric absorption ($\tau$) of the scattering medium 140. Photoelectric absorption ($\tau$) may also increase as a function of penetration distance (pd). However, in contrast to Compton scattering ($\sigma$), photoelectric absorption ($\tau$) may act to reduce the amount and/or intensity of the secondary radiation 160 emitted by the scattering medium 140. In some implementations, photoelectric absorption ($\tau$) at respective propagation distances (pd) within the scattering medium 140 may be represented as $f_\tau$(pd), and the total or cumulative photoelectric absorption ($\tau$) of the scattering medium 140, the absorption cross section ($\tau_{CS}$), may be represented as $\tau_{CS}(pd)=\int_{d=0}^{pd} f_\tau(d)$. Therefore, the absorption cross section ($\tau_{CS}$) of the scattering medium 140 may also increase with increasing thickness 146 (resulting in corresponding decreases to the amount or intensity of the secondary radiation 160 produced by the scattering medium 140).

As illustrated above, both the scattering cross section ($\sigma_{CS}$) and the absorption cross section ($\tau_{CS}$) of a scattering medium 140 may increase with increasing thickness 146. Increases to the scattering cross section ($\sigma_{CS}$) of the scattering medium 140 may increase the amount and/or intensity of the secondary radiation 160 produced by the scattering medium 140. However, the absorption cross section ($\tau_{CS}$) of the scattering medium 140 may also increase with increasing thickness 146. The absorption cross section ($\tau_{CS}$) of the scattering medium 140 may reduce (and eventually negate) the benefits of increased thickness 146, e.g., may reduce the amount and/or intensity of secondary radiation 160 produced at increasing penetration distances (pd) within the scattering medium 140.

Figure 6A:
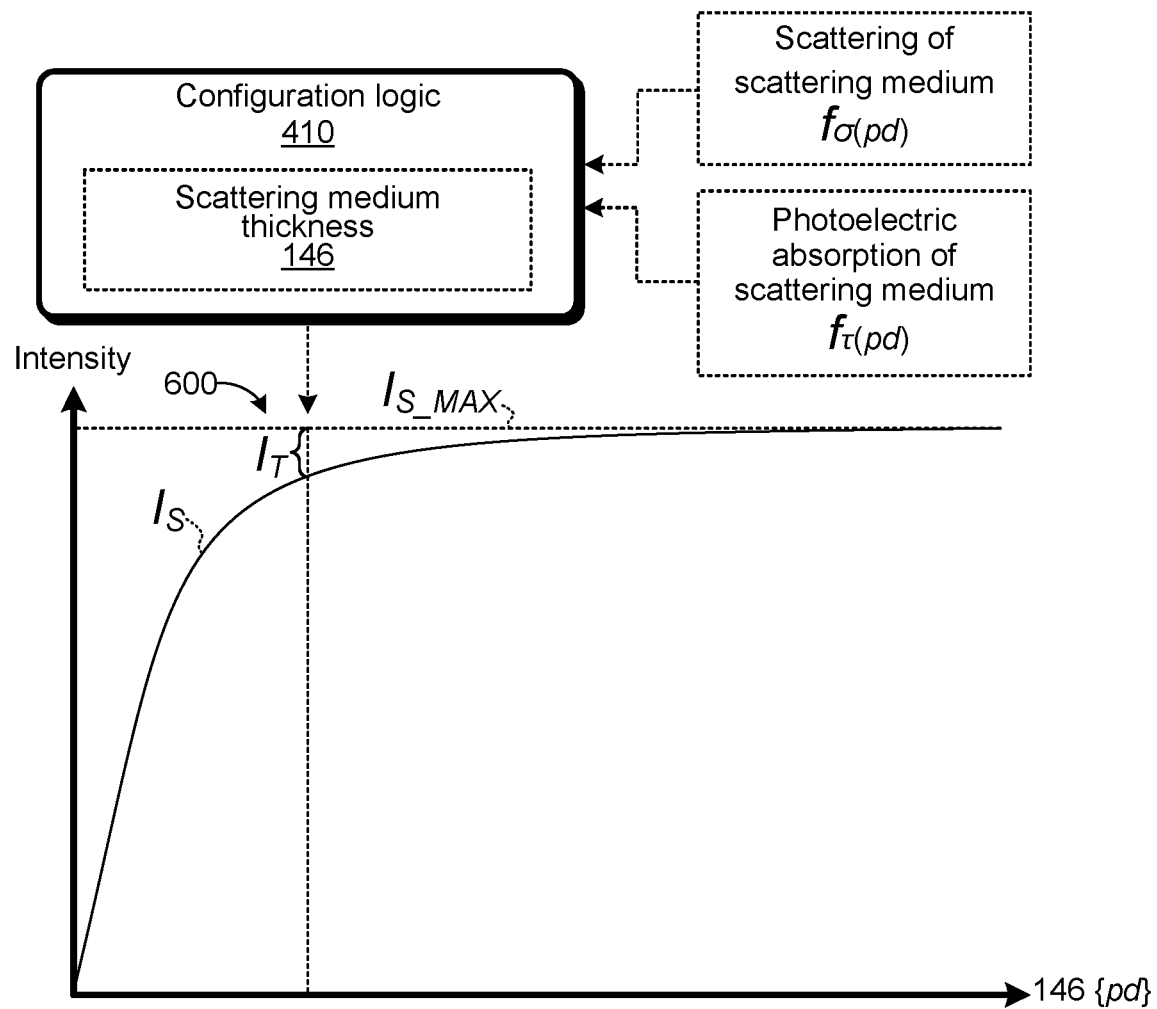
FIG. 6A is a graph illustrating examples of criteria for determining a suitable (or optimal) physical configuration for a scattering medium.

As illustrated in graph 600 of FIG. 6A, the benefits of increased thickness 146 may diminish with increasing thickness 146. In graph 600 the vertical axis represents increasing intensity of the secondary radiation 160 ($I_S$) produced by a scattering medium 140 and the horizontal axis represents increased thickness 146 of the scattering medium 140. As illustrated, the amount and/or intensity of the secondary radiation 140 ($I_S$) may increase quickly at low thicknesses 146 where the scatter cross section ($\sigma_{CS}$) predominates over the absorption cross section ($\tau_{CS}$). The benefits of further increases to thickness 146 may diminish and eventually become negligible at higher thicknesses 146 where the absorption cross section ($\tau_{CS}$) of the scattering medium 140 negates the benefits yielded by increased scatter cross section ($\sigma_{CS}$). In other words, the amount and/or intensity of the secondary radiation 160 produced by scattering media 140 having respective thicknesses 146 may be a function of the scatter cross section ($\sigma_{CS}$) and absorption cross section ($\tau_{CS}$) of the scattering medium 140 at the respective thicknesses 146, e.g., $I_S(pd)=\sigma_{CS}(pd)-\tau_{CS}(pd)$, $I_S(pd)=f_\sigma(pd)-f_\tau(pd)$, $I_S(pd)=\int_{d=0}^{pd} f_\sigma - \int_{d=0}^{pd} f_\tau(d)$, or the like.

In some embodiments, the thickness 146 of a scattering medium 140 may be set at a propagation distance (pd) at which $\sigma_{CS}(pd)=\tau_{CS}(pd)$ or $\sigma_{CS}(pd)-\tau_{CS}(pd)>T_{SA}$, where $T_{SA}$ is a predetermined scatter-absorption threshold, as disclosed herein. Alternatively, or in addition, the thickness 146 of the scattering medium 140 may be set at a propagation distance (pd) at which increases to $I_S$ (if any) fall below a threshold, e.g., a pd at which $f_\sigma(pd)=f_\tau(pd)$ or $f_\sigma(pd)-f_\tau(pd) <T_{SR}$, where $T_{SR}$ is a predetermined scatter-increase rate threshold. In other words, the thickness 146 may be set at a propagation distance (pd) at which Compton scattering ($\sigma$) is equivalent to and/or exceeds photoelectric absorption ($\tau$) by the scatter-increase rate threshold ($T_{SR}$).

In some implementations, the thickness 146 of the scattering medium 140 may be set based on a projected intensity of the secondary radiation 160 ($I_S$). As illustrated in graph 600, the thickness 146 of the scattering medium 140 may be set at a propagation distance (pd) at which the amount and/or intensity of the secondary radiation 160 produced by the scattering medium 140 is projected to be within a threshold ($I_T$) of a maximum intensity value ($I_{S\_MAX}$). The maximum intensity value ($I_{S\_MAX}$) may be proportional to an intensity of the primary radiation 120. In some implementations, the maximum intensity value ($I_{S\_MAX}$) may be determined by testing, experience, simulation, modeling, and/or the like.

As disclosed herein, in some embodiments, the thickness 146 of the scattering medium may be set at a point of diminishing returns. The point of diminishing returns may correspond to a propagation distance (pd) or thickness 146 at which increases to $I_S$ yielded by further increases to thickness 146 fall below a threshold, such as the scatter-increase threshold ($T_{SI}$), as disclosed herein. In the FIG. 6A example, the rate at which $I_S$ increases with thickness 146 may be represented as a scatter increase rate or thickness utility metric (TKU), TKU=$\Delta I_S$/$\Delta$pd or $\Delta I_S$/$\Delta$Thickness 146. The scatter increase (or TKU) at respective propagation depths (pd) may quantify a utility of further increases to thickness 146. As illustrated in FIG. 6A, the scatter increase rate (TKU) may be initially high, but may slow and eventually converge to zero due to increased absorption cross section ($\tau_{CS}$). The thickness 146 of the scattering medium 140 may be set at a point at which the scatter increase rate (or TKU) falls below a threshold, such as the scatter increase threshold ($T_{SI}$), as disclosed herein.

Figure 6B:
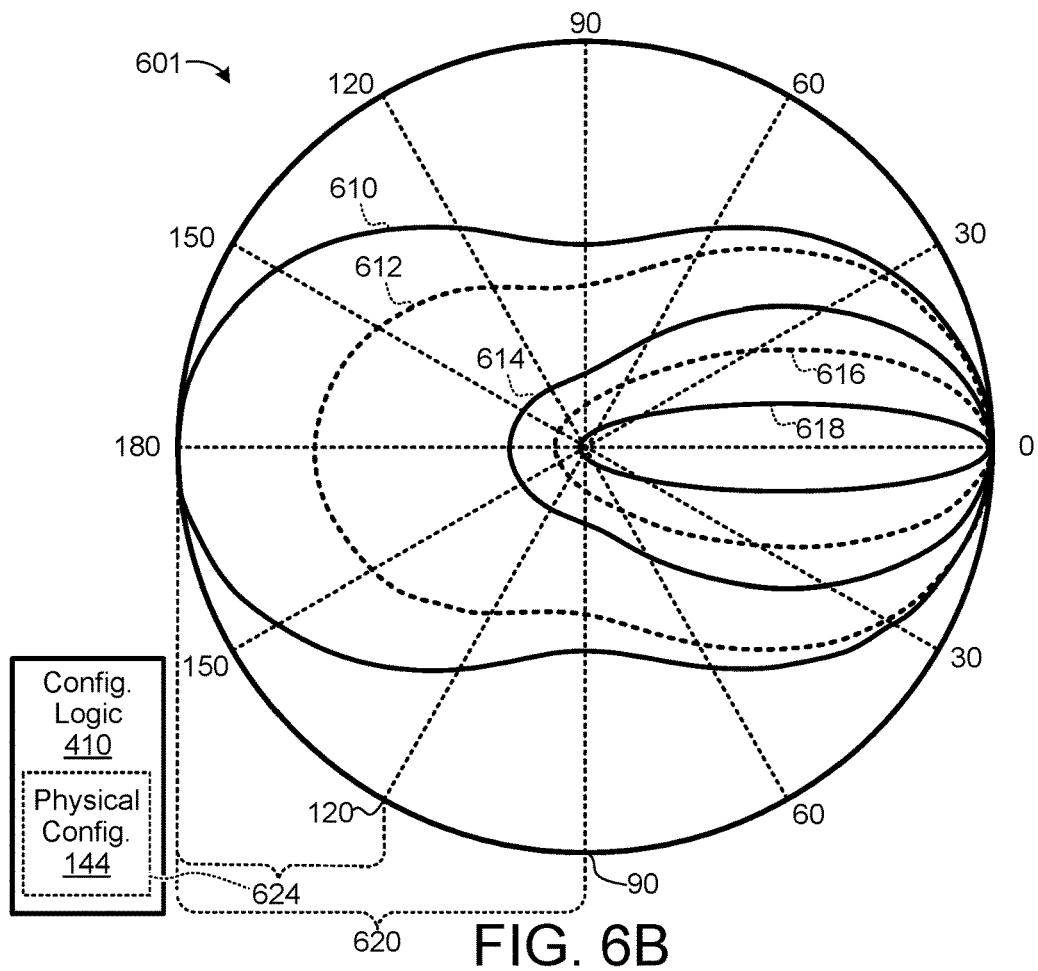
FIG. 6B is a polar graph illustrating scattering-angle cross sections for a range of radiation energies.

The secondary radiation 160 produced by a scattering medium 140 in response to primary radiation 120 may be emitted at respective scatter angles relative to the primary radiation 120 (e.g., relative to the propagation direction 124 of the primary radiation 120). The scattering-angle distribution of the secondary radiation 160 may be a function of the energy composition 520 of the primary radiation 120. FIG. 6B includes a plot 601 illustrating examples of Klein-Nishina scattering-angle distributions (or scattering-angle cross sections) produced by a scattering medium 140 in response to primary radiation 120 at respective energy levels, including 2.75 electron volts (eV) (plot line 610), 60 keV (plot line 612), 511 keV (plot line 614), 1.46 MeV (plot line 616), and 10 MeV (plot line 618).

As illustrated, the scattering medium 140 may produce secondary radiation 160 at and/or within a back-scatter distribution 620, which may comprise a subset of the scattering-angle distribution. The back-scatter distribution 620 may include scatter angles that are offset from the propagation direction 124 of the primary radiation 120 by 90° or more (e.g., scattering angles from about 90° to about 270°). FIG. 6B further illustrates examples of an irradiation distribution 624, which may comprise scatter angles configured to direct secondary radiation 160 towards the target 130. The irradiation distribution 624 may include a subset of the back-scatter distribution 620; the irradiation distribution 624 may comprise scatter angles that are offset from the propagation direction 124 of the primary radiation 120 by about 120° or more (e.g., scattering angles from about 120° to about 240°). The intensity of the secondary radiation 160 emitted within the irradiation distribution 624 may be proportional to the intensity of the primary radiation 120. For example, the maximum intensity of the secondary radiation 160 capable of irradiating at least a portion of the target 130 ($I_{S\_MAX}$) may be expressed as $I_{S\_MAX}=P_e I_P$ or $I_{S\_MAX}=P_e E_P$ where $I_P$ represents the intensity of the primary radiation 120, $E_P$ represents the energy of charged particles produced by the primary radiation 120, and $P_e$ is a scaling factor (or ratio), which may be based on energy level of the primary radiation 120. As illustrated in FIG. 6B, $P_e$ may be inversely proportional to radiation energy; $P_e$ may be greater than ½ at low energies, such as 2.75 eV (410) through 60 keV (412), may decrease to greater than ⅙ at about 511 eV (414), may fall to greater than 1/12 at about 1.46 MeV (416), and may approach negligible values at 10 MeV (418) and above.

In some embodiments, the physical configuration 144 determined for a scattering medium 140 may be configured to align the depth axis (or thickness 146) of the scattering medium 140 with the propagation direction 124 of the primary radiation 120. The alignment between the depth axis and the primary radiation 120 may cause secondary radiation 160 emitted within the irradiation distribution 624. In some implementations, the alignment between the depth axis of the scattering medium 140 and the propagation direction 124 of the primary radiation 120 may be adapted to maximize an amount of secondary radiation 160 capable of irradiating at least a portion of the target 130.

Referring back to FIG. 4A, the scattering medium 140C of the irradiation device 100C may be configured in accordance with the scattering medium configuration 145C. The scattering medium configuration 145C may be determined based on irradiation characteristics 405C of the irradiation device 100C, as disclosed herein. The scattering medium 140C may, therefore, be configured to improve aspects or irradiation performance, as disclosed herein (e.g., decrease ΔRDR to 10% or less, increase RDR by 10% or more, decrease irradiation time by 10% or more, and/or the like).

Graph 103B of FIG. 4E illustrates examples of improvements to irradiation performance produced by a scattering medium 140C having a suitable (or optimal) scattering medium configuration 145C determined in accordance with the irradiation characteristics 405C of the irradiation device 100C. Plot lines L31B and L39B show the RD delivered to the MAX region 131 and MIN region 139 of the target 130C, respectively. As illustrated, the scattering medium 140C may reduce target non-uniformity from $\Delta RDR_A$ (about 20%) down to an $\Delta RDR_{SM}$ of about 3% (reduce ΔRDR by about 17%). Due to emission of the secondary radiation 160 by the scattering medium 140C, the RDR of both the MAX region 131 and MIN region 139 may be increased as compared to graph 103A; the time $t_{1SM}$ at which the MAX region 131 reaches the threshold radiation dose may be about 15% shorter than time $t_{1A}$. Moreover, the irradiation time for the MIN region 139 ($t_{2SM}$ or $IRT_{SM}$) may be about 32% shorter than the irradiation time ($IRT_A$) without the scattering medium 140C, e.g., 17% due to the reduction to ΔRDR and 15% due to increased RDR.

As illustrated above, the scattering medium 140C may reduce the ΔRDR of the target 130 by about 17% and reduce the irradiation time by about 32%. The scattering medium 140 may, therefore, comprise a suitable or suitably-configured scattering medium 140C (e.g., a scattering medium 140 that reduces ΔRDR to 10% or less, decreases irradiation time by 10% or more, increases RDR by 10% or more, increases RD by 10% or more, and/or the like).

Figure 7:
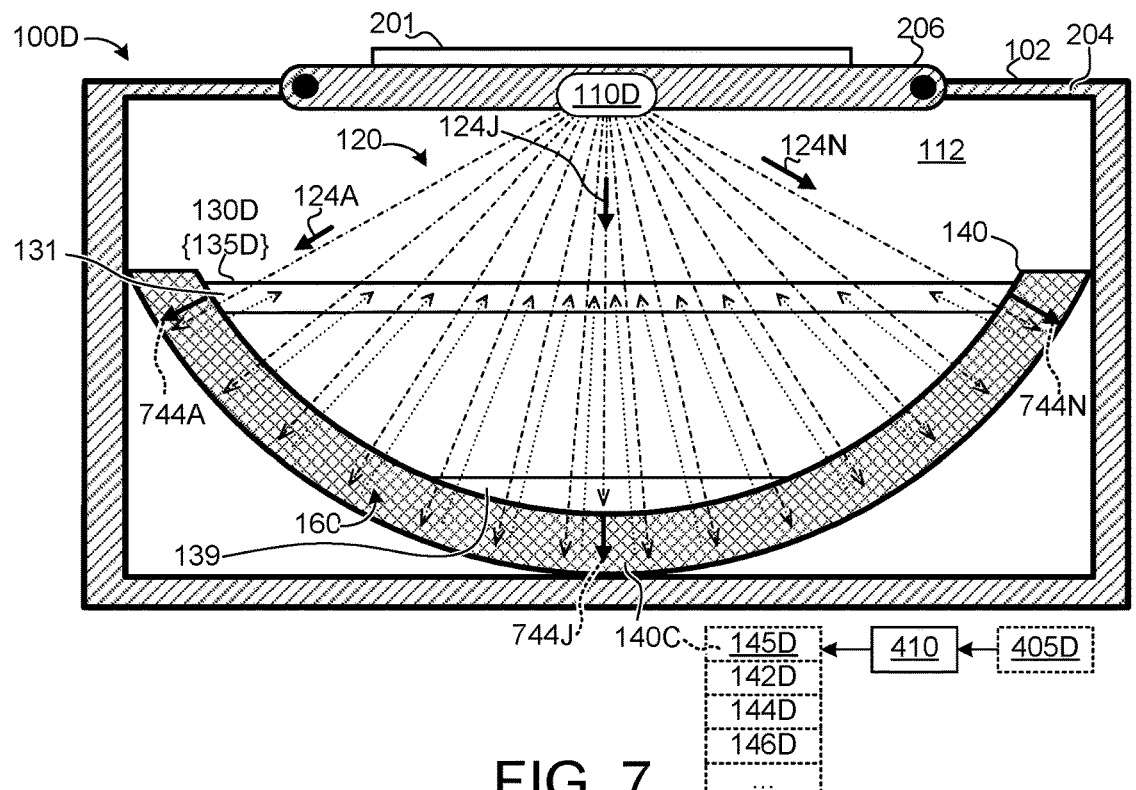
FIG. 7 illustrates another example of an irradiation device comprising a scattering medium.

FIG. 7 illustrates another example of an irradiation device 100D. In the FIG. 7 example, the source 110D of the irradiation device 100D may be configured to emit primary radiation 120. The primary radiation 120 may be configured to irradiate at least a portion of a target 130D having target characteristics 135D. In the FIG. 7 example, the orientation and/or position of the target 130D may cause the primary radiation 120 to penetrate the target 130D in non-parallel propagation directions 124 (e.g., propagation directions 124A through 124N). Alternatively, the source 110D may be configured to emit beams of the primary radiation 120 in a wide-angle pattern (in propagation directions 124A-N). FIG. 7 illustrates a cross-section of the irradiation device 100D along a plane substantially parallel to the propagation directions 124A-N. The target material 130D may receive a non-uniform dose of the primary radiation 120, as disclosed herein (e.g., represented by a MAX region 131 and MIN region 139).

In the FIG. 7 implementation, the irradiation device 100D comprises a scattering medium 140D, which may be configured in accordance with irradiation characteristics 405D of the irradiation device 100D, as disclosed herein (per a determined scattering medium configuration 145D). The physical configuration 144D determined for the scattering medium 140D may be configured to align depth axes 744 of the scattering medium 140D with the non-parallel, wide-angle propagation directions 124 of the primary radiation 120. More specifically, the physical configuration 144D may be configured to align respective depth axes 744-N of the scattering medium 140D with respective propagation directions 124A-N of the primary radiation 120 (e.g., align depth axes 744A, 744J, and 744N with propagation directions 124A, 124J, and 124N, and so on). In some embodiments, the physical configuration 144D may correspond to a convex, bowl, and/or hemispherical shape, as illustrated in FIG. 7.

Figure 8A:
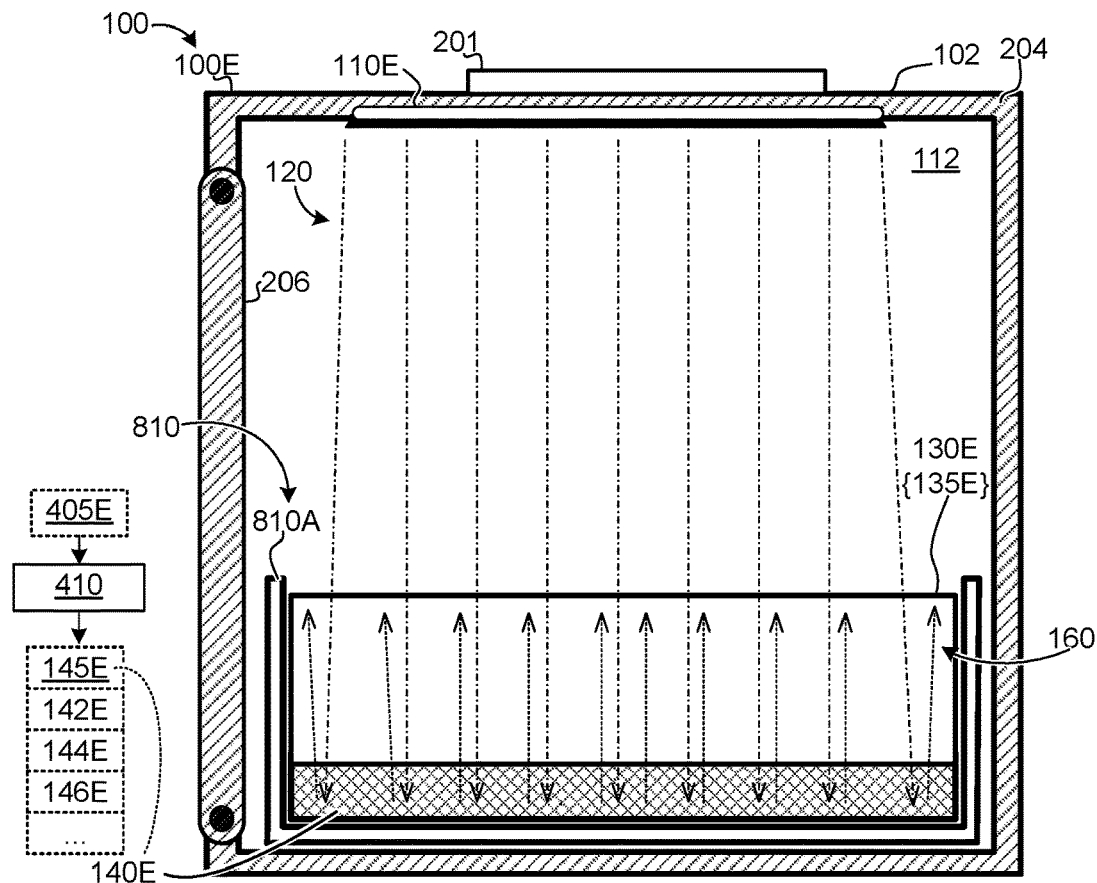
FIG. 8A illustrates another example of an irradiation device comprising a scattering medium and receptacle configured to hold a target material.
Figure 8B:
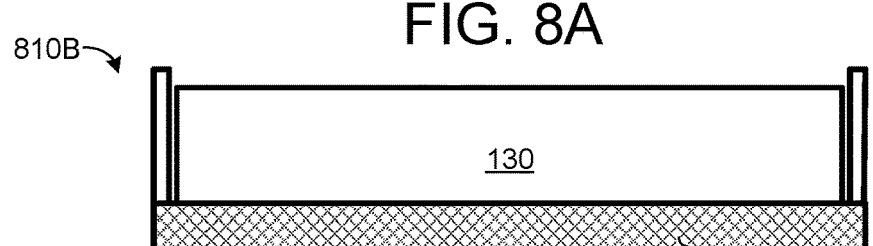
FIGS. 8B-H illustrate examples of receptacles of irradiation devices, as disclosed herein.
Figure 8C:
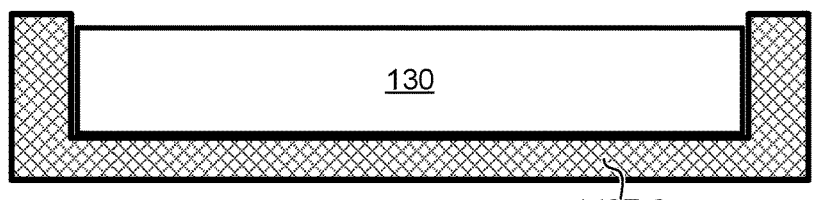
Figure 8D:
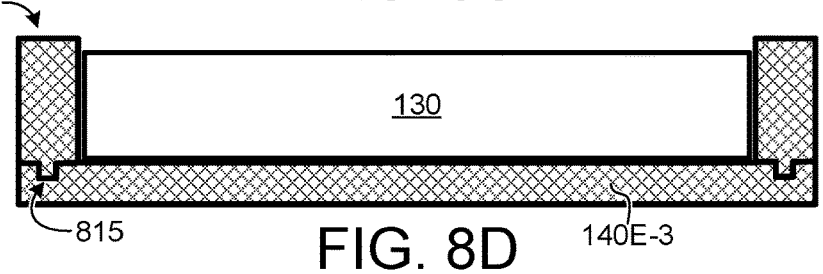
Figure 8E:
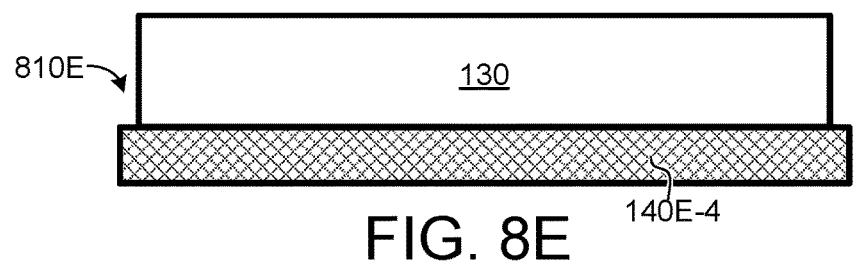

FIG. 8A illustrates another example of an irradiation device 100E. The irradiation device 100E may comprise a receptacle 810 (a receptacle 810A) configured to hold targets 130 and/or target material 130. The receptacle 810A may comprise any suitable means for supporting, holding, securing, and/or otherwise maintaining a target 130 and/or target material 130, including, but not limited to a pallet, tray, planar member, plank, box, canister, can, vessel, case, container, bowl, and/or the like. The receptacle 810A may be formed of any suitable material(s), including materials that are resistant to radiation produced by the source 110E of the irradiation device 100E. In the FIG. 8A example, the receptacle 810A may have a tray-like physical configuration comprising a base and plurality of sidewall members (e.g., four sidewall members, front and back sidewall members not shown to avoid obscuring details of the illustrated examples). In the FIG. 8A example, the receptacle 810A holds a target material 130E having target characteristics 135E.

A scattering medium 140E may be disposed within the receptacle 810A (e.g., on the base of the receptacle 810A). The scattering medium 140E may be adapted to the irradiation characteristics 405E of the irradiation device 100E, as disclosed herein (per the scattering medium configuration 145E). As illustrated in FIG. 8A, the thickness 146E of the scattering medium 140E may differ from the thickness and/or depth of the receptacle 810A (and/or base thereof). The scattering medium 140E may be significantly thicker and/or deeper than the receptacle 810A. The relatively larger thickness and/or depth of the scattering medium 140E may be adapted to facilitate Compton scatter interactions within the scattering medium 140E, as disclosed herein. Therefore, even if the receptacle 810A were to have the same or similar material composition 142E as the scattering medium 140E, the receptacle 810A would not yield significant improvements to irradiation performance (would not comprise a scattering medium 140 or a suitable scattering medium 140).

FIGS. 8B-H illustrate additional examples of receptacles 810 configured to maintain targets 130 and/or target materials 130 within irradiation devices 100. In the FIG. 8B example, scattering medium 140E-1 may form at least a portion of the base of the receptacle 810B. In the FIG. 8C example, at least a portion of the base and one or more sidewall members of the receptacle 810C may be formed from the scattering medium 140E-2. In the FIG. 8D example, scattering medium 140E-3 comprising the sidewall members of the receptacle 810D may be removably attached or interlocked to the base by a suitable mechanism, such as a notch, groove 815, or the like. In the FIG. 8E example, the receptacle 810E may be formed to have a substantially flat or planar configuration. The scattering medium 140E-4 comprise and/or implement at least a portion of the base of the receptacle 810E.

Figure 8F:
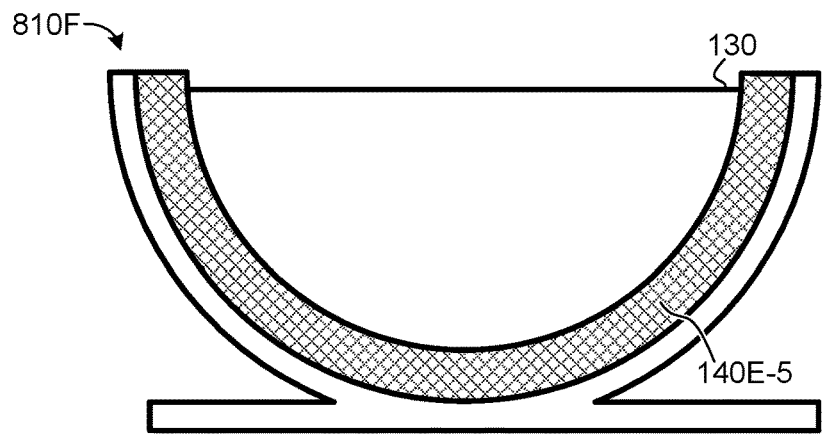
Figure 8G:
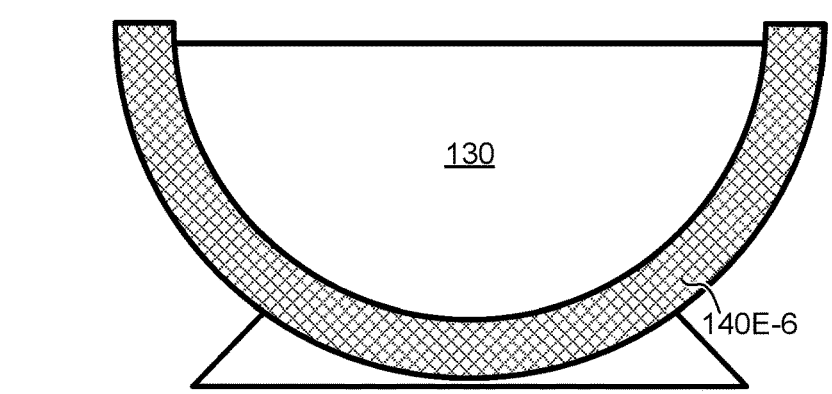
Figure 8H:
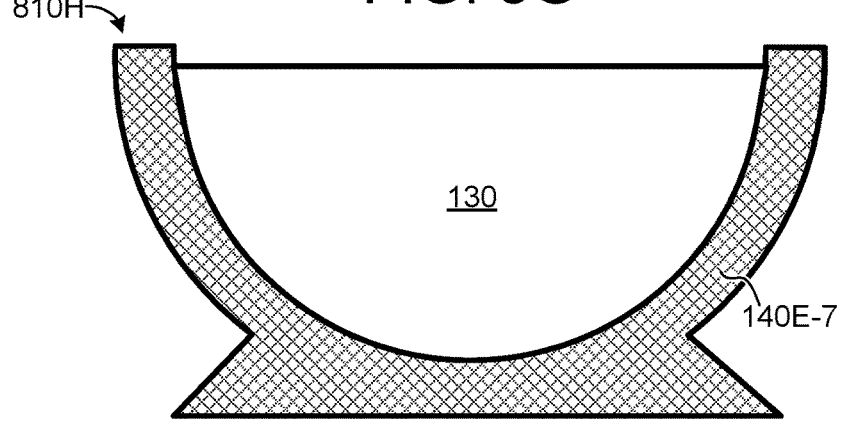

In the examples illustrated in FIGS. 8F-H, the receptacle 810 may be configured to have a convex or hemispherical physical configuration (e.g., a bowl shape). As shown in FIG. 8F, the scattering medium 140E-5 may be disposed between an inner surface of the receptacle 810F and the target material 130. In the FIG. 8G example, the scattering medium 140E-6 may form the hemispherical portion of the receptacle 810G. In the FIG. 8H example, the scattering medium 140E-7 may form the hemispherical portion and base of the receptacle 810H.

Figure 9:
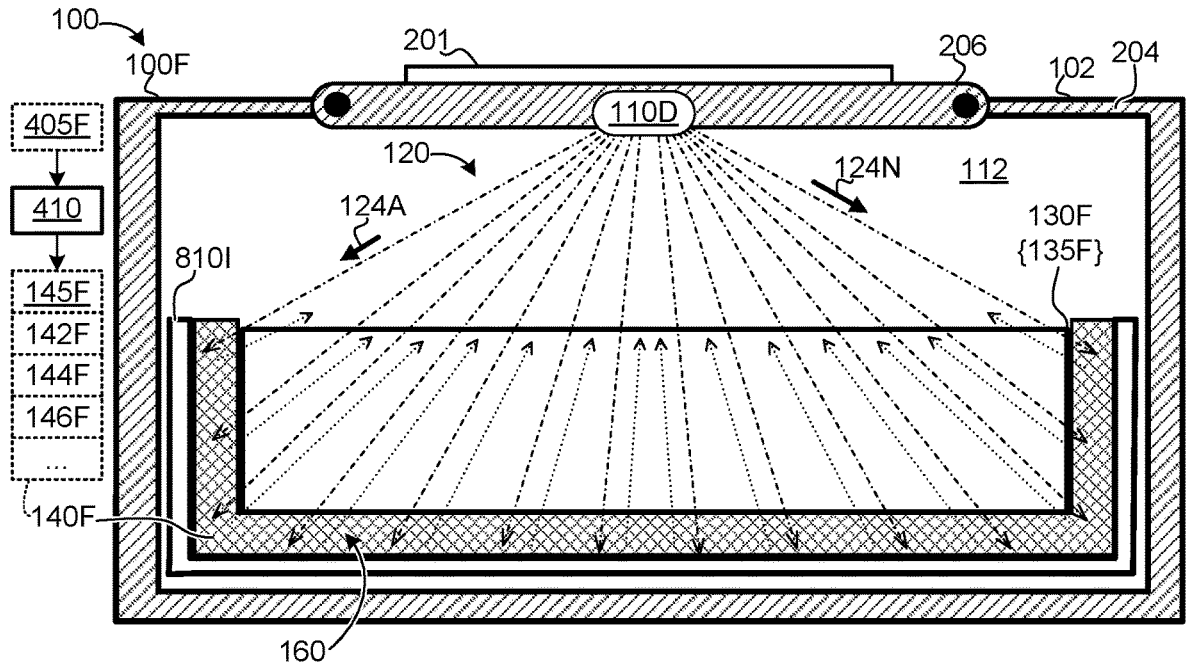
FIGS. 9 and 10 illustrate additional examples of irradiation devices comprising scattering media.

FIG. 9 illustrates another example of an irradiation device 100 (an irradiation device 100F). In the FIG. 9 example, the primary radiation 120 may irradiate the target material 130F in non-parallel propagation directions 124A-N (e.g., due to the target characteristics 135F, characteristics of the source 110D, or the like). A scattering medium 140F may be disposed along interior surfaces the receptacle 810I. The scattering medium 140F may be configured in accordance with the irradiation characteristics 405F of the irradiation device 100F, as disclosed herein (per a determined scattering medium configuration 145F). The physical configuration 144F of the scattering medium 140F may be adapted to align depth axes of the scattering medium 140F with propagation direction(s) 124 of the primary radiation 120. In some embodiments, portions of the scattering medium 140F may be removable and/or replaceable, as disclosed herein.

Figure 10:
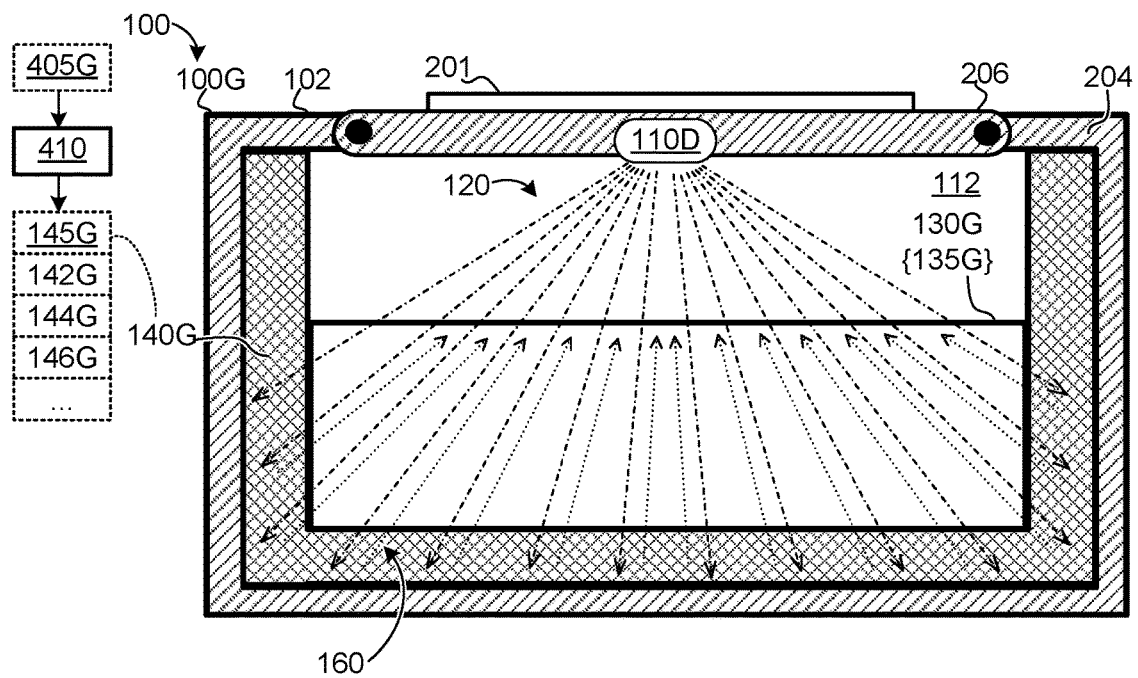

FIG. 10 illustrates another example of an irradiation device 100D having a source 110D. The irradiation device 100D may be configured to irradiate a target material 130G having target characteristics 135G. In the FIG. 10 example, the irradiation device 100G may comprise a scattering medium 140G. The scattering medium 140G may be configured based, at least in part, on irradiation characteristics 405F of the irradiation device 100F. As illustrated, the scattering medium 140G may be disposed on one or more (or two of more) interior surfaces of the enclosure 102 of the irradiation device 100G. The scattering medium 140G may be disposed on side, front, back, and/or bottom surfaces of the enclosure 102. In some implementations, the scattering medium 140G may be disposed on an upper interior surface of the enclosure 102, an interior surface of the access mechanism 206, and/or the like.

FIG. 11A illustrates another example of an irradiation device 100H. As illustrated, the enclosure 102 of the irradiation device 100H may be configured to hold one or more receptacles 810. The receptacles 810 may comprise containers 1110. The containers 1110 may be configured to hold respective targets 130 and/or respective quantities of a target material 130. In the FIG. 11A example, target material 130H having target characteristics 135H are disposed within respective containers 1110. The irradiation device 100H may include an access mechanism by which the containers 1110 may be placed within the enclosure 102, removed from the enclosure 102, and/or the like (access mechanism not shown in FIG. 11A to avoid obscuring details of the illustrated examples).

The containers 1110 may be secured in any suitable orientation within the enclosure 102, such as vertical, horizontal, or the like. In some implementations, a container lid 1112 or other mechanism may be configured to securely maintain target material 130 within the container 1110, as illustrated in FIG. 11B. In some embodiments, the containers 1110 may have a cylindrical shape. The disclosure is not limited in this regard, however, and could be adapted to use containers 1110 having any suitable physical configuration.

As illustrated in FIG. 11A, one or more containers 1110 may be arranged around a source 110H of the irradiation device 100H. In some embodiments, the source 110H may be configured to emit primary radiation 120 in a substantially radial or circular pattern (e.g., in a 360° range of propagation direction(s) 124). Alternatively, the source 110H may be configured to emit primary radiation 120 within a narrower angular range, or at least a partial radial or circular pattern, and the containers 1110 may be rotated around the source 110H such that each container 1110 periodically passes therethrough (as illustrated in the FIG. 11F example).

The target material 130H within the containers 1110 may receive non-uniform doses of the primary radiation 120. As illustrated in FIG. 11C, the containers 1110 may comprise a MAX region 131 comprising target material 130H closest to the source 110H and a MIN region 139 comprising target material 130H furthest from the source 110H.

In some implementations, physical manipulation may be employed in an attempt to ameliorate the effects of target non-uniformity. For example, containers 1110 may be rotated in direction 1132 during irradiation, as shown in FIG. 11C. Such physical manipulation may significantly increase the complexity (and cost) of the irradiation device 100H. Moreover, even if such physical manipulation were implemented, a significant ΔRDR may remain between portions of the target material 130 disposed within the inner region 1139 (e.g., MIN region 139) of the container 1110 and portions disposed within the outer region 1131 (e.g., MAX region 131).

In the FIG. 11A implementation, the irradiation device 100H may comprise a scattering medium 140H, which may be configured to improve aspects of irradiation performance as disclosed herein. The scattering medium configuration 145H may be adapted per the irradiation characteristics 405H of the irradiation device 100H. In the FIG. 11A example, the scattering medium 140H may be disposed on one or more (or two or more) interior surface(s) of the enclosure 102. In some embodiments, the scattering medium 140H may also be disposed on front and rear (or top and bottom) inner surfaces of the enclosure 102 (not shown in FIG. 11A to avoid obscuring details of the illustrated examples).

Figure 11D:
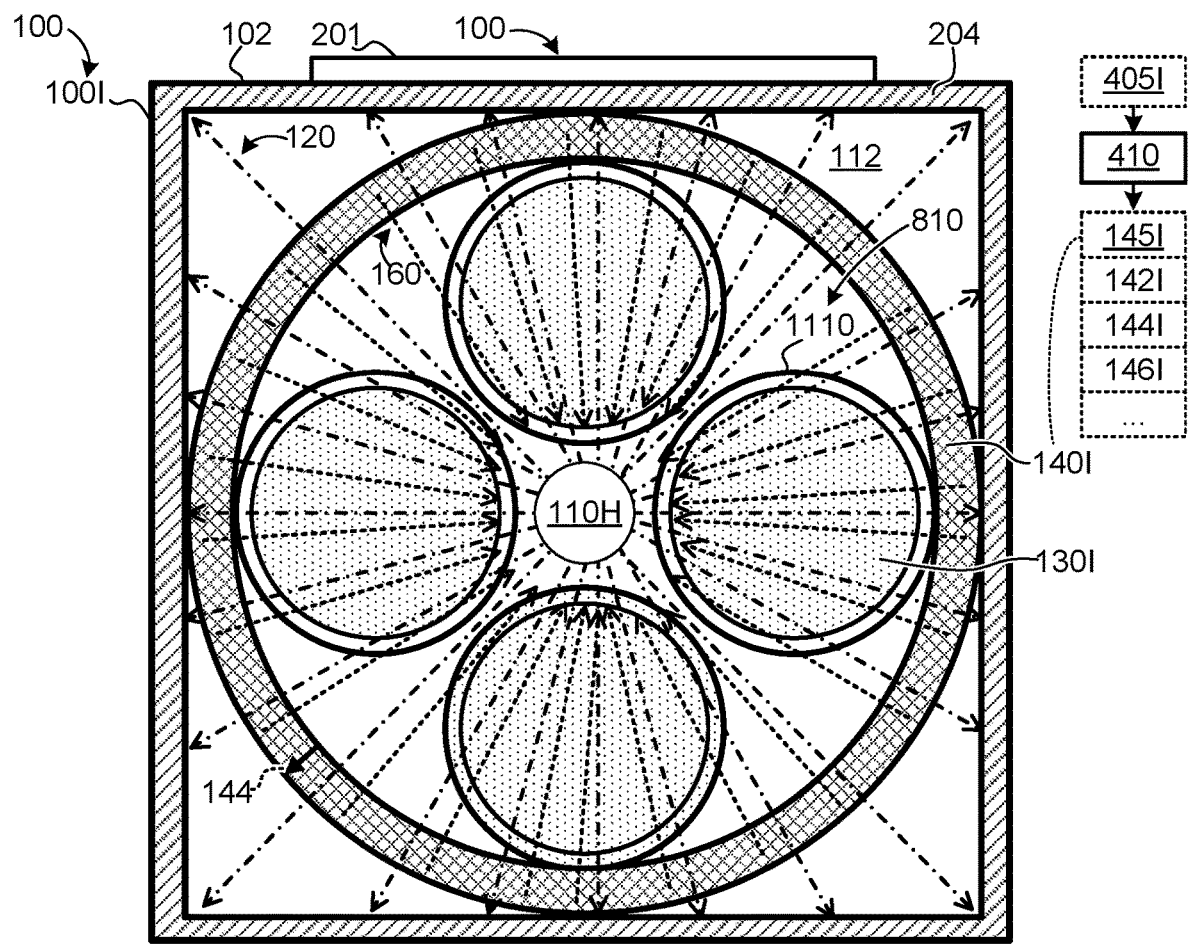
FIG. 11D illustrates another example of an irradiation device comprising a scattering medium.
Figure 11E:
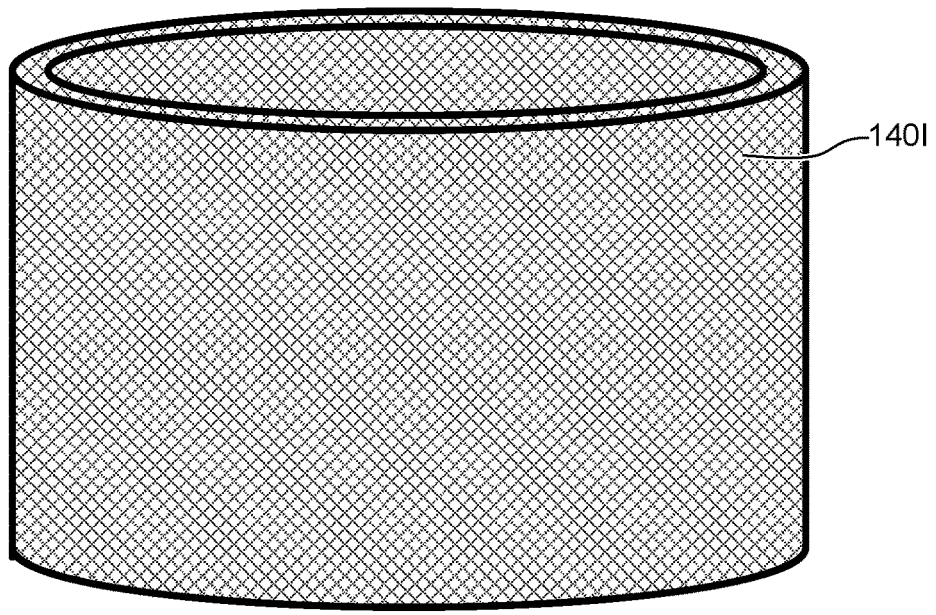
FIG. 11E illustrates an example of a cylindrical scattering medium.

FIG. 11D illustrates another example of an irradiation device 100I. The scattering medium 140I of the irradiation device 100I may be formed in a substantially cylindrical shape (as further illustrated in FIG. 11E). The scattering medium configuration 145I may be determined in accordance with irradiation characteristics 405I of the irradiation device 100I, as disclosed herein. In the FIG. 11D example, the physical configuration 144I of the scattering medium 140I may be adapted to align depth axes of the scattering medium 140I with propagation direction(s) 124 of the primary radiation 120, as disclosed herein. In some implementations, the inner surface of the scattering medium 140I may be configured to be substantially normal to the primary radiation 120, which may facilitate generation of secondary radiation 160 back towards the target material 130I within the containers 1110, as disclosed herein.

Figure 11F:
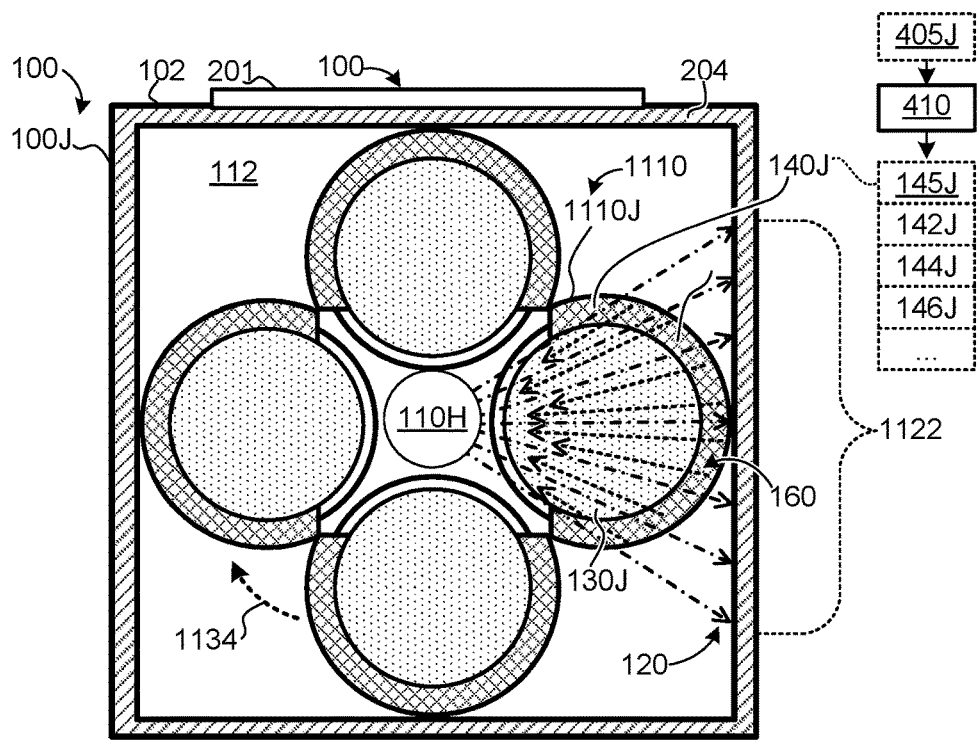
FIG. 11F illustrates another example of an irradiation device comprising a scattering medium.

FIG. 11F illustrates another example of an irradiation device 100J. In the FIG. 11F example, the containers 1110J of the irradiation device 100J may comprise and/or be coupled to respective scattering media 140J (each container 1110J configured to hold respective target material 130J). The scattering medium configuration 145J determined for the scattering media 140J may be based, at least in part, on irradiation characteristics 405J of the irradiation device 100J, as disclosed herein. In some embodiments, the scattering medium 140J may form a portion of the cylindrical wall of respective containers 1110J. For example, the scattering medium 140J may form portions of the cylindrical wall that are furthest from the source 110H (e.g., between about 200° and 315° of the outer portion of the cylindrical wall). In FIG. 11F, only a portion of the primary radiation 120 emitted by the source 110H (and corresponding secondary radiation 160 emitted by the scattering medium 140J) is shown to avoid obscuring details of the illustrated examples.

Figures 11G, 11H:
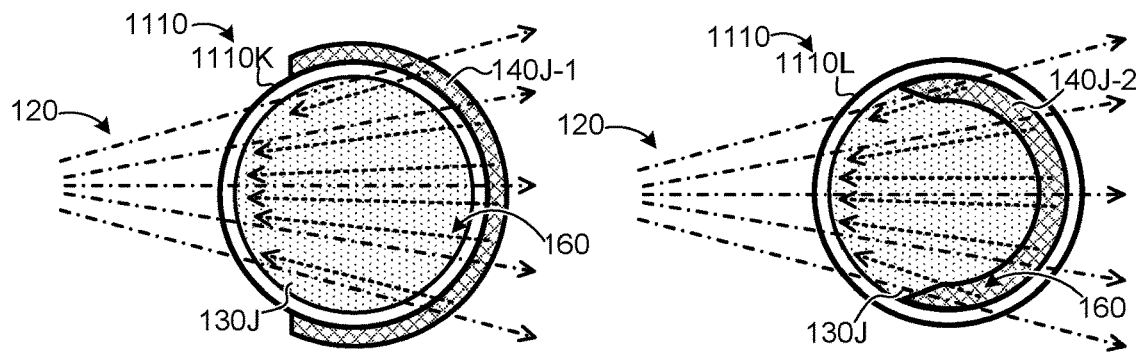
FIGS. 11G-I illustrate examples of containers comprising scattering media.
Figure 11I:
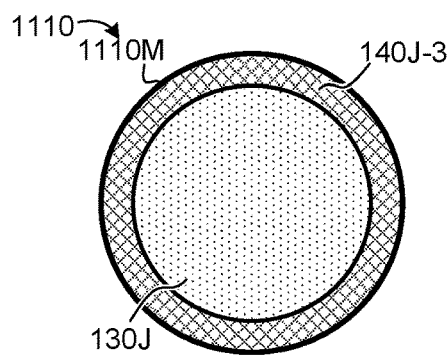

FIGS. 11G-11I illustrate further examples of containers 1110 configured to hold target material 130 within the enclosure 102 of an irradiation device 100, such as the irradiation device 100H, 100I, or 100J. In the FIG. 11G example, scattering medium 140J-1 may be disposed on an outer surface of the cylindrical wall of the container 1110K. In the FIG. 11H example, scattering medium 140J-2 may be disposed on an inner surface of the cylindrical wall of the container 1110L. In the FIG. 11I example, cylindrical walls of the container 1110M may be formed from the scattering medium 140J-3.

Figure 12A:
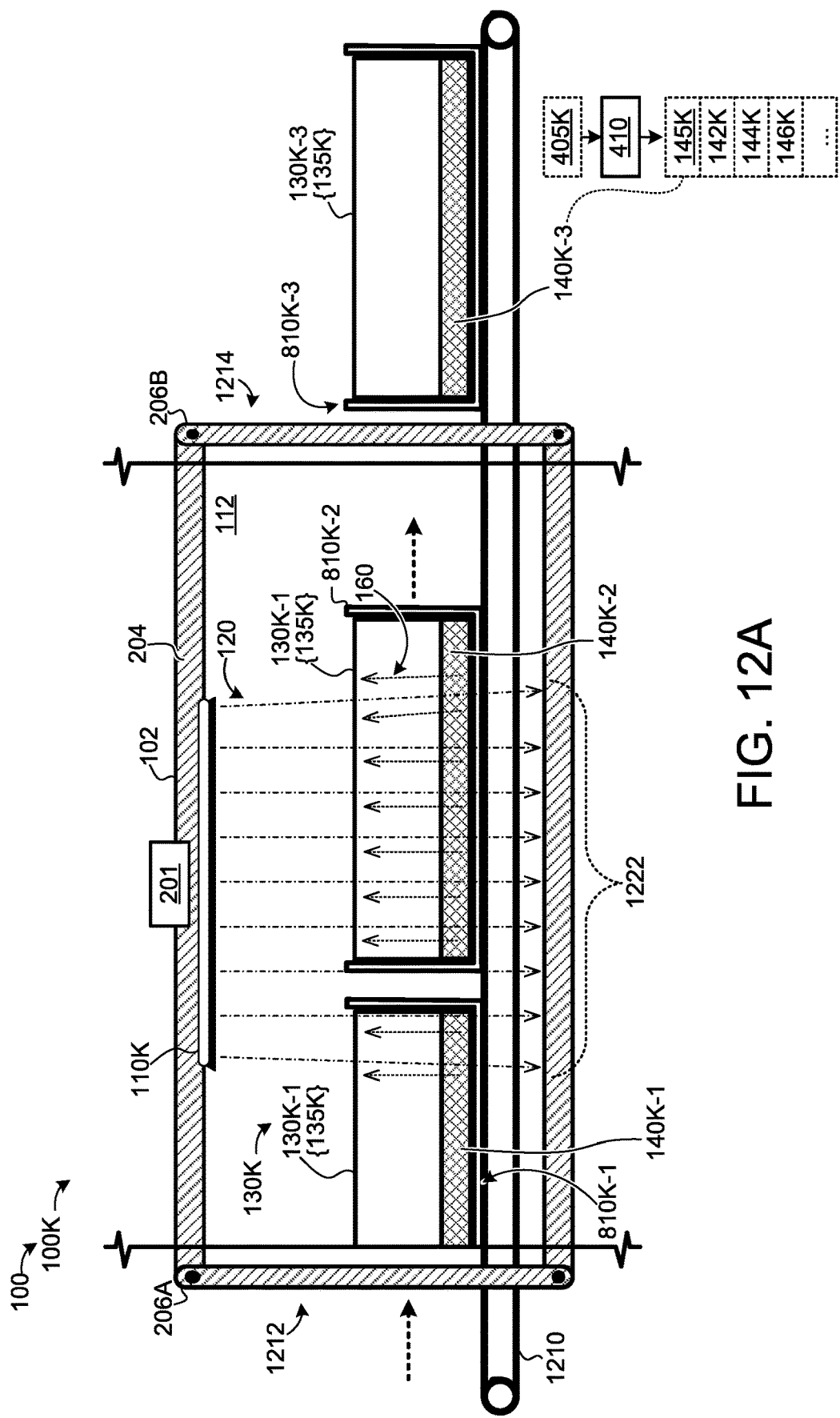
FIGS. 12A-B illustrate examples of irradiation devices configured to implement continuous-feed irradiation operations.

Although examples of irradiation devices 100 configured to implement batch-type operations are described herein, the disclosure is not limited in this regard and could be adapted for use with irradiation devices 100 configured to implement other types of irradiation operations, such as continuous-feed irradiation operations, or the like. FIG. 12A illustrates an example of an irradiation device 100K configured to implement continuous-feed irradiation operations. The irradiation device 100K may be configured to process target material 130K having target characteristics 135K. The target material 130K may be held on and/or within respective receptacles 810K (or respective containers 1110). The source 110K of the irradiation device 100K may be configured to emit primary radiation 120 into and/or within an interior volume 112 of the enclosure 102. The primary radiation 120 may be directed into an irradiation zone 1222 within the enclosure 102.

The irradiation device 100K may further include a conveyor 1210 which may be configured to transfer target material 130K into an entrance 1212 of the enclosure 102 (through a first access mechanism 206A) through the irradiation zone 1222 and out an exit 1214 of the enclosure 102 (through a second access mechanism 206B). The target material 130K disposed within respective receptacles 810K may be irradiated as the respective receptacles 810K are transferred through the irradiation zone 1222 by the conveyor 1210. The amount of time the target material 130 is maintained within the irradiation zone 1222 may determine an irradiation time and/or the RD delivered to the target material 130. In the FIG. 12A example, the target material 130K-1 within receptacle 810K-1 has entered the enclosure 102 through the first access mechanism 206A and is partially within the irradiation zone 1222, the target material 130K-2 within receptacle 810K-2 is partially within the irradiation zone 1222 (is leaving the irradiation zone 1222) and the target material 130K-3 within receptacle 810K-3 has exited the enclosure 102 through the second access mechanism 206B after having been irradiated while passing through the irradiation zone 1222. The receptacles 810K may comprise scattering media 140K (e.g., scattering media 140K-1 through 140K-3). The scattering medium configuration 145K of the scattering media 140K may be adapted to improve aspects of irradiation performance per the irradiation characteristics 405K of the irradiation device 100K, as disclosed herein.

Figure 12B:
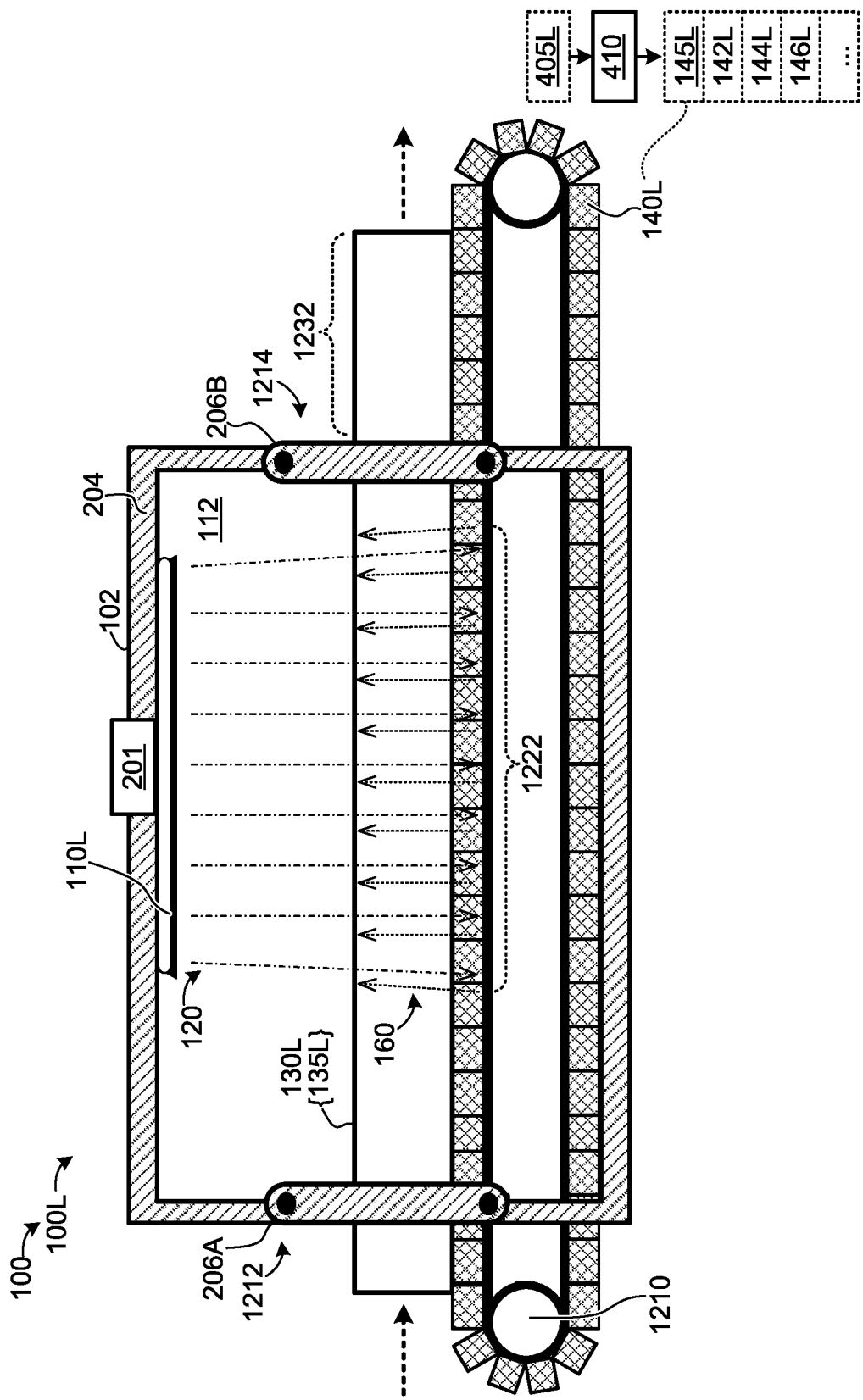

FIG. 12B illustrates another example of an irradiation device 100L configured to implement continuous-feed irradiation operations. In the FIG. 12B example, target material 130L having target characteristics 135L may be received on the conveyor 1210. The target material 130 may be received in a substantially continuous manner. The access mechanism 206A may be configured to receive the target material 130L into the interior volume 112 of the enclosure 102 while preventing radiation from escaping therefrom.

The control logic 201 may configure the source 110L to emit primary radiation 120 as the conveyor 1210 moves target material 130L through the irradiation zone 1222. The control logic 201 may configure the conveyor 1210 to move target material 130 through the irradiation zone 1222 such that the target material 130L receives a specified RD (and/or remains within the irradiation zone 1222 for a specified irradiation time). Irradiated portion(s) 1232 of the target material 130L may be retrieved at an exit 1214 of the irradiation device 100 (e.g., through a second access mechanism 206B).

The irradiation device 100L may further scattering media 140L. The scattering medium configuration 145L of the scattering media 140L may be adapted to the irradiation characteristics 405L of the irradiation device 100L, as disclosed herein. In the FIG. 12B example, scattering media 140L may be disposed on the conveyor 1210. The scattering media 140L may comprise a belt or other component of the conveyor 1210. Alternatively, or in addition, scattering media 140L may be disposed on and/or within the conveyor 1210. As illustrated in FIG. 12B, scattering media 140L may comprise a plurality of panels or segments, which may be configured to be disposed on a belt or other component of the conveyor 1210. The scattering medium configuration 145L of the scattering media 140L may be determined by configuration logic 410 based, at least in part, on irradiation characteristics 405L of the irradiation device 100L.

Figure 13:
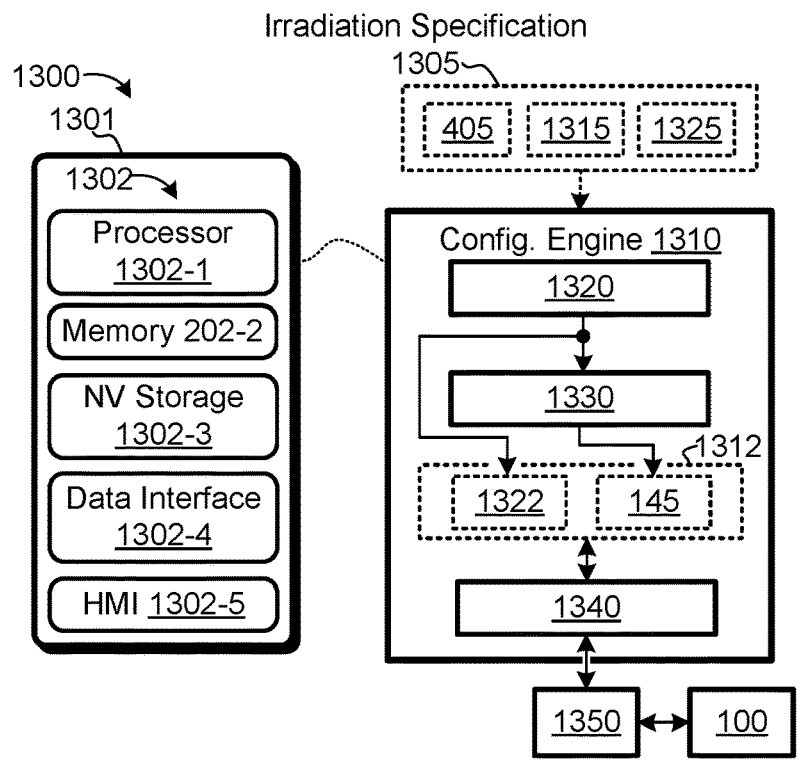
FIG. 13 illustrates an example of a system for configuring an irradiation device.

FIG. 13 illustrates an example of a system 1300 for configuring an irradiation device 100 to implement an irradiation application and/or using the configured irradiation device 100 to implement the irradiation application. The system 1300 may comprise an configuration engine 1310, which may be configured for operation on computing resources 1302 of a computing device 1301. The computing resources 1302 may include, but are not limited to: a processor 1302-1, memory 1302-2, NV storage 1302-3, data interface 1302-4, HMI 1302-5, and/or the like. The configuration engine 1310 may comprise and/or be embodied by computer-readable instructions stored on the NV storage of the computing device 1301 (and/or other non-transitory storage medium). Alternatively, or in addition, portions of the configuration engine 1310 may be implemented and/or embodied by hardware components, such as logic circuitry, processing circuitry, an ASIC, an FPGA, and/or the like.

The configuration engine 1310 may receive specification data 1305 pertaining to an irradiation application to be implemented by an irradiation device 100 having specified irradiation characteristics 405. The specification data 1305 may comprise and/or be embodied by electronically encoded information configured for storage on a non-transitory storage medium, communication on an electronic communication network, and/or interpretation by processing resources of the computing device 1301. The configuration engine 1310 may generate an irradiation configuration 1312 for the specified irradiation application. As disclosed in further detail herein, the irradiation configuration 1312 may comprise an primary radiation configuration 1322 and/or scattering medium configuration 145. The primary radiation configuration 1322 may configure the source 110 of the irradiation device 100 to deliver a specified threshold radiation dose to a target material 130 having specified target characteristics 135 (emit primary radiation 120, as disclosed herein). The scattering medium configuration 145 may specify a material composition 142, physical configuration 144, thickness 146, and/or other characteristics adapted to improve aspects of irradiation performance, as disclosed herein. The irradiation configuration 1312 may be maintained on and/or within NV storage 1302-3 of the computing device 1301. Alternatively, or in addition, the irradiation configuration 1312 may be transmitted on an electronic communication network to other component(s) of the system 1300, other computing device(s) and/or systems, control logic 201 of an irradiation device 100, and/or the like.

The specification data 1305 may include irradiation characteristics 405 of the irradiation device 100 and target characteristics 135 pertaining to the target material 130 to be irradiated in the irradiation application. The specification data 1305 may further include radiation dose data 1325, which may specify the radiation dose to be delivered to the target material (e.g., a threshold radiation doses). For example, the specification data 1305 may involve sterilization of cannabis having specified target characteristics 135 by a radiation dose of 2 kilo gray (KGy).

The configuration engine 1310 may further comprise a dose modeling module 1320, which may be configured to determine a primary radiation configuration 1322 for the irradiation application. The primary radiation configuration 1322 may be configured to cause the irradiation device 100 to deliver the specified radiation dose to the specified target material 130. The dose modeling module 1320 may be configured to determine an irradiation time and energy composition 520 for the primary radiation 120 (e.g., an energy level 521, energy range 522, or the like). For a cannabis sterilization application, the primary radiation configuration 1322 may specify an energy level of about 140 keV for cannabis having a density of about 0.1 g/cc and a depth of about 2 inches, an energy level of about 180 keV for cannabis having a density of about 0.1 g/cc and a depth of about 4 inches, and so on. In some implementations, suitable (or optimal) primary radiation configurations 1322 may be determined through testing and/or experience (e.g., by irradiating samples of target material 130 having different target characteristics 135 within an ion chamber, radiation sensors, automatic exposure control (AEC), and/or the like).

The configuration engine 1310 may further comprise a scatter modeling module 1330, which may be configured to determine a suitable (or optimal) scattering medium configuration 145 for the scattering medium 140 of the irradiation device 100. The scatter modeling module 1330 may comprise and/or implement configuration logic 410, as disclosed herein. In some implementations, the scatter modeling module 1330 may be further configured to determine scattering metrics for the determined scattering medium configuration 145. The scattering metrics may be configured to estimate irradiation performance improvements for determined scattering medium configurations 145. The scattering metrics may, for example, specify an estimated reduction to $\Delta$RDR, estimated increase to RD rate ($\Delta$RD), estimated decrease to irradiation time, and/or the like, as disclosed herein.

In some implementations, the configuration engine 1310 may be further comprise an adaptation module 1340. The adaptation module 1340 may be configured to modify, refine, and/or otherwise adapt the irradiation configuration 1312 to different conditions and/or feedback regarding testing and/or implementation of the irradiation application by the irradiation device 100. For example, the adaptation module 1340 may be configured to modify and/or refine the primary radiation configuration 1322 based, at least in part, on scattering metrics determined for the scattering medium configuration 145. More specifically, the adaptation module 1340 may be configured to modify the primary radiation configuration 1322 in accordance with the irradiation performance improvements predicted to be realized by incorporation of a scattering medium 140 having the specified configuration 145. The modifications may comprise decreasing the energy level 521 of the primary radiation 120, decreasing the irradiation time, increasing the rate at which target material 130 passes through an irradiation zone 1222, increasing the throughput of the irradiation device 100, and/or the like.

In some implementations, the configuration engine 1310 may further comprise and/or be coupled to an irradiation manager (or manager 1350). The manager 1350 may be adapted to configure the irradiation device 100 to implement the irradiation configuration 1312 determined by the configuration engine 1310. The manager 1350 may be configured to cause the irradiation device 100 to incorporate a scattering medium 140 configured per the scattering medium configuration 145 determined by the scatter modeling module 1330. The manager 1350 may be further adapted to configure the irradiation device 100 to implement the irradiation application as specified by the primary radiation configuration 1322. Implementing the irradiation application may comprise a) receiving target material 130 within the interior volume 112 of the irradiation device 100 in the physical configuration specified by the target data 1315 (e.g., target characteristics 135) and b) causing the source 110 of the irradiation device 100 to emit primary radiation 120 in accordance with the primary radiation configuration 1322, the primary radiation 120 configured to irradiate at least a first portion of the target material 130. Control logic 201 of the irradiation device 100 may be configured to cause the source 110 to emit primary radiation 120 at energy level(s) 521 and/or within energy range(s) 522 for an irradiation time specified by the primary radiation configuration 1322. The scattering medium 140 may be configured to produce secondary radiation 160 in response to the primary radiation 120, which may be configured to irradiate at least a second portion of the target material 130, as disclosed herein.

In some embodiments, the manager 1350 may be further configured to acquire feedback data pertaining to testing and/or implementation of the determined irradiation configuration 1312. The feedback data may comprise any suitable information including, but not limited to an actual, measured RD delivered to the target material 130 (and/or respective portions or regions of the target material 130), actual irradiation time to deliver the specified radiation dose to the target material 130, and/or the like. The feedback data may be acquired by use of test and/or monitoring devices, such as an ion chamber, radiation sensors, AEC units, and/or the like (not shown in FIG. 13 to avoid obscuring details of the illustrated embodiments).

In some implementations, the adaptation module 1340 may utilize feedback data pertaining to respective irradiation configurations 1312 to modify, refine, and/or otherwise adapt the respective irradiation configurations 1312. The modifications to the irradiation configurations 1312 may be maintained within non-transitory storage, such as the NV storage 1302-3 of the computing device 1301.

The adaptation module 1340 may be further configured to utilize the feedback data to refine rules and/or metrics used to determine and/or develop irradiation configurations 1312 for specified irradiation applications (e.g., for respective specification data 1305). For example, the adaptation module 1340 may utilize feedback regarding the actual RD delivered to a target material 130 per a specified irradiation configuration 1312 to refine target characteristics 135 of the target material 130 (e.g., photoelectric absorption), scattering metrics determined for the scattering medium configuration 145, and/or the like. Thus, the feedback data may be used not only to refine the irradiation configuration 1312 for the specific irradiation application but may also be used to refine other irradiation configuration(s) 1312 for other irradiation applications.

In some implementations, the adaptation module 1340 may be further configured to utilize the feedback data to learn and/or refine relationships between characteristics and/or parameters of specification data 1305 and/or corresponding irradiation configurations 1312. For example, the adaptation module 1340 may utilize the feedback data to learn relationships between target characteristics 135 (e.g., density, photoelectric absorption and/or attenuation, physical configuration, and/or the like) and irradiation performance (e.g., RD delivered to the target material 130, RD delivered to respective regions, RDR rate, ΔRDR, and/or the like). The adaptation module 1340 may be further configured to learn and/or refine relationships involving characteristics of scattering media 140 (e.g., as defined by scattering medium configurations 145 determined for the scattering media 140). The relationships may correspond to irradiation performance improvements yielded by scattering media 140 having respective scattering medium configurations 145 under specified conditions, as illustrated in FIGS. 5B and 6B (e.g., improvements yielded for targets 130 having specified target characteristics 135, primary radiation 120 having specified energy compositions 520, and so on). The adaptation module 1340 may be configured to learn and/or refine such relationships using any suitable mechanism or technique. For example, the adaptation module 1340 may comprise and/or be coupled to a machine-learning or machine-learned irradiation model, or the like. The adaptation module 1340 may be further adapted to configure the dose modeling module 1320 and/or scatter modeling module 1330 to utilize the learned correlational relationships to produce irradiation configurations 1312 for specified irradiation applications, as disclosed herein.

Figure 14:
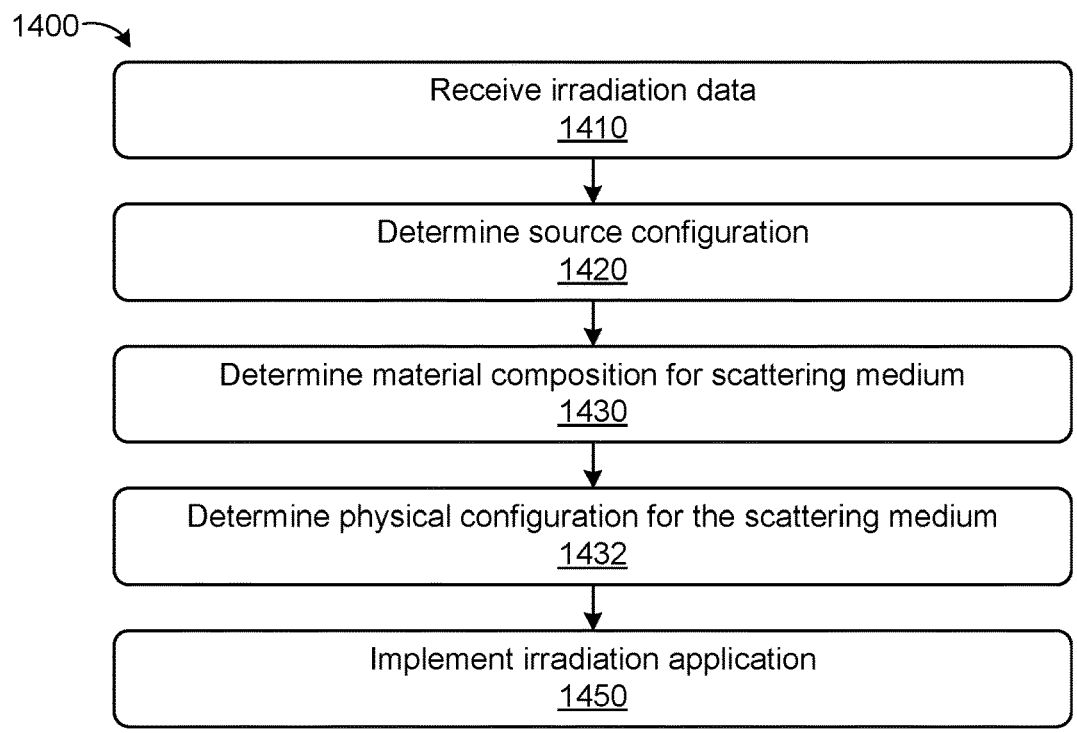
FIG. 14 is a flowchart illustrating examples of techniques for determining a configuration for a scattering medium of an irradiation device.

FIG. 14 is a flowchart 1400 illustrating examples of techniques for determining suitable (or optimal) characteristics for the scattering medium 140 of an irradiation device 100. The flowchart 1400 may correspond to functionality comprising one or more steps or operations (a method). In some implementations, portions of the functionality described in conjunction with FIG. 14 (and/or other flowcharts disclosed herein) may be implemented and/or embodied by hardware components, such as circuitry, logic, logic circuitry, a processor, an ASIC, an FPGA, a computing device, and/or the like. Alternatively, or in addition, portions of the disclosed functionality may be implemented and/or embodied by computer-readable instructions stored on an NV or non-transitory storage medium. The computer-readable instructions may be configured to cause logic, such as a processor of a computing device 1301 and/or control logic 201 of an irradiation device 100, to implement portions of the disclosed functionality.

In 1410, specification data 1305 configured to define an irradiation application to be implemented by an irradiation device 100 may be received. In 1420, an primary radiation configuration 1322 for the specification data 1305 may be determined, as disclosed herein. In 1430, a suitable (or optimal) material composition 142 for the scattering medium 140 may be determined, as disclosed herein (e.g., based on the energy composition 520, energy level 521, and/or energy range 522 specified by the primary radiation configuration 1322). In 1434, a suitable (or optimal) physical configuration 144 for the scattering medium 140 may be determined, as disclosed herein. The scattering medium configuration 145 may be configured to improve irradiation performance by at least a threshold. The scattering medium configuration 145 may be configured to reduce target non-uniformity (e.g., ΔRDR) to 10% or less (e.g., or 2.5% or less), reduce irradiation time by 10% or more, increase RDR by 10% or more, increase radiation dose by 10% or more, and/or the like. In some implementations, the primary radiation configuration 1322 determined in 1420 may be modified and/or refined based on utility metrics determined for the scattering medium 140 (and/or scattering medium configuration 145), as disclosed herein. In some implementations, aspects of 1430-1434 may be implemented by configuration logic 410, a scatter modeling module 1330 and/or an adaptation module 1340 operating on a computing device 1301, as disclosed herein.

In 1450, the irradiation application defined by the specification data 1305 may be implemented by an irradiation device 100. Implementing the irradiation application may comprise a) deploying a scattering medium 140 configured per the determined scattering medium configuration 145 within the irradiation device 100, and b) configuring the irradiation device 100 to irradiate a target 130 (having specified target characteristics 135) with primary radiation 120 as defined by the primary radiation configuration 1322 determined at 1420, as disclosed herein.

Figure 15A:
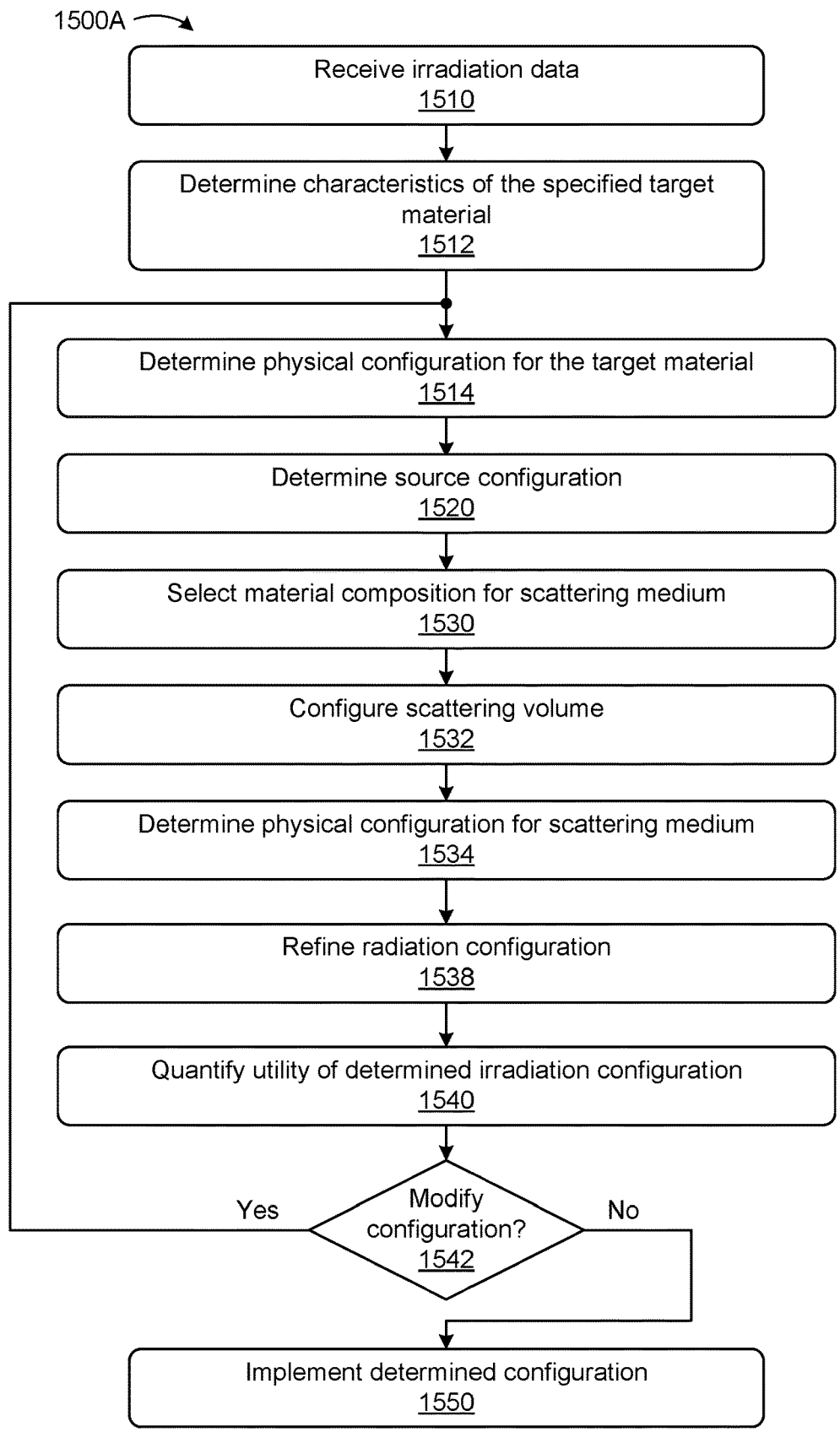
FIG. 15A is a flowchart illustrating examples of techniques for determining a configuration for an irradiation application.

FIG. 15A is a flowchart 1500A illustrating examples of techniques for determining suitable (or optimal) configurations for irradiation applications. In 1510, specification data 1305 pertaining to an irradiation application may be received. In 1512, target characteristics 135 of the target material 130 specified by the irradiation requirements may be determined. In some implementations, the target characteristics 135 may be determined through testing and/or experience. Alternatively, or in addition, one or more target characteristics 135 may be known, may be specified by a supplier, may be included in target data 1315 received in 1510, and/or the like.

In 1514, a physical configuration for the target material 130 during irradiation may be determined. The physical configuration may correspond to an extent and/or amount of the target material 130 to be processed in each batch or irradiation operation implemented by the irradiation device 100. Alternatively, in 1514 the physical configuration of target material 130 to be processed in continuous-feed irradiation operations may be determined. The physical configuration of the target material 130 may correspond to a position and/or orientation of the target material 130 relative to the source 110 of the irradiation device 100 and/or the primary radiation 120 generated thereby. The physical configuration of the target material 130 may determine a depth or thickness of the target material 130 relative to the direction(s) in which the primary radiation 120 is emitted (e.g., 2-inches, 4-inches, or the like).

In 1520, a primary radiation configuration 1322 to deliver a specified radiation dose to the target material 130 (having specified target characteristics 135) may be determined, as disclosed herein.

In 1530-1534 a suitable (or optimal) scattering medium configuration 145 may be determined, as disclosed herein. In 1538, the primary radiation configuration 1322 determined in 1520 may be refined based, at least in part, on projected improvements yielded by incorporation of the scattering medium 140 having the scattering medium configuration 145 determined at 1530-1534. The primary radiation configuration 1322 and/or scattering medium configuration 145 may be included in an irradiation configuration 1312, which may be persisted to NV storage 1302-3 of a computing device 1301 and/or other non-transitory computer-readable storage media.

In 1540-1542, the determined irradiation configuration 1312 may be evaluated, modified, and/or refined. In 1540, a utility of the irradiation configuration 1312 determined in 1514-1538 may be determined. In 1540, the fitness or utility of the irradiation configuration 1312 may be quantified and/or expressed as a utility or fitness metric, e.g., an irradiation configuration utility (IRCU) metric. The IRCU metric may be based any suitable factor(s), which may include, but are not limited to the resulting ΔRD, irradiation time per iteration or batch, irradiation time as a function of quantity, throughput (e.g., quantity of target material 130 processed per unit time), radiation energy level (and/or energy range), power consumption, power consumption rate (e.g., power consumption per quantity of target material 130 processed), cost, cost of scattering medium 140, and/or the like. In some implementations, the IRCU metric may be based on feedback data, as disclosed herein. Alternatively, or in addition, the IRCU metric may be determined through estimated or simulated implementation of the irradiation configuration 1312. In some implementations, weights may be assigned to respective factors, which may indicate a relative importance of the factors to the IRCU metric of the resulting irradiation application (e.g., emphasize throughput over power consumption and/or ΔRD, or the like). The weights may be assigned by a user, user preferences, or the like. One or more of the factors and/or weights may be included in the specification data 1305 received in 1510. In some implementations, the IRCU metric may be formulated as an objective function of an optimization process.

In 1542, the IRCU metric may be evaluated to determine whether to modify and/or refine the irradiation configuration 1312 determined at 1514-1538. This determination may be based on whether the IRCU metric satisfies a threshold. Alternatively, or in addition, the determination may be based on comparisons between the IRCU metric determined for the irradiation configuration 1312 and IRCU metrics of other irradiation configurations 1312 (e.g., irradiation configurations 1312 determined in previous iterations of 1514-1538). In some implementations, 1514-1542 may be formulated as an optimization problem, and the determination in 1542 may be based on whether an optimal irradiation configuration 1312 for the irradiation application has been identified. If the irradiation configuration 1312 is to be modified, the flow may continue back in 1514-1534; otherwise, the flow may continue at 1550. In 1550 the determined configuration of the irradiation application may be implemented by an irradiation device 100, as disclosed herein.

Figure 15B:
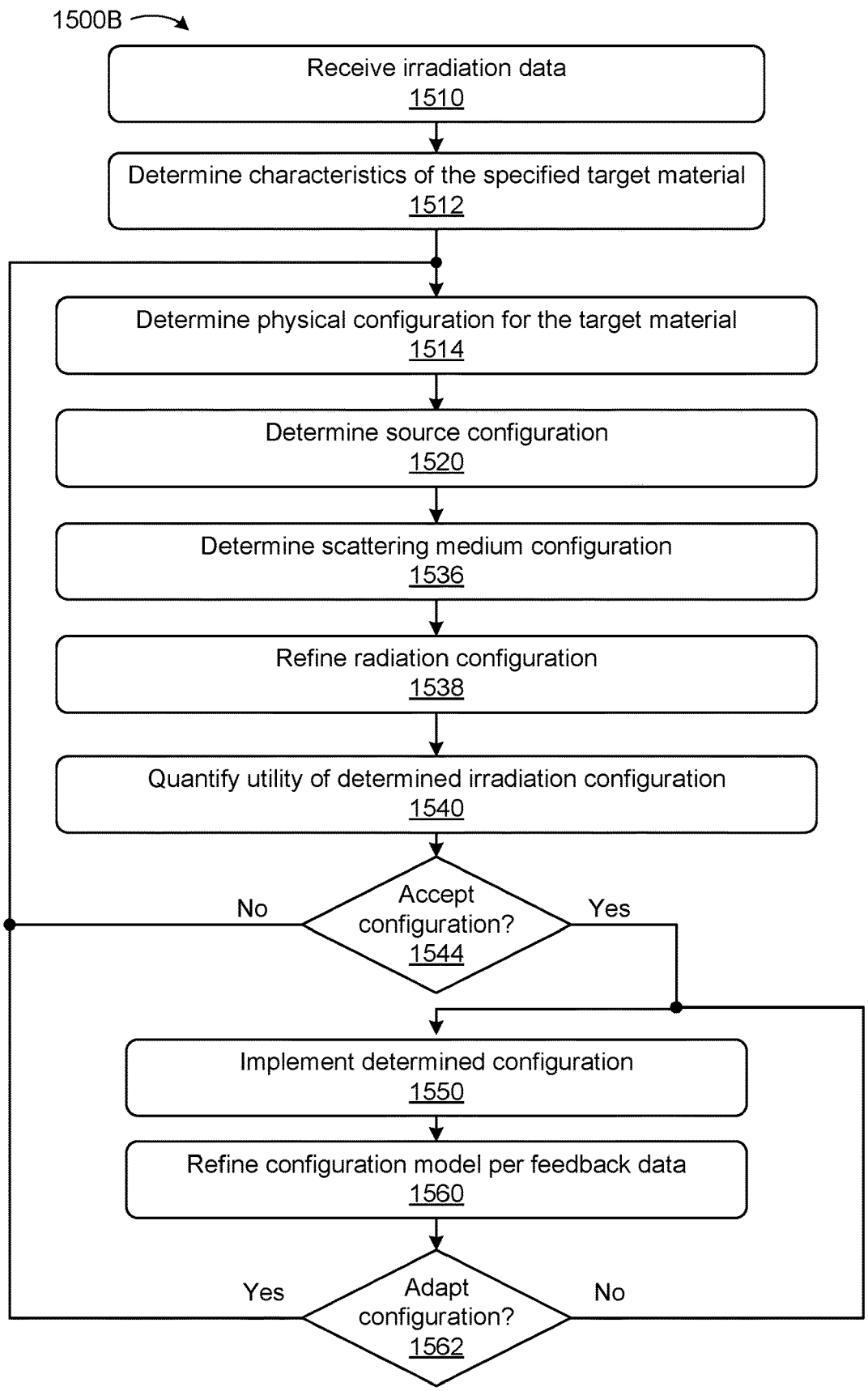
FIG. 15B is a flowchart illustrating further examples of techniques for determining a configuration for an irradiation application.

FIG. 15B is a flowchart 1500B illustrating further examples of techniques for determining suitable (or optimal) configurations for irradiation applications. As illustrated, in 1510, specification data 1305 pertaining to an irradiation application may be received, in 1512, characteristics of the target material 130 may be determined, in 1514, a physical configuration of the target material 130 during irradiation may be determined, and, in 1520 a primary radiation configuration 1322 for the irradiation application may be determined, as disclosed herein. In 1536, a scattering medium configuration 145 for the scattering medium 140 of the irradiation device 100 may be determined, as disclosed herein. In 1538, the primary radiation configuration 1322 determined in 1520 may be refined based, at least in part, on the determined scattering medium configuration 145 (e.g., based on projected scattering metrics). The primary radiation configuration 1322 and scattering medium configuration 145 may be included in an irradiation configuration 1312.

In some implementations, the irradiation configuration 1312 may be iteratively modified and/or refined in 1514-1544. In 1540, an IRCU metric for the irradiation configuration 1312 may be determined and, in 1544, the decision of whether to accept the irradiation configuration 1312 may be based, at least in part, on the determined IRCU metric. If the irradiation configuration 1312 is not accepted at 1544, the flow may continue at 1514; otherwise, the flow may continue at 1550. In 1550, the irradiation configuration 1312 may be implemented by use of an irradiation device 100, as disclosed herein.

In 1560, feedback data pertaining to implementation of the irradiation application by the irradiation device 100 may be acquired. The feedback data may be acquired from the irradiation device 100, test instruments, a test environment (e.g., an ion chamber), radiation sensors, AEC, and/or the like. The feedback data may be used to refine a model used to determine the irradiation configuration 1312, such as the dose modeling module 1320 used to determine the primary radiation configuration 1322, the scatter modeling module 1330 used to determine the scattering medium configuration 145, and/or the like. The feedback data may be utilized to learn and/or refine correlational relationships comprising the models, such as correlational relationships between the depth of the target material 130 and penetration of the primary radiation 120, irradiation performance improvements realized by scattering media 140 having specified scattering medium configurations 145, and so on, as disclosed herein.

In 1562, a decision of whether to adapt the irradiation configuration 1312 may be determined. The decision in 1562 may be based on a difference between expected or estimated irradiation performance of the irradiation configuration 1312 and actual, observed irradiation performance during implementation of the irradiation configuration 1312 at 1550 (e.g., an irradiation error). In 1562, the irradiation configuration 1562 may be modified in response to determining that the irradiation error exceeds a threshold.

FIG. 16A is a flowchart 1600A illustrating examples of techniques for irradiating a target 130 by an irradiation device 100. In 1610, the target 130 may be enclosed within an irradiation device 100, which may comprise enclosing the target 130 (and/or target material 130) within the interior volume 112 of the enclosure 102 of the irradiation device 100. In some embodiments, control logic 201 of the irradiation device 100 may be configured to open the enclosure 102 to enable the target 130 to be received within the interior volume 112. The interior volume 112 may comprise a scattering medium 140, as disclosed herein. In some implementations, the scattering medium 140 may be disposed on one or more interior surfaces of the enclosure 102 of the irradiation device. In some implementations, the target 130 may be placed on a scattering medium 140 (e.g., may be placed on and/or within a receptacle 810 or container 1100 that comprises and/or is coupled to the scattering medium 140). The scattering medium configuration 145 of the scattering medium 140 may be adapted to improve aspects of irradiation performance, as disclosed herein. More specifically, the scattering medium configuration 145 may be determined based on one or more of: a) an energy composition 520 of the primary radiation 120 emitted by the source 110 of the irradiation device 100, b) target characteristics 135 of the target 130, c) the position and/or orientation of the target 130 relative to the primary radiation 120 (and/or propagation direction(s) 124 of the primary radiation 120), and so on, as disclosed herein.

In 1620, the source 110 of the irradiation device 100 may be configured to emit primary radiation 120 into the interior volume 112 of the enclosure 102. The source 110 may be configured to emit the primary radiation 120 by control logic 201, as disclosed herein. The primary radiation 120 may have a specified energy composition 520, energy level 521, and/or energy range 522. The source 110 may be further configured to emit the primary radiation 120 for a specified irradiation time (and/or in accordance with a specified irradiation pattern).

In 1630, the scattering medium configuration 145 of the scattering medium 140 disposed within the irradiation device 100 may cause secondary radiation 160 to be emitted into the interior volume 112 of the irradiation device 100 in response to the primary radiation 120. The secondary radiation 160 may be produced through Compton scatter interactions within the scattering medium 140, as disclosed herein. The secondary radiation 160 may irradiate at least a portion of the target 130.

FIG. 16B is a flowchart 1600B illustrating examples of techniques for irradiating a target 130 by an irradiation device 100. Step 1640 may comprise providing an enclosure 102 configured to enclose a target material 130 within an interior volume 112 of an irradiation device 100. Step 1650 may comprise producing a scattering medium 140 for the irradiation device 100. Step 1650 may comprise determining a scattering medium configuration 145 for the scattering medium 140 based, at least in part, on irradiation characteristics 405 of the irradiation device 100. Step 1650 may comprise configuring the scattering medium 140 to emit secondary radiation 160 into the interior volume 112 of the irradiation device 100 in response to primary radiation 120 generated by a source 110 of the irradiation device. The scattering medium 140 may be configured to produce the secondary radiation 160 through scatter interactions, as disclosed herein. Step 1660 may comprise configuring a thickness (146) of the scattering medium 140 relative to the primary radiation 120 to be 3 mm or greater. Step 1660 may comprise determining a suitable (or optimal) thickness (146) based, at least in part, on a scattering cross section and/or absorption cross section of the scattering medium 140, as disclosed herein.

FIG. 17 illustrates an example of an irradiation system 1700. The irradiation system 1700 may comprise an irradiation device 100, as disclosed herein. Non-limiting examples of an irradiation device 100 of an irradiation system 1700 are illustrated in FIGS. 1A, 2A, 3A, 4A, 7, 8A, 9, 10, 11A, 11D, 11F, and 12A-B. The irradiation system 1700 may comprise means for receiving and/or enclosing a target material 130 (receiving means 1702), means for emitting primary radiation 120 (emitting means 1710), and means for producing secondary radiation 160 in response to the primary radiation 120 (scattering means 1740).

The receiving means 1702 may comprise an enclosure 102 configured to define an interior volume 112 of the irradiation system 1700. The enclosure 102 may comprise and/or incorporate shielding 204, which may be configured to prevent radiation from escaping from the interior volume 112. The enclosure 102 and/or shielding 204 of the receiving means 1702 may comprise any suitable structure and/or materials including, but not limited to: lead, lead sheeting, lead cladding, lead casing, lead composite, lead epoxy, lead bricks, tin, antimony, tungsten, bismuth, sheeting comprising a tungsten, bismuth or barium sulfate powder, cement, x-ray glass, laminated x-ray glass, and/or the like. Non-limiting examples of enclosures 102 are illustrated in FIGS. 1A, 2A, 3A, 4A, 7, 8A, 9, 10, 11A, 11D, 11F, and 12A-B.

The receiving means 1702 may further comprise means for transitioning the enclosure 102 between an open configuration in which target material 130 may be received within the interior volume 112 and a closed configuration in which the target material 130 is enclosed within the interior volume 112. In some implementations, the receiving means 1702 may comprise one or more access mechanisms 206, as disclosed herein.

The emitting means 1710 may be configured to emit primary radiation 120 into and/or within the enclosure 102. The primary radiation 120 may be configured to irradiate at least a first portion of the target material 130 within the interior volume 112. The emitting means 1710 may comprise any suitable means for generating, controlling, emitting and/or directing primary radiation 120, including, but not limited to: a radiation source (e.g., a source 110, as disclosed herein), an x-ray source, an x-ray emitter, an x-ray laser, a vacuum tube, an x-ray tube, a cold cathode x-ray tube, a hot cathode x-ray tube, a rotating anode x-ray tube, a microfocus x-ray tube, a multi-source x-ray tube, an emitter, an x-ray emitter, a nanotube (NT) emitter, and/or the like.

The scattering means 1740 may be configured to produce secondary radiation 160 in response to the primary radiation 120. The secondary radiation 160 may be produced through Compton scatter interactions, as disclosed herein. The secondary radiation 160 may be configured to irradiate at least a second portion of the target material 130. The scattering means 1740 may comprise a scattering medium 140 having a suitable (or optimal) scattering medium configuration 145. The scattering medium configuration 145 may be determined based, at least in part, on irradiation characteristics 405 of the irradiation system 1700, such as an energy composition 520 of the primary radiation 120, target characteristics 135 of the target material 130, and/or the like. Non-limiting examples of scattering media 140 having respective scattering medium configurations 145 are illustrated in FIGS. 1A, 1B, 2A, 3A, 4A, 5A, 6A, 7, 8A-H, 9, 10, 11A-H, and 12A-B. The scattering medium 140 may have a thickness 146 of at least 0.3 cm (or at least 0.6 cm). The depth axis of the scattering medium 140 may be aligned with a propagation direction 124 (or propagation direction(s) 124) of the primary radiation 120. The material composition 142 of the scattering medium 140 comprise one or more of a carbon-based material, polymer, organic polymer, plastic, plastic polymer, synthetic polymer, thermoplastic, thermoplastic polymer, nylon, PVC, polystyrene, POM, acetal, acetal resin, an acetal plastic, polyacetal, polyformaldehyde, HDPE, aluminum, an aluminum alloy, and/or the like.

In some implementations, the irradiation system 1700 may further comprise receptacle means 1770 configured to hold the target material 130 within the receiving means 1702. In some embodiments, at least a portion of the scattering means 1740 may be disposed on the receptacle means 1770. Alternatively, or in addition, at least a portion of the receptacle means 1770 may comprise and/or be implemented by at least a portion of the scattering means 1740 (e.g., by a portion of the scattering medium 140). In some implementations, portions of the receptacle means 1770 may comprise and/or be implemented by a receptacle 810 and/or container 1110, as disclosed herein. Non-limiting examples of receptacle means 1770 are illustrated in FIGS. 7, 8A-H, 9, 10, 11A-H, and 12A.

Disclosed herein are examples of systems, devices, methods, and non-transitory computer-readable storage media for improved irradiation performance without the need for physical manipulation and/or over-radiation.

Some embodiments include an irradiation device (100), comprising an enclosure (102) configured to receive a target material (130); a source (110) configured to emit primary radiation (120) within the enclosure (102), the primary radiation (120) configured to irradiate at least a first portion of the target material (130); and a scattering medium (140) disposed within the enclosure (102), the scattering medium (140) configured to produce secondary radiation (160) through scatter interactions in response to the primary radiation (120), the secondary radiation (160) configured to irradiate at least a second portion of the target material (130), wherein the scattering medium (140) has a thickness (146) of at least 3 millimeters (mm).

In some embodiments, the scattering medium (140) has a thickness (146) of at least 6 millimeters.

In some embodiments, wherein the thickness (146) of the scattering medium (140) relative to the primary radiation (120) is at least one of 0.25 inches and 0.6 centimeters.

In some embodiments, the source (110) is configured to emit the primary radiation (120) at a specified energy level (521), and wherein the scattering medium (140) is configured to comprise a material having an atomic number at which Compton scattering is dominant over photoelectric absorption and pair production at the specified energy level (521).

In some embodiments, the scattering medium (140) comprises a material having an atomic number less than or equal to 20.

In some embodiments, the scattering medium (140) comprises a material having an atomic number less than or equal to 13.

In some embodiments, the scattering medium (140) comprises one or more of aluminum and an aluminum alloy.

In some embodiments, the scattering medium (140) comprises one or more of a carbon-based material, polymer, organic polymer, plastic, plastic polymer, synthetic polymer, thermoplastic, thermoplastic polymer, nylon, polyvinyl chloride, polystyrene, polyoxymethylene, acetal, acetal resin, an acetal plastic, polyacetal, polyformaldehyde, and high-density polyethylene.

In some embodiments, the scattering medium (140) comprises one or more of a carbon-based material, polymer, organic polymer, plastic, plastic polymer, synthetic polymer, thermoplastic, thermoplastic polymer, nylon, polyvinyl chloride, polystyrene, polyoxymethylene, acetal, acetal resin, an acetal plastic, polyacetal, polyformaldehyde, high-density polyethylene, aluminum, and an aluminum alloy.

In some embodiments, the thickness (146) of the scattering medium (140) is set at a point at which a scatter cross section of the scattering medium (140) exceeds an absorption cross section of the scattering medium (140) by at least a threshold.

In some embodiments, the target material (130) comprises cannabis, and wherein the primary radiation (120) comprises x-ray radiation between 40 kiloelectron volts and 600 kiloelectron volts. In some embodiments, the primary radiation (120) is at one or more of 140 kiloelectron volts and 180 kiloelectron volts.

In some embodiments, a depth axis (744) of the scattering medium (140) is aligned with a propagation direction (124) of the primary radiation (120).

In some embodiments, the irradiation device (100) further comprises a receptacle (810) configured to hold at least a portion of the target material (130) within the enclosure (102), wherein the scattering medium (140) is disposed between a surface of the receptacle (810) and the target material (130), and wherein the thickness (146) of the scattering medium (140) is greater than a thickness of the receptacle (810).

In some embodiments, the irradiation device (100) further comprises a receptacle (810) configured to hold at least a portion of the target material (130) within the enclosure (102), wherein the scattering medium (140) forms at least a portion of the receptacle (810).

In some embodiments, the irradiation device (100) further comprises a receptacle (810) configured to hold at least a portion of the target material (130), wherein the scattering medium (140) is configured to form at least a portion of one or more of a base of the receptacle (810) a sidewall of the receptacle (810) and a cylindrical wall of the receptacle (810).

In some embodiments, the source (110) of the irradiation device (100) is configured to emit the primary radiation (120) into an irradiation zone (1222) and the irradiation device (100) further comprises a conveyor (1210) configured to transfer the target material (130) through the irradiation zone (1222).

Disclosed herein are embodiments of a method for providing an improved irradiation device (100). Some embodiments of the disclosed method comprise: providing an enclosure (102) configured to enclose a target material (130) within an interior volume (112) of an irradiation device (100); producing a scattering medium (140) configured to emit secondary radiation (160) into the interior volume (112) of the irradiation device (100) in response to primary radiation (120) generated by a source (110) of the irradiation device (100), the secondary radiation (160) produced through scatter interactions within the scattering medium (140); and configuring a thickness (146) of the scattering medium (140) relative to the primary radiation (120) to be 3 millimeters or greater.

In some embodiments, the method further comprises configuring a depth axis (744) of the scattering medium (140) to align with a propagation direction (124) of the primary radiation (120).

In some embodiments, the scattering medium (140) may be configured to reduce a radiation dosage differential between a maximum-exposure region (131) of the target material (130) and a minimum-exposure region (139) of the target material (130) to less than about 10%.

In some embodiments, the method further comprises determining the thickness (146) for the scattering medium (140) relative to the primary radiation (120) based on a scattering cross section of the scattering medium (140) and an absorption cross section of the scattering medium (140), wherein the determined thickness (146) is at least 6 millimeters.

Disclosed herein are methods for improved irradiation, comprising enclosing a target material (130) within an interior volume (112) an enclosure (102); emitting primary radiation (120) into the interior volume (112) of the enclosure (102); and causing secondary radiation (160) to be emitted into the interior volume (112) of the enclosure (102) in response to primary radiation (120), the secondary radiation (160) produced through scatter interactions within a scattering medium (140) disposed within the enclosure, the scattering medium (140) having a thickness (146) of at least 3 millimeters. In some implementations, the scattering medium (140) may have a thickness of 6 millimeters or greater. The thickness (146) may be determined based, at least in part, on a scattering cross section and absorption cross section of the scattering medium (140).

Embodiments of the method may further comprise configuring a depth axis (744) of the scattering medium (140) to align with a propagation direction (124) of the primary radiation (120). The scattering medium (140) may be configured to reduce a radiation dose differential of the target material (130) to less than about 10%.

Some embodiments include a system, comprising: means for receiving a target material (130) to be irradiated within an interior volume (112) of an enclosure (102); means for emitting primary radiation (120) into the enclosure (102), the primary radiation (120) configured to irradiate at least a first portion of the target material (130); and means for producing secondary radiation (160) through scatter interactions within a scattering medium (140), the secondary radiation (160) configured to irradiate at least a second portion of the target material (130).

In some embodiments, the system further comprises receptacle means (1770) configured to hold at least a portion of the target material (130) within the interior volume (112), wherein at least a portion of the scattering medium (140) is disposed on the receptacle means (1770).

In some embodiments, the system further comprises receptacle means (1770) configured to hold to hold at least a portion of the target material (130) within the interior volume (112), wherein at least a portion of the receptacle means (1770) is formed from the scattering medium (140).

In some embodiments, a thickness (146) of the scattering medium (140) relative to the primary radiation (120) is at least 6 millimeters.

In some embodiments, the scattering medium (140) comprises a material having an atomic number selected from a determined range of atomic numbers, the range comprising atomic numbers for which Compton scattering exceeds photoelectric absorption at an energy of the primary radiation (120).

Disclosed are embodiments of methods for configuring an irradiation device (100) and/or a scattering medium (140) for the irradiation device (100). Also disclosed are embodiments of non-transitory computer-readable storage media comprising instructions configured to cause a processor of a device to implement aspects of the disclosed methods, which may comprise determining a first irradiation time for primary radiation (120) produced by a source (110) of an irradiation device (100), the first irradiation time configured to deliver a threshold radiation dose to a target (130); configuring a scattering medium (140) of the irradiation device (100) based, at least in part, on an energy of the primary radiation (120) produced by the source (110) of the irradiation device (100), the scattering medium (140) configured to emit secondary radiation (160) in response to the primary radiation (120), the secondary radiation (160) configured to irradiate at least a portion of the target (130); determining a second irradiation time for the primary radiation (120) based, at least in part, on the configuration of the scattering medium (140); and configuring the irradiation device (100) to irradiate the target (130) for the second irradiation time.

In some embodiments, configuring the scattering medium (140) comprises identifying at atomic number at which Compton scattering is equivalent with one or more of photoelectric absorption and pair production within a specified energy range (522), wherein the scattering medium (120) is configured to include materials having atomic numbers less than the identified atomic number. The specified energy range (522) corresponds to at least a portion of an energy spectrum of the primary radiation (120).

In some embodiments, configuring the scattering medium (140) comprises identifying a first atomic number at which Compton scattering is equivalent to one or more of photoelectric absorption and pair production at a low end of a specified energy range (522) of the primary radiation (120); and identifying a second atomic number at which Compton scattering is equivalent to one or more of photoelectric absorption and pair production at a high end of the specified energy range (522). The scattering medium (140) may be configured to include materials having atomic numbers less than both the first atomic number and the second atomic number.

In some embodiments, the scattering medium (140) comprises determining a thickness (146) of the scattering medium (140) relative to a propagation direction (124) of the primary radiation (120), comprising identifying a propagation depth at which cumulative scattering of the scattering medium (140) exceeds cumulative photoelectric absorption of the scattering medium (140) by at least a threshold.

In some embodiments, configuring the scattering medium (140) comprises determining a thickness (146) of the scattering medium (140) relative to a propagation direction (124) of the primary radiation (120), comprising identifying a propagation depth at which an increase rate of an intensity of the secondary radiation (160) falls below a threshold.

Some embodiments of the disclosed method further comprise determining an energy level (521) for the primary radiation (120) based on one or more characteristics of the target (130).

Some embodiments of the disclosed method further comprise estimating an increase to a radiation dose rate of the target (130) produced by the scattering medium (140); and determining the second irradiation time for the primary radiation (120) based, at least in part, on the estimated increase to the radiation dose rate.

In some implementations, the method further comprises estimating a decrease to a radiation dose rate differential between regions of the target (130) produced by the scattering medium (140); and determining the second irradiation time for the primary radiation (120) based, at least in part, on the estimated decrease to the radiation dose rate differential.

Some embodiments of the disclosed method may further comprise acquiring feedback data indicating an actual radiation dose delivered to the target during over the second irradiation time; and modeling relationships between one or more characteristics of the scattering medium and one or more aspects of irradiation performance based, at least in part, on the acquired feedback data.

In some implementations, the disclosed method may further comprise determining an irradiation configuration (1312), the irradiation configuration (1312) specifying an energy of the primary radiation (120), the second irradiation time, the configuration of the scattering medium (140), and one or more characteristics of the target (130); calculating a utility of the irradiation configuration (1312); modifying the irradiation configuration (1312) in response to determining that the utility of the irradiation configuration (1312) fails to satisfy a threshold; and implementing the irradiation configuration (1312) in response to determining that the utility of the irradiation configuration (1312) satisfies the threshold.

Although the structures, devices, methods, and systems have been described in accordance with particular embodiments, one of ordinary skill in the art will readily recognize that many variations to the particular embodiments are possible, and any variations should therefore be considered to be within the spirit and scope disclosed herein. Accordingly, many modifications may be made by one of ordinary skill in the art without departing from the spirit and scope of the appended claims.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the claims beginning with claim [x] and ending with the claim that immediately precedes this one," where the bracketed term "[x]" is replaced with the number of the most recently recited independent claim. For example, for the first claim set that begins with independent claim 1, claim 4 can depend from either of claims 1 and 3, with these separate dependencies yielding two distinct embodiments; claim 5 can depend from any one of claim 1, 3, or 4, with these separate dependencies yielding three distinct embodiments; claim 6 can depend from any one of claim 1, 3, 4, or 5, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed to cover the corresponding structure, material, or acts described herein and equivalents thereof in accordance with 35 U.S.C. § 112(f). Embodiments of the invention in which an exclusive property or privilege is claimed are defined as follows.

What is claimed is:

1. An irradiation device, comprising:
an enclosure configured to receive a target material;
a source configured to emit primary radiation within the enclosure, the primary radiation comprises x-ray radiation configured to irradiate at least a first portion of the target material; and
a scattering medium disposed within the enclosure, the scattering medium configured to produce secondary radiation through scatter interactions in response to the primary radiation, the secondary radiation configured to irradiate at least a second portion of the target material, wherein the scattering medium has a thickness of at least 3 millimeters (mm).

2. The irradiation device of claim 1, wherein the thickness of the scattering medium is at least 6 millimeters.

3. The irradiation device of claim 1, wherein the source is configured to emit the primary radiation at a specified energy level, and wherein the scattering medium is configured to comprise a material having an atomic number at which Compton scattering ($\sigma$) is dominant over photoelectric absorption ($\tau$) and pair production (k) at the specified energy level.

4. The irradiation device of claim 1, wherein the scattering medium comprises a material having an atomic number less than or equal to 20.

5. The irradiation device of claim 1, wherein the scattering medium comprises a material having an atomic number less than or equal to 13.

6. The irradiation device of claim 1, wherein the scattering medium comprises one or more of aluminum and an aluminum alloy.

7. The irradiation device of claim 1, wherein the scattering medium comprises one or more of a carbon-based material, polymer, organic polymer, plastic, plastic polymer, synthetic polymer, thermoplastic, thermoplastic polymer, nylon, polyvinyl chloride, polystyrene, polyoxymethylene, acetal, acetal resin, an acetal plastic, polyacetal, polyformaldehyde, and high-density polyethylene.

8. The irradiation device of claim 1, wherein the thickness of the scattering medium is set at a point at which a scatter cross section of the scattering medium exceeds an absorption cross section of the scattering medium by at least a threshold.

9. The irradiation device of claim 1, wherein the primary radiation comprises x-ray radiation between 40 kiloelectron volts and 600 kiloelectron volts.

10. The irradiation device of claim 1, wherein a surface of the scattering medium is substantially normal to the primary radiation along the surface.

11. The irradiation device of claim 1, further comprising a receptacle configured to hold at least a portion of the target material within the enclosure, wherein the scattering medium is disposed between a surface of the receptacle and the target material, and wherein a thickness of the scattering medium is greater than a thickness of the receptacle.

12. The irradiation device of claim 1, further comprising a receptacle configured to hold at least a portion of the target material within the enclosure, wherein the scattering medium forms at least a portion of the receptacle.

13. The irradiation device of claim 1, further comprising a receptacle configured to hold at least a portion of the target material, wherein the scattering medium is configured to form at least a portion of one or more of a base of the receptacle, a sidewall of the receptacle, and a cylindrical wall of the receptacle.

14. The irradiation device of claim 1, wherein the source is configured to emit the primary radiation into an irradiation zone, and wherein the irradiation device further comprises a conveyor configured to transfer the target material through the irradiation zone.

15. The irradiation device of claim 1, wherein the target material comprises a biological substance.

16. The irradiation device of claim 1, further comprising:
a receptacle disposed within and separate from the enclosure, configured to receive the target material, and comprising the scattering medium, wherein the receptacle is configured such that at least part of the primary radiation passes through the target material before scattering from the scattering medium.

17. An irradiation method, comprising:
providing an enclosure configured to enclose a target material within an interior volume of an irradiation device;
producing a scattering medium configured to emit secondary radiation into the interior volume of the irradiation device in response to primary radiation generated by an x-ray source of the irradiation device, the secondary radiation produced through scatter interactions within the scattering medium; and
configuring a thickness of the scattering medium relative to the primary radiation to be 3 millimeters or greater.

18. The irradiation method of claim 17, further comprising configuring a depth axis of the scattering medium to align with a propagation direction of the primary radiation.

19. The irradiation method of claim 17, wherein the scattering medium is configured to reduce a radiation dosage differential between a maximum-exposure region of the target material and a minimum-exposure region of the target material to less than about 10%.

20. The irradiation method of claim 17, further comprising determining the thickness for the scattering medium relative to the primary radiation based on a scattering cross section of the scattering medium and an absorption cross section of the scattering medium, wherein the determined thickness is at least 6 millimeters.

21. An irradiation system, comprising:
means for receiving a target material to be irradiated within an interior volume of an enclosure;
means for emitting primary radiation into the enclosure, the primary radiation comprises x-ray radiation configured to irradiate at least a first portion of the target material; and
means for producing secondary radiation through scatter interactions within a scattering medium, the secondary radiation configured to irradiate at least a second portion of the target material.

22. The irradiation system of claim 21, further comprising receptacle means configured to hold the target material within the interior volume, wherein at least a portion of the scattering medium is disposed on the receptacle means.

23. The irradiation system of claim 21, further comprising receptacle means configured to hold at least a portion of the target material within the interior volume, wherein at least a portion of the receptacle means are formed from the scattering medium.

24. The irradiation system of claim 21, wherein a thickness of the scattering medium relative to a propagation direction of the primary radiation is at least 6 millimeters.

25. The irradiation system of claim 21, wherein the scattering medium comprises a material having an atomic number selected from a determined range of atomic numbers, the range comprising atomic numbers for which Compton scattering exceeds photoelectric absorption at an energy of the primary radiation.

26. An irradiation device, comprising:
an enclosure configured to receive a target material;
a source configured to emit primary radiation within the enclosure, the primary radiation configured to irradiate at least a first portion of the target material; and
a scattering medium disposed within the enclosure, the scattering medium configured to produce secondary radiation through scatter interactions in response to the primary radiation, the secondary radiation configured to irradiate at least a second portion of the target material, wherein the scattering medium has a thickness of at least 3 millimeters (mm);
wherein the source is configured to emit the primary radiation at a specified energy level, and wherein the scattering medium is configured to comprise a material having an atomic number at which Compton scattering ($\sigma$) is dominant over photoelectric absorption ($\tau$) and pair production (k) at the specified energy level.

* * * * *